United States Patent
Maruyama et al.

(10) Patent No.: US 8,191,422 B2
(45) Date of Patent: Jun. 5, 2012

(54) COPYING APPARATUS

(75) Inventors: Kensuke Maruyama, Tokyo (JP);
Osamu Yamaguchi, Sagamihara (JP);
Takashi Shimanuki, Yokohama (JP);
Koichi Tsuji, Machida (JP); Takahiro Ikeda, Yokosuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/536,526

(22) Filed: Aug. 6, 2009

(65) Prior Publication Data
US 2009/0288490 A1    Nov. 26, 2009

Related U.S. Application Data

(63) Continuation of application No. PCT/JP2008/068898, filed on Oct. 17, 2008.

(30) Foreign Application Priority Data

Oct. 19, 2007 (JP) ................................. 2007-272981
Aug. 27, 2008 (JP) ................................. 2008-218386

(51) Int. Cl.
*G01N 29/265* (2006.01)
*G01N 29/06* (2006.01)

(52) U.S. Cl. ............................................. 73/634; 73/633

(58) Field of Classification Search ............. 73/633–634
See application file for complete search history.

(56) References Cited

U.S. PATENT DOCUMENTS

| | | | | |
|---|---|---|---|---|
| 4,166,395 A | * | 9/1979 | Dannehl | 73/634 |
| 4,341,120 A | * | 7/1982 | Anderson | 73/618 |
| 5,571,968 A | * | 11/1996 | Buckley | 73/623 |
| 5,576,492 A | * | 11/1996 | Phalin | 73/634 |
| 5,952,578 A | * | 9/1999 | White | 73/622 |
| 7,337,673 B2 | * | 3/2008 | Kennedy et al. | 73/633 |
| 2005/0126291 A1 | * | 6/2005 | Czerw et al. | 73/589 |
| 2007/0006658 A1 | * | 1/2007 | Kennedy et al. | 73/622 |

FOREIGN PATENT DOCUMENTS

| | | |
|---|---|---|
| DE | 3643832 A1 | 6/1988 |
| JP | 61-96453 | 5/1986 |
| JP | 63-119984 | 5/1988 |
| JP | 05-249091 | 9/1993 |
| JP | 6-8552 | 3/1994 |
| JP | 6-242087 | 9/1994 |
| JP | 9-281094 | 10/1997 |
| JP | 2943948 | 6/1999 |
| JP | 3288924 | 3/2002 |
| RU | 2206087 C2 * | 6/2003 |

OTHER PUBLICATIONS

Extended European Search Report issued Apr. 4, 2011, in Application No. / Patent No. 08840178.1-2302 / 2192406 PCT/JP2008068898.

Office Action issued Oct. 17, 2011 in Korean Application Serial No. 10-2009-7012697. (with English translation).

* cited by examiner

*Primary Examiner* — Hezron E Williams
*Assistant Examiner* — Rose M Miller
(74) *Attorney, Agent, or Firm* — Oblon, Spivak, McClelland, Maier & Neustadt, L.L.P.

(57) ABSTRACT

There is provided a copying apparatus that copies a workpiece, including a shoe that comes into contact with a portion of the workpiece to be copied, and a first swiveling unit that swivels with the shoe in an arc pattern around a point, as a swiveling center, on a plane where the shoe comes into contact with the portion of the workpiece to be copied.

22 Claims, 39 Drawing Sheets

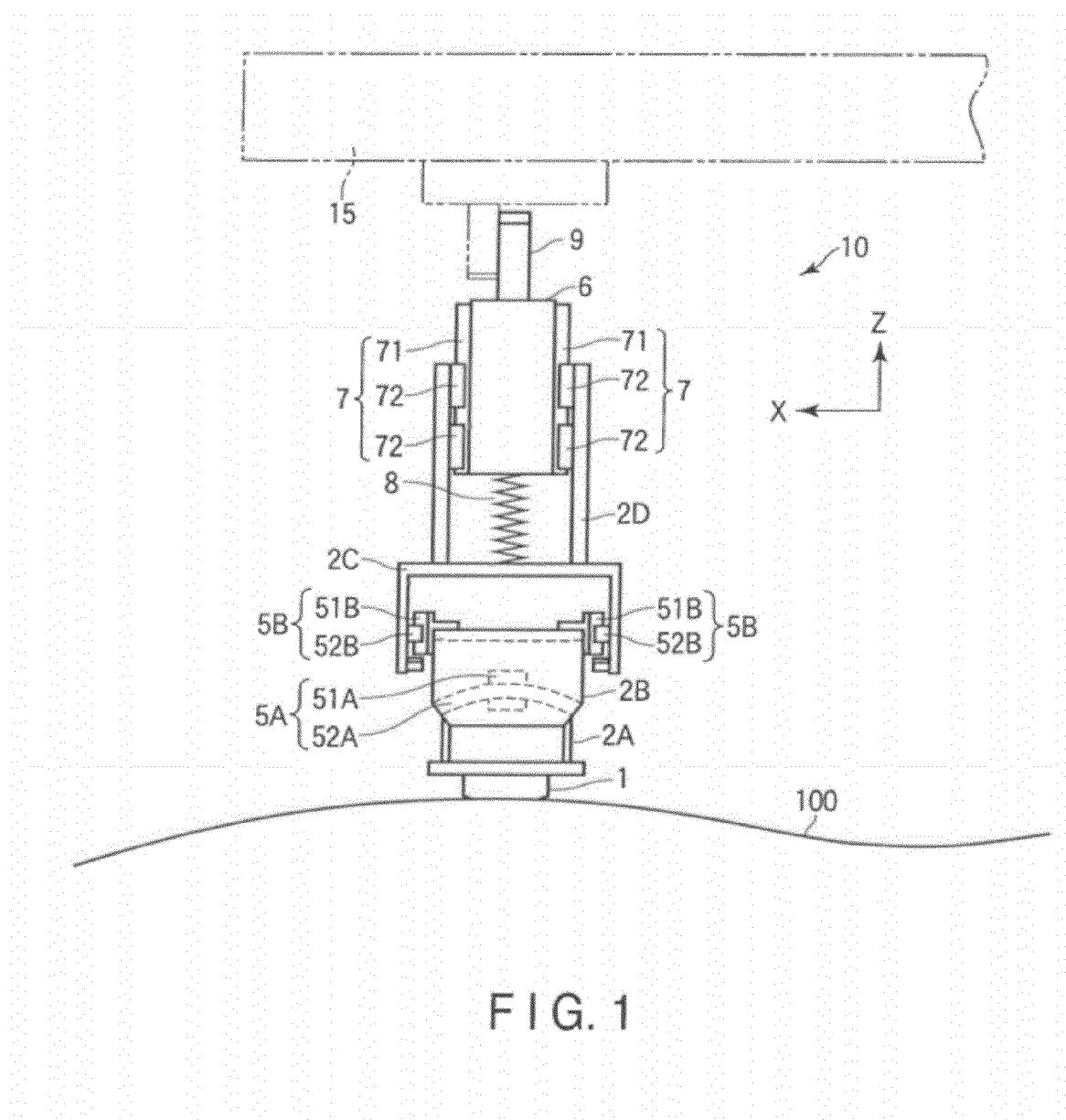
F I G. 1

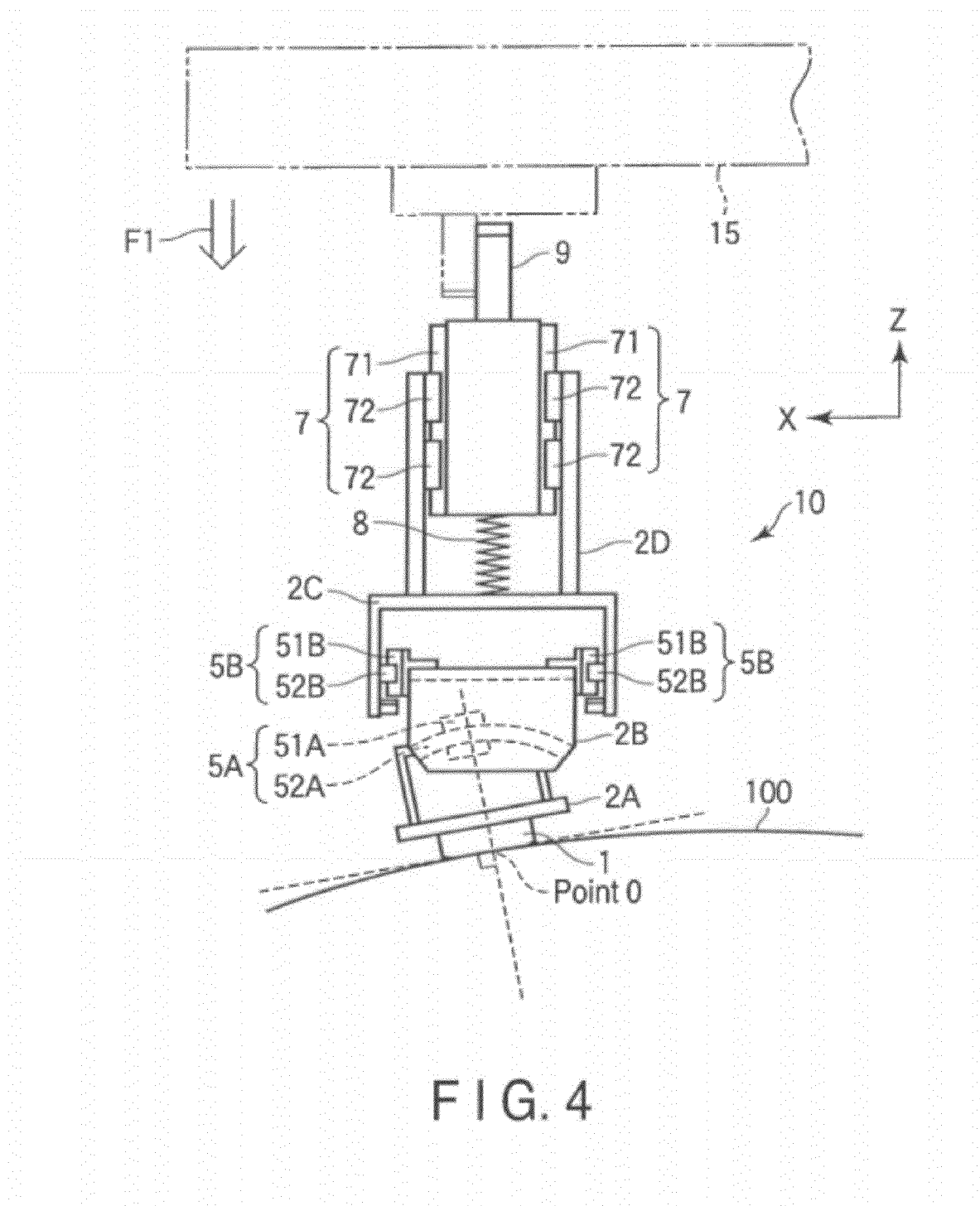
F I G. 4

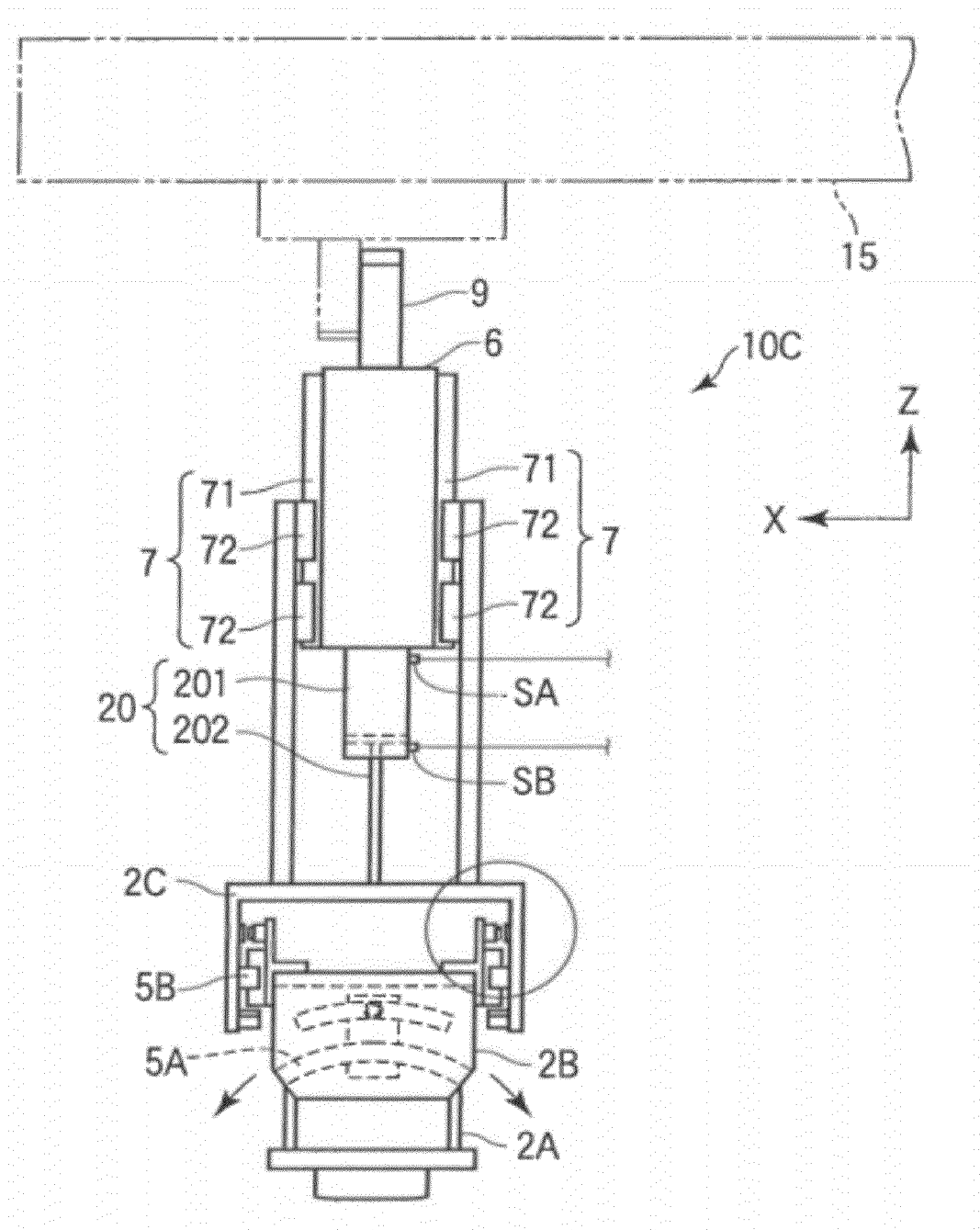
F I G. 8A

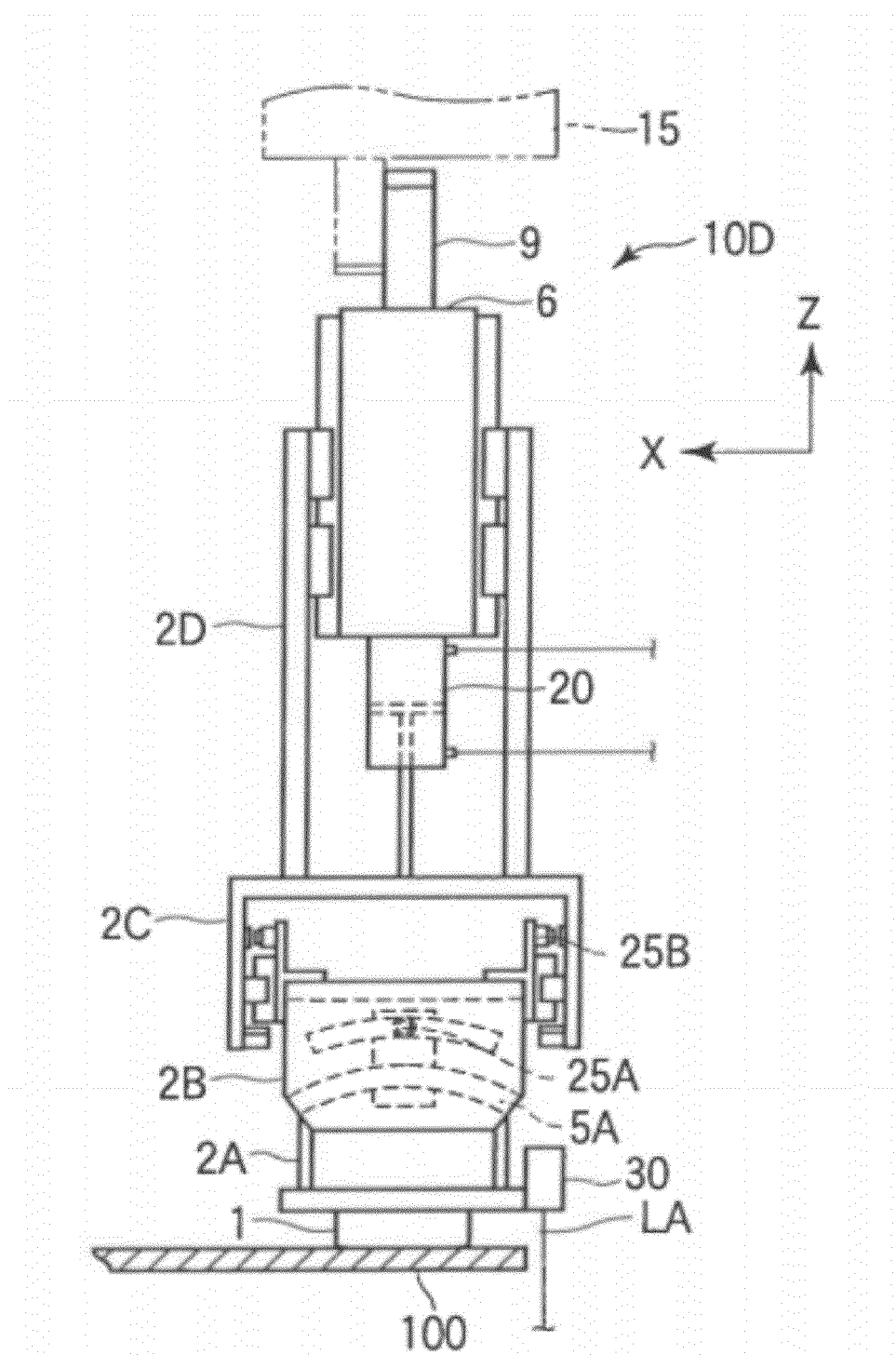
F I G. 12B

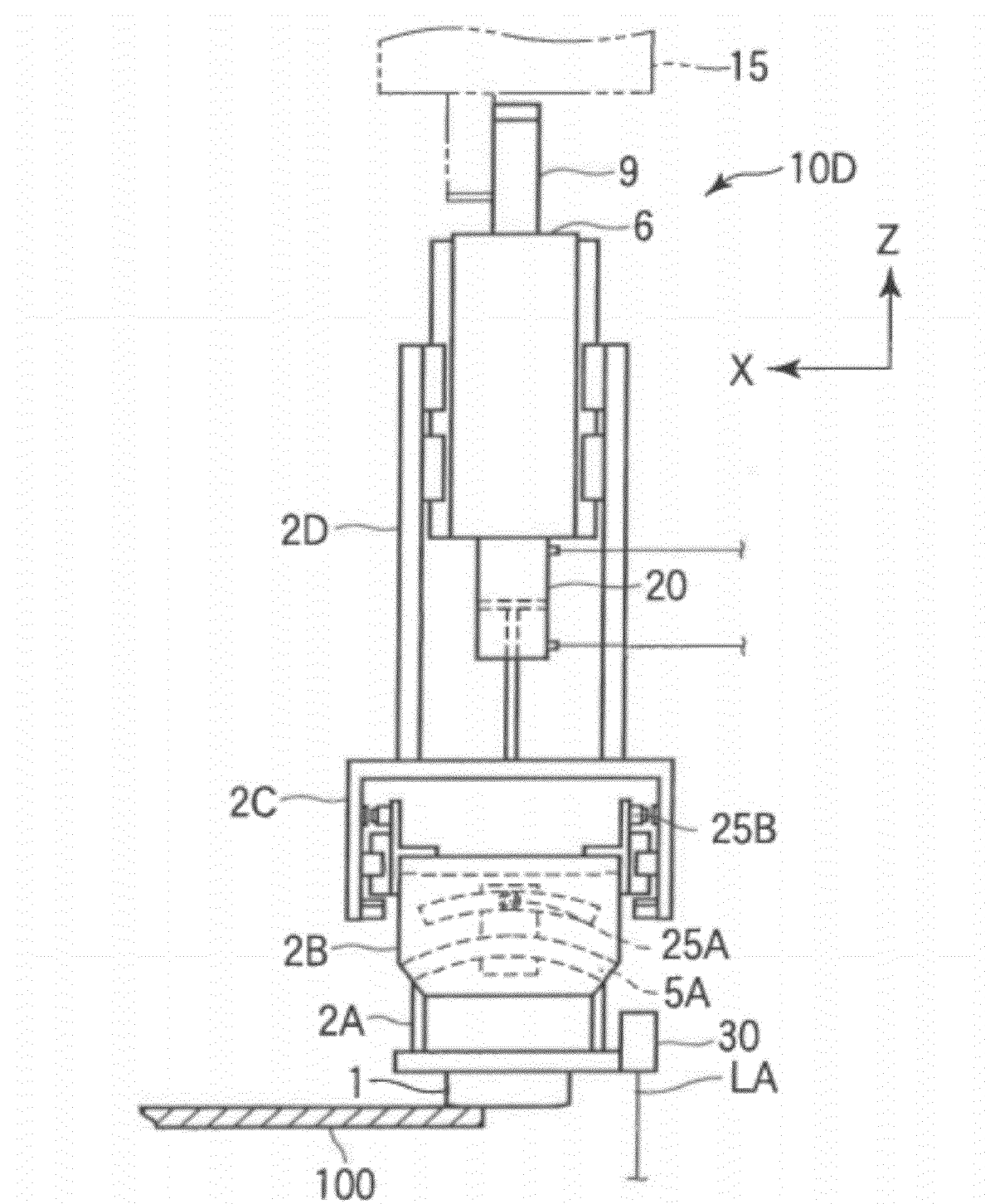
F I G. 12C

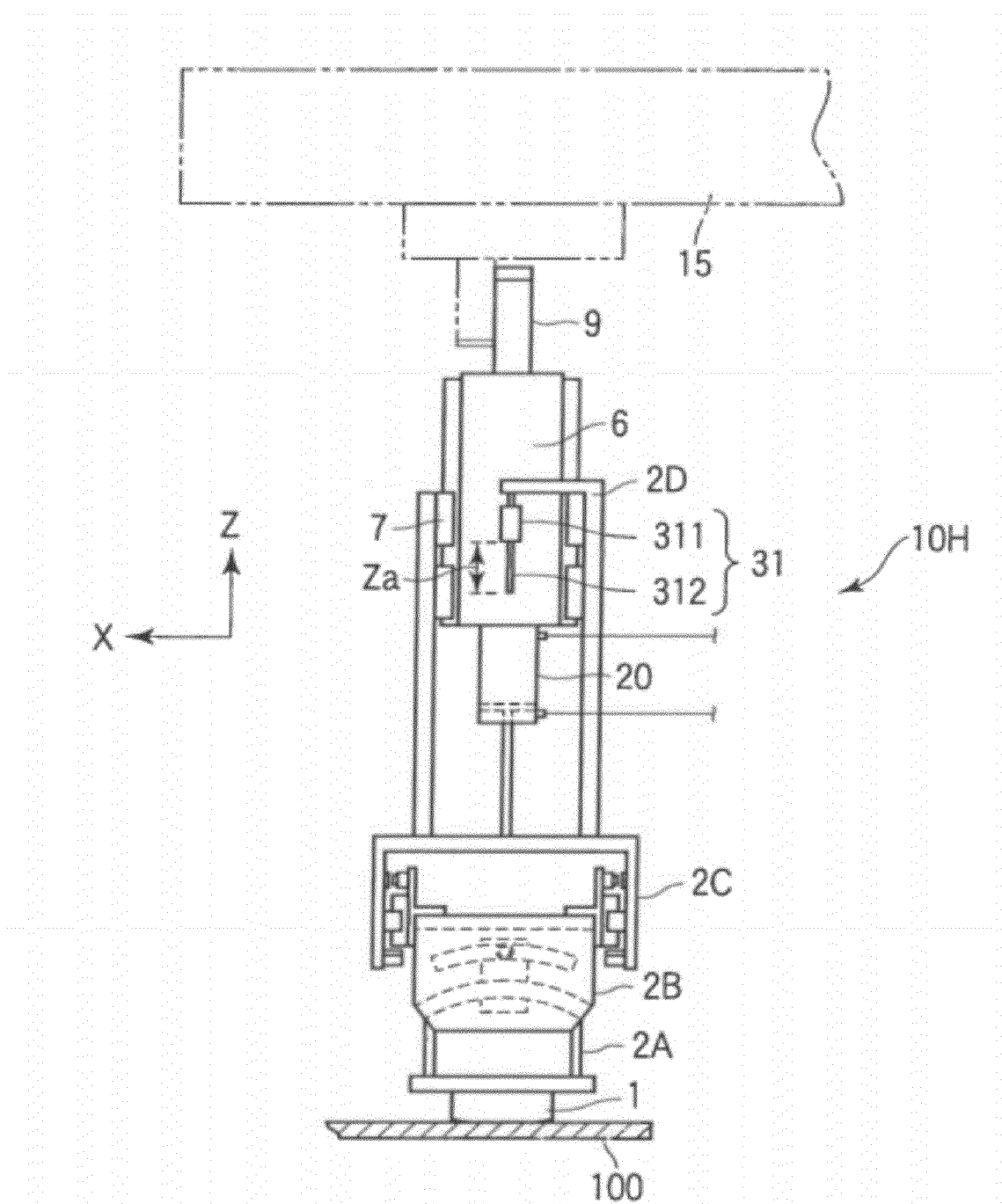
F I G. 18A

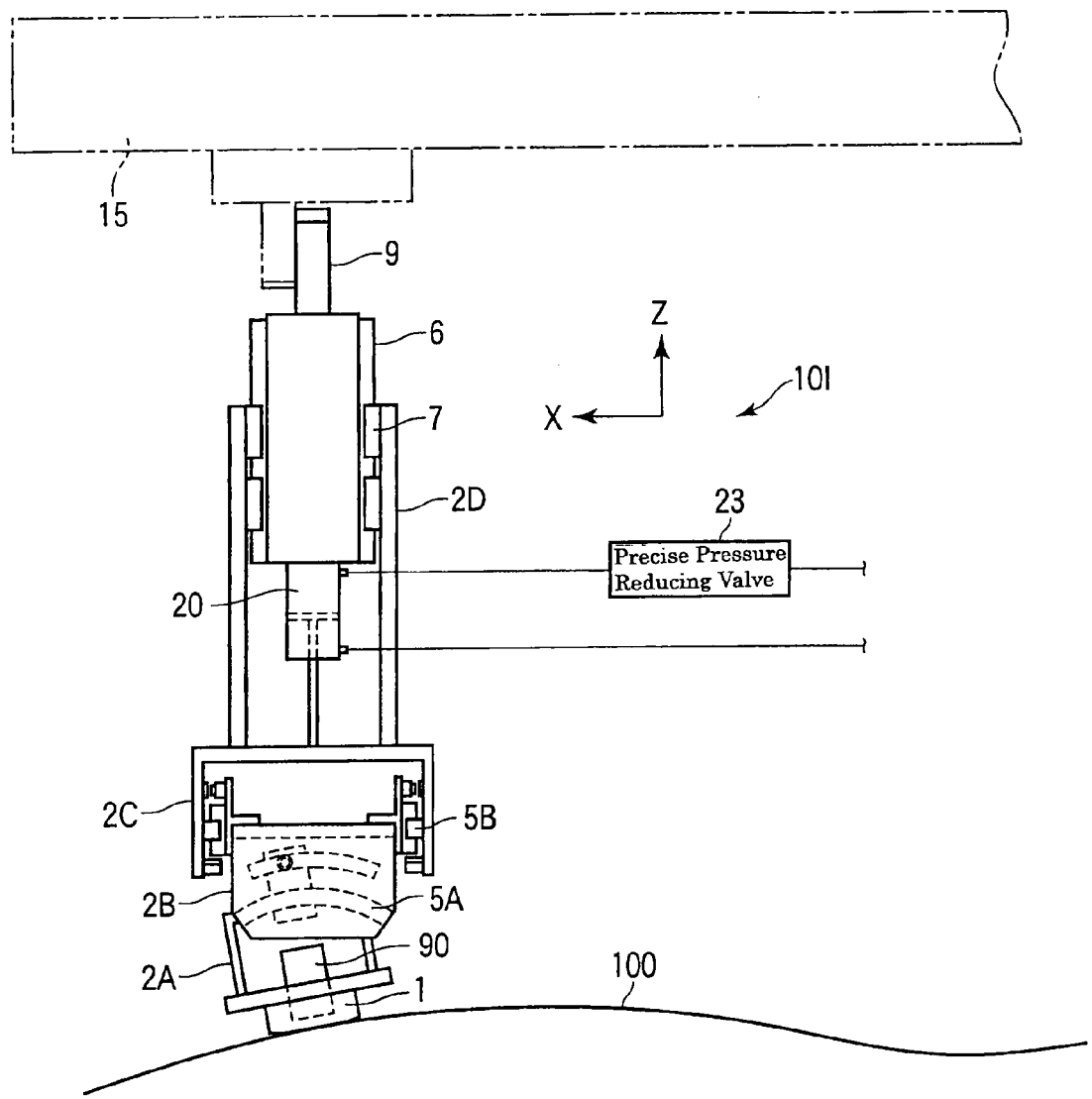
F I G. 19

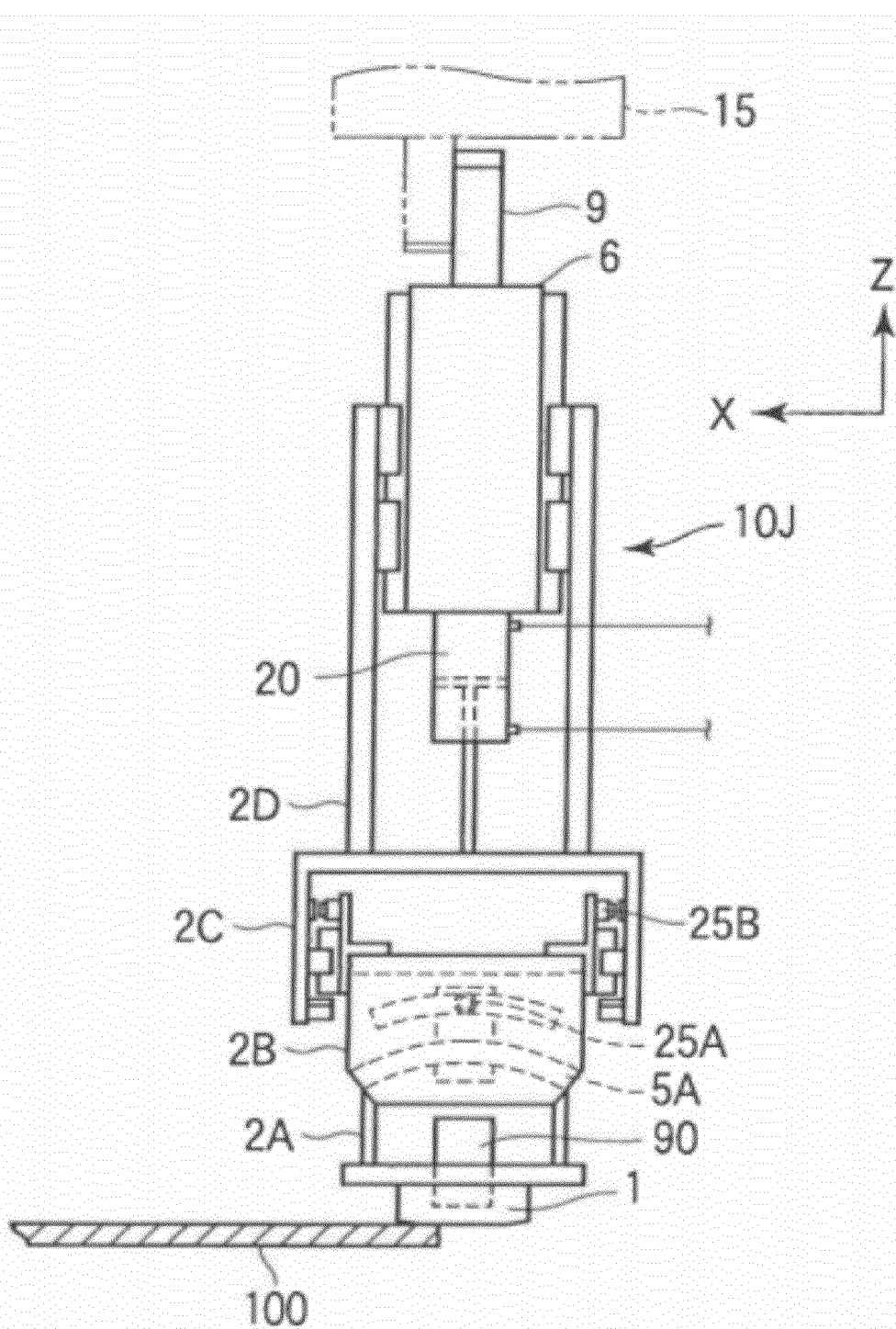
F I G. 23C

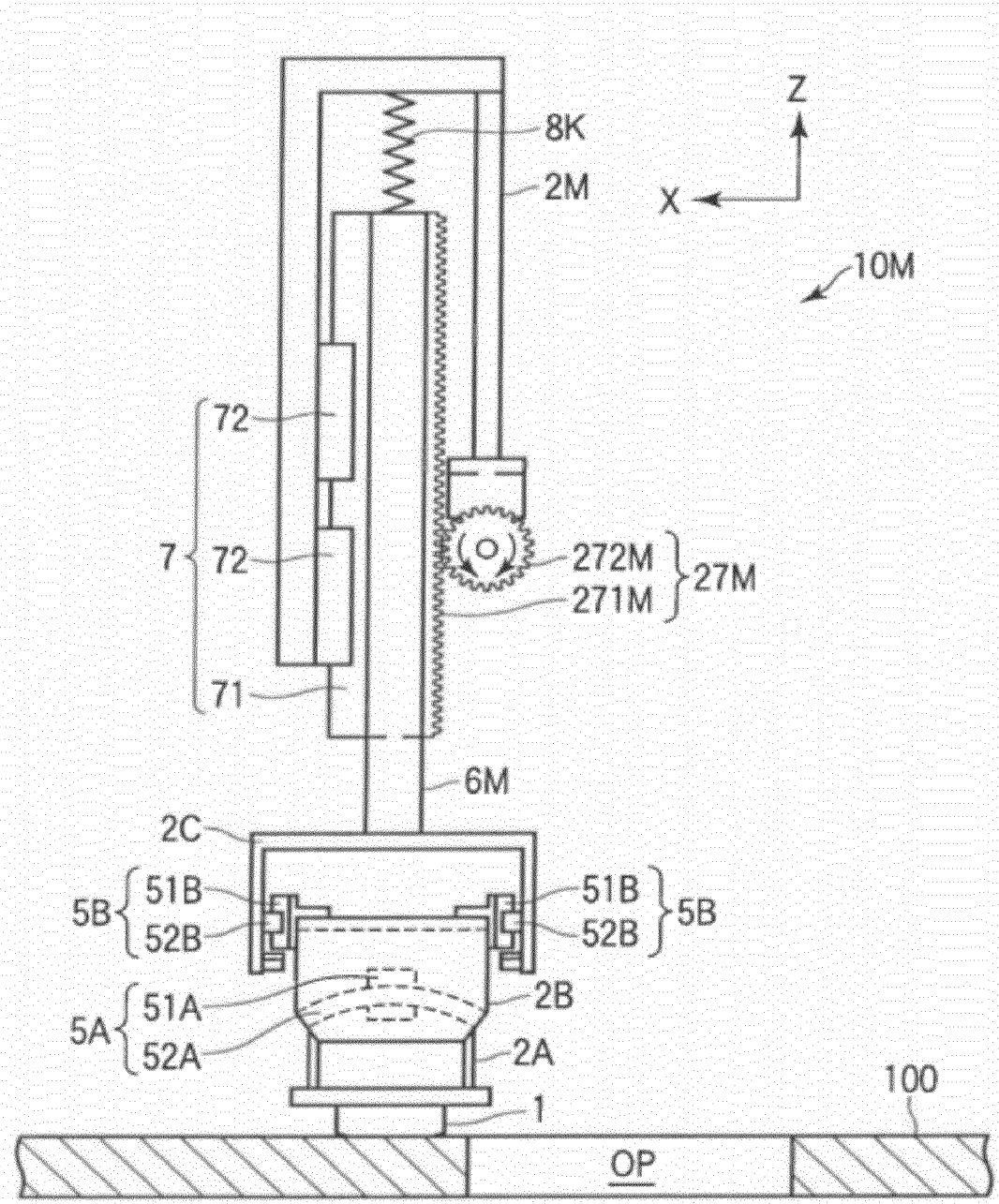
F I G. 29

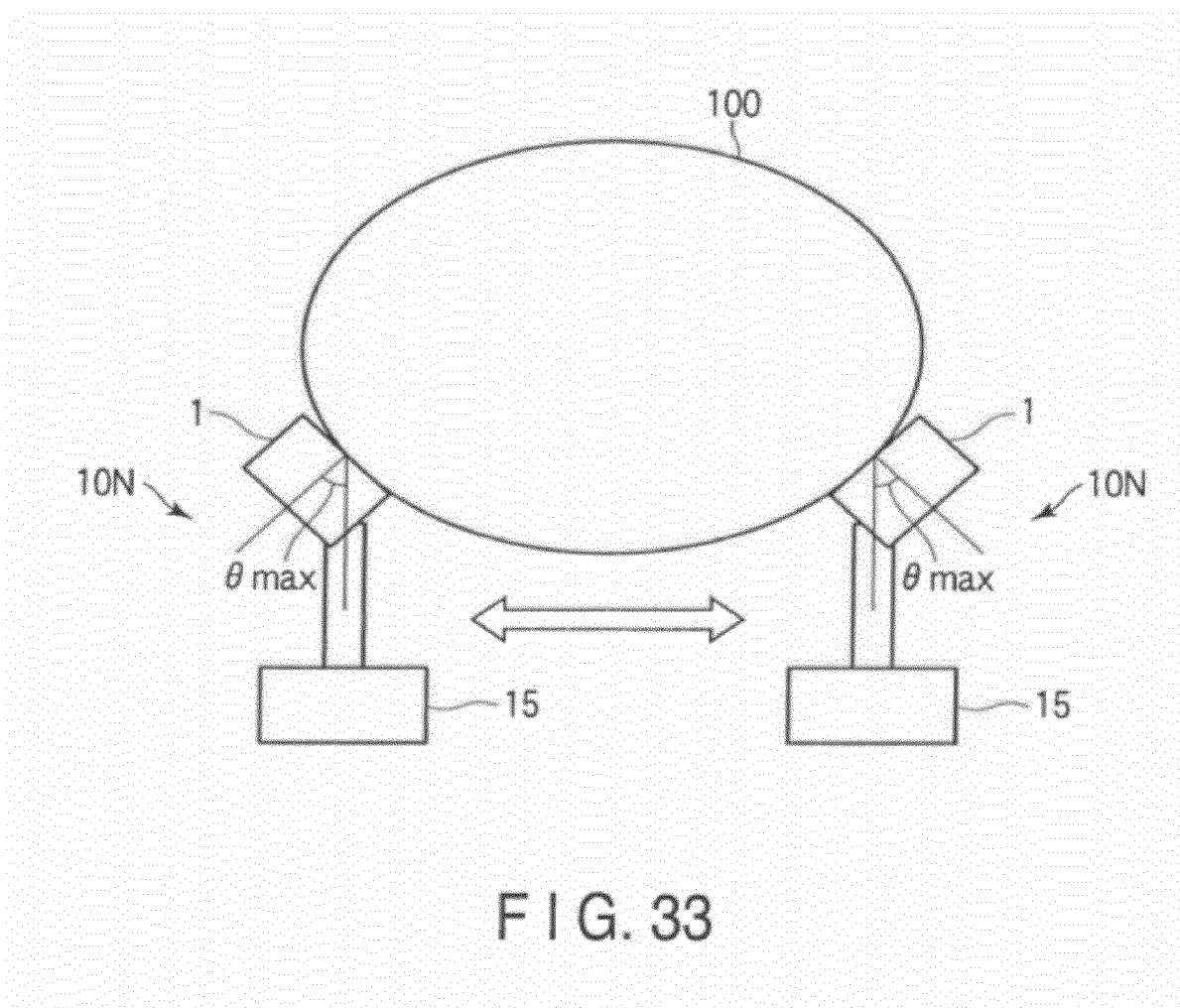
F I G. 33

COPYING APPARATUS

CROSS REFERENCE TO RELATED APPLICATIONS

This is a Continuation Application of PCT Application No. PCT/JP2008/068898, filed Oct. 17, 2008, which was published under PCT Article 21(2) in Japanese.

This application is based upon and claims the benefit of priority from prior Japanese Patent Applications No. 2007-272981, filed Oct. 19, 2007; and No. 2008-218386, filed Aug. 27, 2008, the entire contents of both of which are incorporated herein by reference.

BACKGROUND OF THE INVENTION

1. Field of the Invention

The present invention relates to a copying apparatus that copies a shape of a workpiece.

2. Description of the Related Art

In general, in the field of, e.g., inspection, measurement, or machining, a copying apparatus which copies a surface is used. For example, there is provided an ultrasonic flaw detection apparatus which is moved up and down along a surface shape of a dummy sample to thereby move up and down along a surface shape of a sample when the dummy sample that simulates the surface shape of the sample is provided (see, e.g., Jpn. Pat. Appln. KOKAI Publication No. 6-242087).

However, the above-described copying apparatus must grasp a shape of a target workpiece in advance, and preparation for a part of each workpiece to be copied must be made. Therefore, in such a copying apparatus, since a part to be copied is dependent on a shape of a workpiece, the workpiece cannot be freely changed.

BRIEF SUMMARY OF THE INVENTION

It is an object of the present invention to provide a copying apparatus having a high adaptability with respect to a shape of a workpiece.

According to an aspect of the present invention, there is provided a copying apparatus that copies a workpiece, comprising: a shoe that comes into contact with a portion of the workpiece to be copied; and a first swiveling unit that swivels with the shoe in an arc pattern around a point, as a swiveling center, on a plane where the shoe comes into contact with the portion of the workpiece to be copied.

BRIEF DESCRIPTION OF THE SEVERAL VIEWS OF THE DRAWING

FIG. 1 is a front view showing a configuration of a copying apparatus according to a first embodiment of the present invention;

FIG. 4 is a block diagram showing a copying operation of the copying apparatus according to the first embodiment of the present invention;

FIG. 8A is a front view showing a configuration of a copying apparatus according to a fourth embodiment of the present invention;

FIG. 12B is a state diagram showing a state where a sensor of the copying apparatus according to the fifth embodiment of the present invention has detected no workpiece;

FIG. 12C is a state diagram showing a state when the copying apparatus according to the fifth embodiment of the present invention is passing an end of a workpiece;

FIG. 18A is a state diagram showing a state before a copying apparatus according to a ninth embodiment of the present invention copies a workpiece;

FIG. 19 is a front view showing a configuration of a copying apparatus according to a 10th embodiment of the present invention;

FIG. 23C is a state diagram showing a state when the copying apparatus according to the 11th embodiment of the present invention is passing the end portion of the workpiece;

FIG. 29 is a front view showing a configuration of a copying apparatus according to a 14th embodiment of the present invention;

FIG. 33 is a schematic view showing a copying operation state for a cylindrical workpiece performed by the copying apparatus according to the 15th embodiment of the present invention;

DETAILED DESCRIPTION OF THE INVENTION

Embodiments according to the present invention will now be described hereinafter with reference to the accompanying drawings.

First Embodiment

Figure 2:
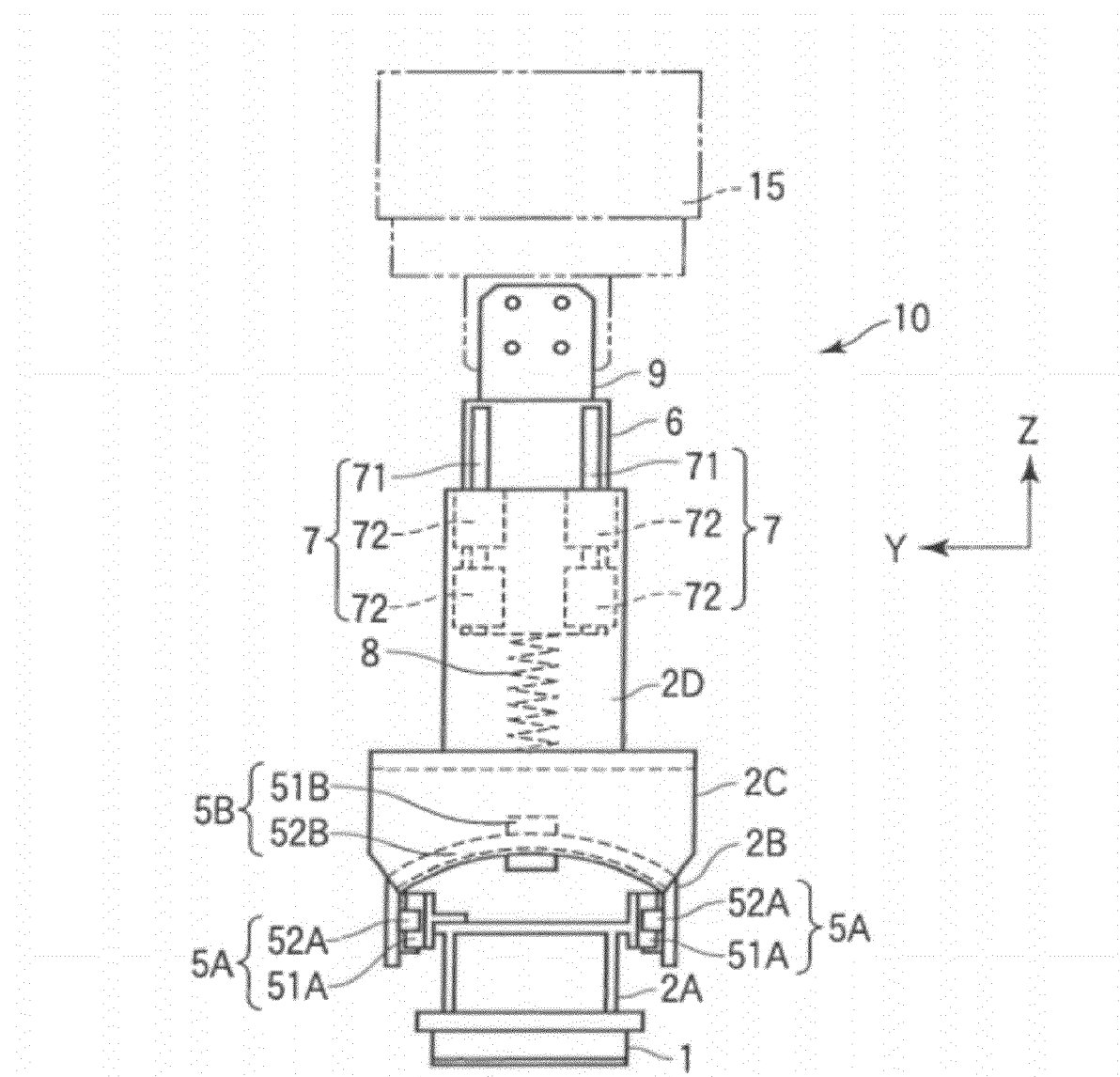
FIG. 2 is a side view showing a configuration of the copying apparatus according to the first embodiment of the present invention.

FIG. 1 is a front view showing a configuration of a copying apparatus according to a first embodiment of the present invention. FIG. 2 is a side view showing a configuration of the copying apparatus 10 according to this embodiment. An X axis, a Y axis, and a Z axis shown in the drawings are axes orthogonal to each other. It is to be noted that like reference numerals denote the same parts to omitted a detailed explanation thereof and different parts will be mainly described below. In subsequent embodiments, a tautological explanation will be likewise omitted.

The copying apparatus 10 includes a shoe 1, frames 2A, 2B, 2C, and 2D, arched slide guides 5A and 5B, a slide portion 6, translation guides 7, an elastic body 8, and a fixing portion 9. The copying apparatus 10 is controlled by a feeder apparatus 15 to copy a surface of a workpiece 100.

The shoe 1 is a portion that is brought into contact with the workpiece 100 to be copied. The shoe 1 is disposed to the frame 2A.

The respective arched slide guides 5A are disposed to hold both sides of the frame 2A. The arched slide guide 5A includes a block 51A and a rail 52A. The rail 52A has an arched shape. The block 51A is disposed to the frame 2A. The rail 52A is disposed to the frame 2B.

The frame 2A can be moved to relatively swivel with respect to the frame 2B by the arched slide guides 5A. A central axis of swiveling of the frame 2A by the arched slide guides 5A is present on a plane where the shoe 1 comes into contact with the workpiece 100.

The arched slide guides 5B are provided to be orthogonal to the arched slide guides 5A. That is, a plane including an arc that is slid by each arched slide guide 5A is orthogonal to a plane including an arc that is slid by each arched slide guide 5B.

The respective arched slide guides 5B are disposed to hold both sides of the frame 2B. The arched slide guide 5B includes a block 51B and a rail 52B. The rail 52B has an arched shape. The block 51B is disposed to the frame 2B. The rail 52B is disposed to the frame 2C.

The frame 2B can be moved to relatively swivel with respect to the frame 2C by the arched slide guides 5B. A central axis of swiveling of the frame 2B by the arched slide guides 5B is present on a plane where the shoe 1 comes into contact with the workpiece 100.

The frame 2D is provided above the frame 2C. The frame 2D supports movement of the slide portion 6 in an up-and-down direction (a Z axis direction). The fixing portion 9 is provided at an upper portion of the frame 2D. The fixing portion 9 is held by the feeder apparatus 15 to move the copying apparatus 10 in the respective directions.

The four translation guides 7 are provided to support four corners of the slide portion 6. Specifically, two translation guides 7 are disposed on each of both sides of the slide portion 6. The two translation guides 7 disposed on each single side of the slide portion 6 are attached to be placed at both ends. One translation guide 7 includes a rail 71 and two blocks 72. The rail 71 is fixed to the slide portion 6. The blocks 72 are fixed to the frame 2D. The two blocks 72 are provided to be divided in the vertical direction in such a manner that they support the movable slide portion 6 that is movable in the vertical direction. Based on this configuration, the slide portion 6 can move up and down along each rail 71.

The elastic body 8 is provided below the slide portion 6. The elastic body 8 is, e.g., a spring. The elastic body 8 expands and contracts in a direction along which the slide portion 6 can slide (i.e., the up-and-down direction) by the translation guides 7. The elastic body 8 buffers a pressing force of the feeder apparatus 15 with respect to the workpiece 100. As a result, the copying apparatus 10 does not apply an excessive pressing force to the workpiece 100. The elastic body 8 tolerates displacement in the up-and-down direction when copying the workpiece 100.

A central point O will now be described.

Figure 3:
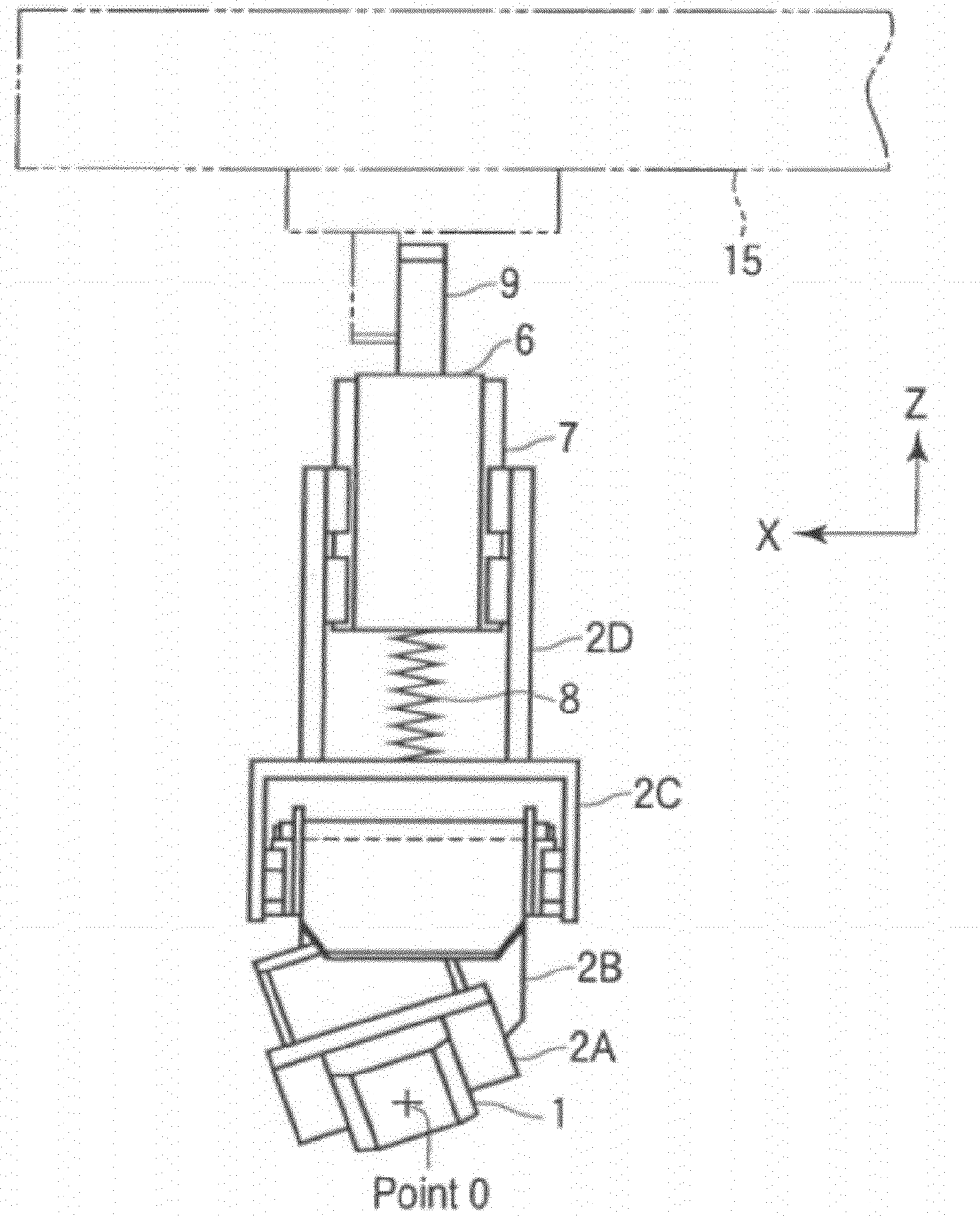
FIG. 3 is a block diagram showing movement of a shoe in the copying apparatus according to the first embodiment of the present invention.

FIG. 3 is a block diagram showing movement of the shoe 1 of the copying apparatus 10 according to this embodiment. In the copying apparatus 10 depicted in FIG. 3, the frame 2B is inclined toward a front side in a direction along which the drawing is seen (a Y axis direction), and the frame 2A is inclined toward a right-hand side in a direction along which the drawing in the X axis direction is seen. That is, in the copying apparatus 10, the plane where the shoe 1 and the workpiece 100 are in contact with each other is seen.

The central point O is a point on the central axis of swiveling of the frame 2A effected by the arched slide guides 5A, and it is also a point on the central axis of swiveling of the frame 2B effected by the arched slide guides 5B. Therefore, the central point O is an intersection of the central axes of the two arched slide guides 5A and 5B. Therefore, the center of swiveling of the two arched slide guides is present at one point alone on a workpiece surface where the shoe 1 comes into contact with the workpiece 100. As a result, a position of the central point O does not vary depending on inclination of the shoe 1.

An operation of the copying apparatus 10 will now be described with reference to FIG. 4.

The feeder apparatus 15 moves the copying apparatus 10 in a direction F1 (a downward direction) of the workpiece 100. The shoe 1 of the copying apparatus 10 comes into contact with the workpiece 100. Further, when a downward force is applied to the slide portion 6 of the copying apparatus 10, the elastic body 8 contracts. As a result, the shoe 1 applies a pressing force to the workpiece 100.

This pressing force is turned to a moment force when the shoe 1 having a width comes into contact with the workpiece 100. This moment force swivels the two arched slide guides 5A and 5B with the surface of the workpiece 100 being used as a swiveling center. With this swiveling motion, a direction of the shoe 1 is changed to a normal line direction of a curved surface of the workpiece 100. At this time, the central point O on the shoe 1 is placed at the center of the contact surface with respect to the workpiece 100.

According to this embodiment, the arched slide guides 5A and 5B are orthogonally provided. The shoe 1 three-dimensionally moves with one point on the surface of the workpiece 100 being used as a rotation center based on combinations of swiveling motions of these two arched slide guides 5A and 5B. As a result, the copying apparatus 10 can copy a three-dimensional curved surface of the workpiece 100.

The arched slide guides 5A and 5B swivel when the moment force is produced due to contact of the workpiece 100 and the shoe 1. As a result, the shoe 1 can be directed toward the normal line direction of the surface of the workpiece 100.

The copying apparatus 10 can copy the curved surface of the workpiece 100 without requiring complicated control or operations from the outside. Therefore, the copying apparatus 10 can copy the three-dimensional curved surface of the workpiece 100 by the feeder apparatus 15 performing an operation in an advancing direction along which copying is performed, an index operation, and an operation in a pressing direction. That is, the copying apparatus 10 can copy the three-dimensional curved surface of the workpiece 100 by the feeder apparatus 15 just giving movements in three linear axes, i.e., the X axis, the Y axis, and the Z axis to the copying apparatus 10.

Since the central point O as the swiveling center of the shoe 1 is provided on the workpiece surface, a contact point is one point on the workpiece surface even if the shoe 1 is inclined due to copying the workpiece surface. That is, the point where the shoe 1 is in contact with the workpiece 100 does not move from the swiveling center. Therefore, a point to be copied (a contact position) is not displaced within the X-Y plane. Accordingly, control over the copying apparatus 10 by the feeder apparatus 15 can be facilitated since the contact point does not have to be subjected to positional correction.

Since the elastic body 8 is provided, the copying apparatus 10 can tolerate some high irregularities on the surface of the workpiece 100 in the up-and-down direction, thereby copying the workpiece 100. As a result, even if the surface of the workpiece 100 is complicated, the copying apparatus 10 can copy the workpiece 100 without requiring fine control in the Z direction in the drawing performed by the feeder apparatus 15.

Therefore, the copying apparatus 10 can copy a workpiece having a curved surface (including a curved plate) or a flat plate shape without providing a plurality of control axes other than those for liner motions to specially perform complicated control.

Second Embodiment

Figure 5:
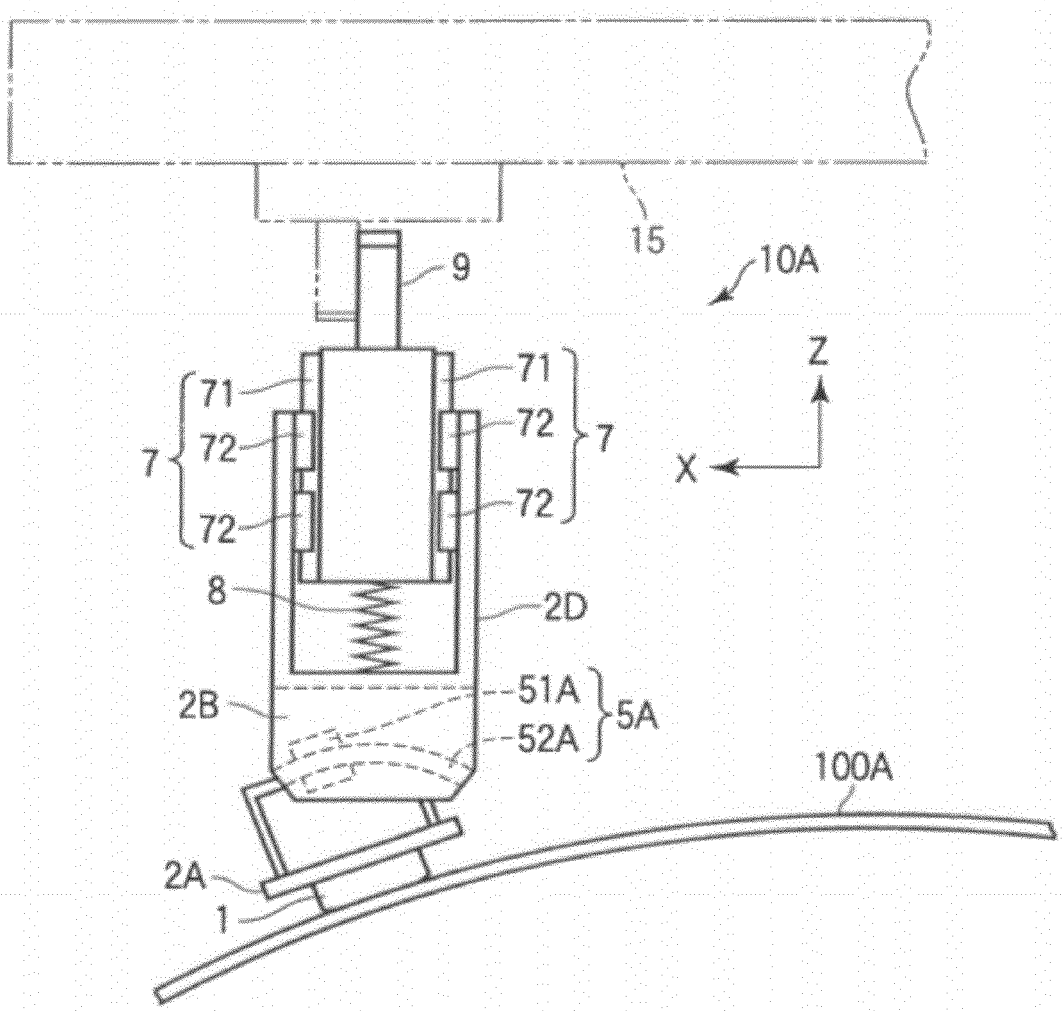
FIG. 5 is a block diagram showing a configuration of a copying apparatus according to a second embodiment of the present invention.

FIG. 5 is a block diagram showing a configuration of a copying apparatus 10A according to a second embodiment of the present invention.

The copying apparatus 10A has a configuration where the frame 2C and the arched slide guides 5B are eliminated and the frame 2B is directly disposed to the frame 2D in the copying apparatus 10 according to the first embodiment depicted in FIG. 1. Any other points are the same as those of the copying apparatus 10.

An operation of the copying apparatus 10A will now be described.

A workpiece 100A is a curved plate which has an arched shape obtained by bending a flat plate in one direction. Therefore, a normal line at a contact point of a shoe 1 and the workpiece 100A changes only in an X-Z plane in the drawing.

The copying apparatus 10A is placed on a surface of the workpiece 100A in such a manner that this X-Z plane becomes parallel to a plane including an arc along which arched slide guides 5A slide. That is, the copying apparatus 10A is set up on the workpiece 100A in such a manner that a direction in which the arched slide guides 5A can swivel is set on the X-Z plane.

A control method for the copying apparatus 10A performed by a feeder apparatus 15 is the same as the copying apparatus 10 according to the first embodiment except that the copying apparatus 10A is moved in one direction.

According to this embodiment, in case of a workpiece 100A that the number of direction along which a normal line varies is one, the copying apparatus 10A having a simple structure can copy the workpiece 100A. Therefore, according to the control method for the copying apparatus 10A performed by the feeder apparatus 15, executing simple control in the X, Y, and Z directions enables copying the workpiece 100A.

Third Embodiment

Figure 6:
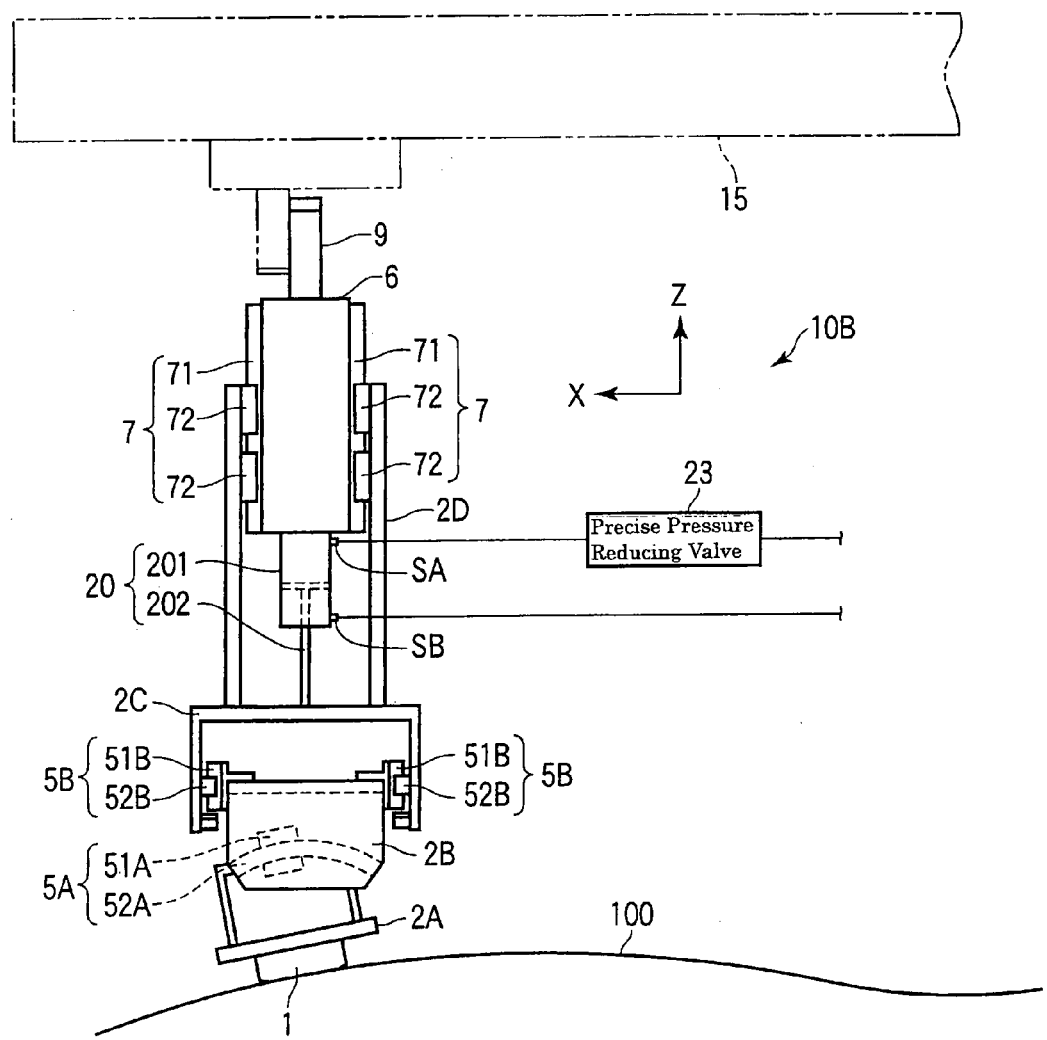
FIG. 6 is a block diagram showing a configuration of a copying apparatus according to a third embodiment of the present invention.

FIG. 6 is a block diagram showing a configuration of a copying apparatus 10B according to a third embodiment of the present invention.

The copying apparatus 10B has a configuration where an air cylinder 20 and a precise pressure reducing valve 23 are provided in place of the elastic body 8 in the copying apparatus 10 according to the first embodiment depicted in FIG. 1. Any other points are the same as those in the copying apparatus 10.

The air cylinder 20 is provided below a slide portion 6. The air cylinder 20 is expanded or contracted in a direction along which the slide portion 6 can slide (i.e., an up-and-down direction) by translation guides 7.

The air cylinder 20 is an elastic element that buffers a pressing stroke of the copying apparatus 10B. The copying apparatus 10B has a buffering function when a workpiece 100 is pressed owing to the elastic element of the air cylinder 20. As a result, the copying apparatus 10B does not apply an excessive pressing force to the workpiece 100. The air cylinder 20 tolerates displacement in the up-and-down direction when copying the workpiece 100.

The air cylinder 20 includes a cylinder 201 and a rod 202. The cylinder 201 is fixed to the slide portion 6. The rod 202 is fixed to the frame 2C.

The precise pressure reducing valve 23 controls an air pressure in the air cylinder 20. The precise pressure reducing valve 23 is installed to control an air pressure on an 5A side (an upper side) of the air cylinder 20. The precise pressure reducing valve 23 has a relief function. The precise pressure reducing valve 23 is arranged in a pneumatic circuit between the air cylinder 20 and a supply source (a primary side) of compressed air. Here, it is assumed that devices, e.g., an electromagnetic valve, a filter, and others are arranged in the pneumatic circuit as required.

An operation of the copying apparatus 10B will now be described.

The copying apparatus 10B is pressed against the workpiece 100 by the feeder apparatus 15. At this time, the air cylinder 20 is contracted. A force that presses the workpiece 100 is determined based on a pressure of compressed air provided by contraction of the air cylinder 20 and a piston diameter of the air cylinder 20.

According to this embodiment, the following functions and effects can be obtained in addition to the functions and effect according to the first embodiment.

The copying apparatus 10B uses the air cylinder 20 and the precise pressure reducing valve 23 depicted in relation to the pneumatic circuit. Therefore, a secondary pressure on the air cylinder side can be maintained constant. As a result, a pressing force (a contact force) of the copying apparatus 10B can be set to an appropriate fixed value. The copying apparatus 10B can obtain a constantly appropriate contact force (the pressing force) by keeping the pressing force constant.

For example, a conventional general copying apparatus often uses a coil spring as an elastic body of a buffer unit. In this case, a long buffer stroke (a stroke for copying) cannot be taken in some cases. That is because a pressure force of the coil spring varies depending on a stroke as described in the Hooke's law and the stroke is also limited depending on a length of the coil spring itself. In case of the copying apparatus 10B, when a particularly long buffer stroke (a stroke for copying) is required, using the slide portion 6 or the translation guides 7 having a long stroke and the air cylinder 20 can suffice. Further, the pressing force is not changed irrespective of the long stroke.

Further, just adjusting the precise pressure reducing valve 23 facilitates adjusting the pressing force (the contact force) of the copying apparatus. That is, a spring component does not have to be replaced every time the pressing force is adjusted as different from the buffer portion using the coil spring.

Fourth Embodiment

Figure 8B:
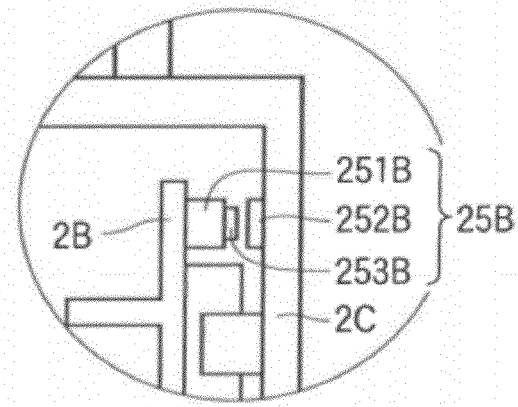
FIG. 8B is an enlarged view showing a state before a brake of the copying apparatus according to the fourth embodiment of the present invention is operated.
Figure 8C:
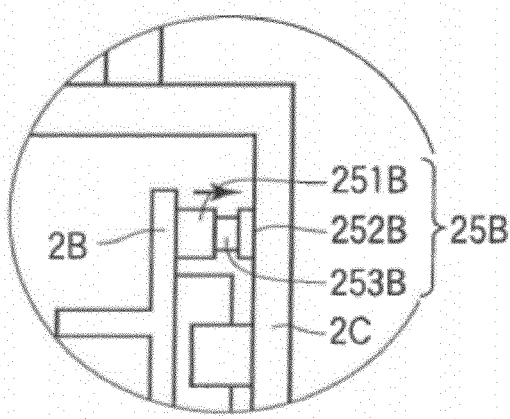
FIG. 8C is an enlarged view showing a state before the brake of the copying apparatus according to the fourth embodiment of the present invention is operated.
Figure 9:
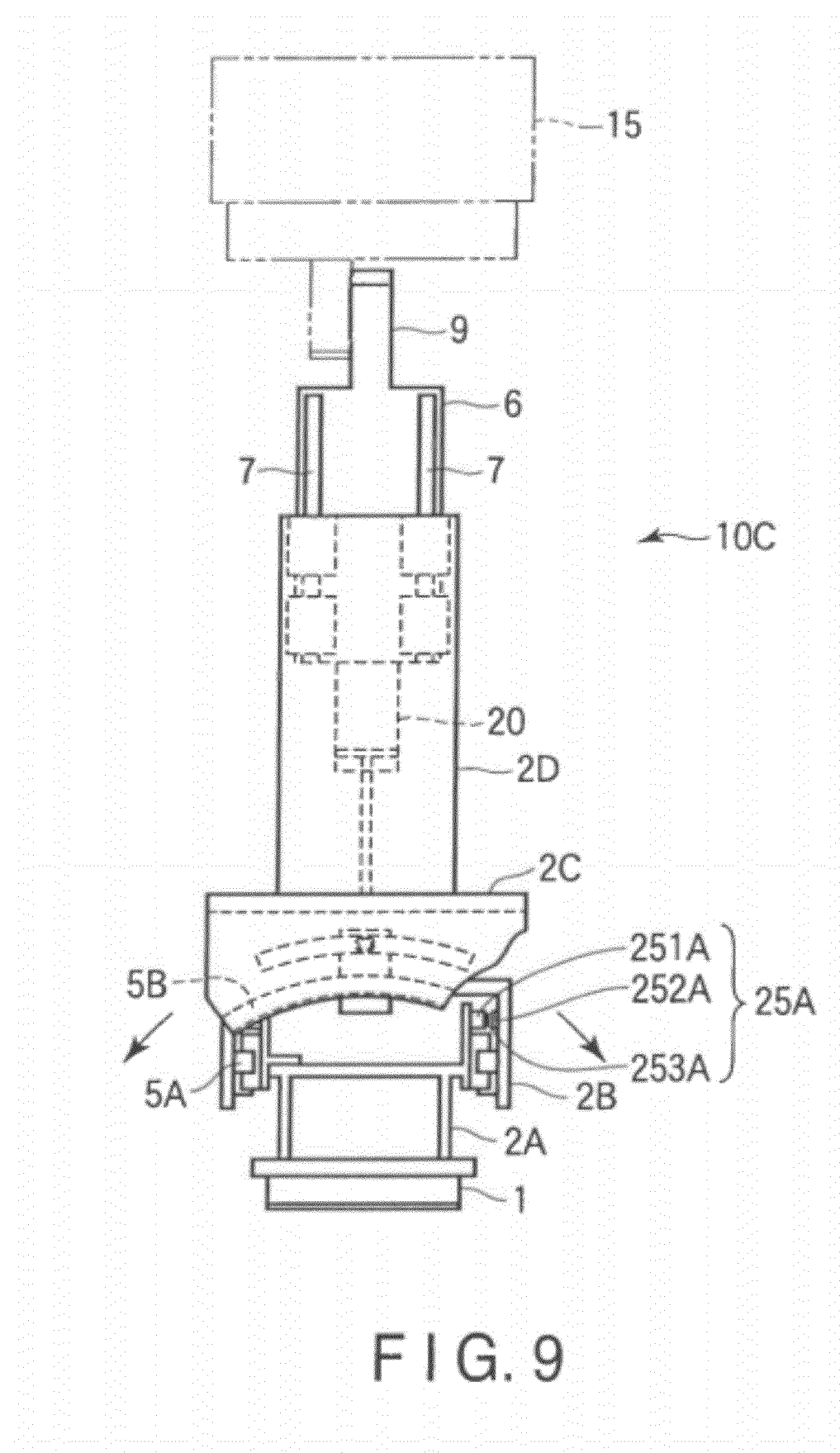
FIG. 9 is a side view showing a configuration of the copying apparatus according to the fourth embodiment of the present invention.

Each of FIGS. 8A, 8B, and 8C is a front view showing a configuration of a copying apparatus 10C according to a fourth embodiment of the present invention. FIG. 9 is a side view showing a configuration of the copying apparatus 10C according to this embodiment.

The copying apparatus 10C has a structure where brakes 25A and 25B in the copying apparatus 10B according to the third embodiment depicted in FIG. 6. Any other points are the same as those in the copying apparatus 10B.

The brake 25B is a braking device that suppresses movement of arched slide guides 5B. When the brake 25B operates and a brake pad 252B presses a friction plate 253B, the movement of the arched slide guides 5B is locked.

The brake 25B includes a brake main body 251B, the brake pad 252B, and the friction plate 253B.

The brake pad 252B is incorporated in the brake main body 251B. The brake main body 251B is fixed to a frame 2B. The friction plate 253B is fixed to a frame 2C. Therefore, the brake main body 251B and the friction plate 253B relatively make movements.

The brake 25A is a braking device that suppresses movement of arched slide guides 5A. When the brake 25A operates and a brake pad 252A presses a friction plate 253A, the movement of the arched slide guides 5A is locked.

The brake 25A includes a brake main body 251A, the brake pad 252A, and the friction plate 253A.

The brake pad 252A is incorporated in the brake main body 251A. The brake main body 251A is fixed to the frame 2A. The friction plate 253A is fixed to the frame 2B. Therefore, the brake main body 251A and the friction plate 253A relatively make movements.

An operation of the brake 25B will now be described with reference to FIGS. 8A to 8C. FIG. 8B is an enlarged view showing a state before the brake 25B operates. FIG. 8C is an enlarged view showing a state after the brake 25B operates. It is to be noted that an operation of the brake 25A is the same as that of the brake 25B, thereby omitting an explanation thereof.

Here, the brake 25B is controlled by a non-illustrated control device.

The control device outputs an operation command to the brake 25B.

Upon receiving the operation command from the control device, the main body of the brake 251B pushes out the brake pad 252B by using an air pressure.

The pushed-out brake pad 252B comes into contact with the friction plate 253B.

When the brake pad 252B comes into contact with the friction plate 253B, movement of the arched slide guides 5B coupled with the fiction plate 253B on the frame 2C is held.

A degree of freedom of the copying apparatus 10C can be restricted by the series of operations.

An operation of copying the workpiece 100 by the copying apparatus 10C will now be described with reference to FIGS.

10A to 10C. Here, in this workpiece 100, a last portion which is subjected to a copying operation is an end portion.

Figure 10A:
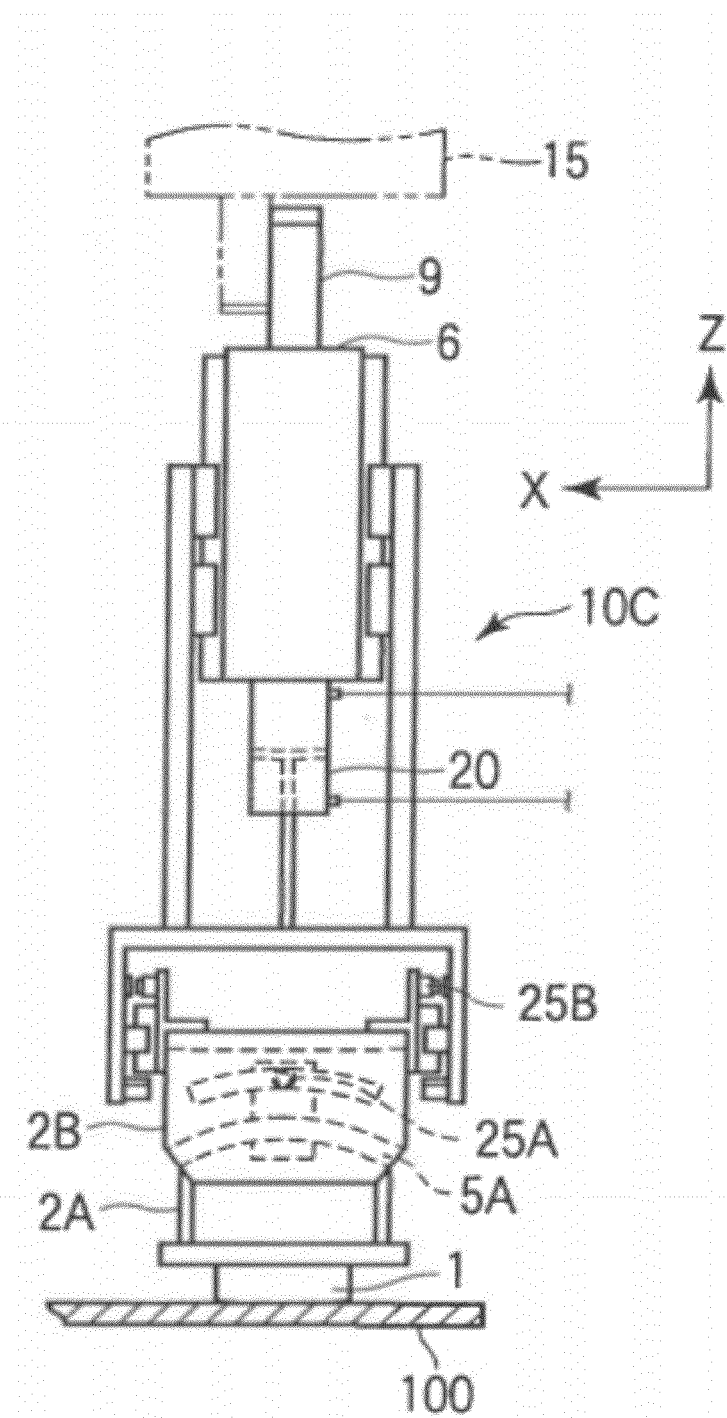
FIG. 10A is a state diagram showing a state during a regular operation of the copying apparatus according to the fourth embodiment of the present invention.
Figure 10B:
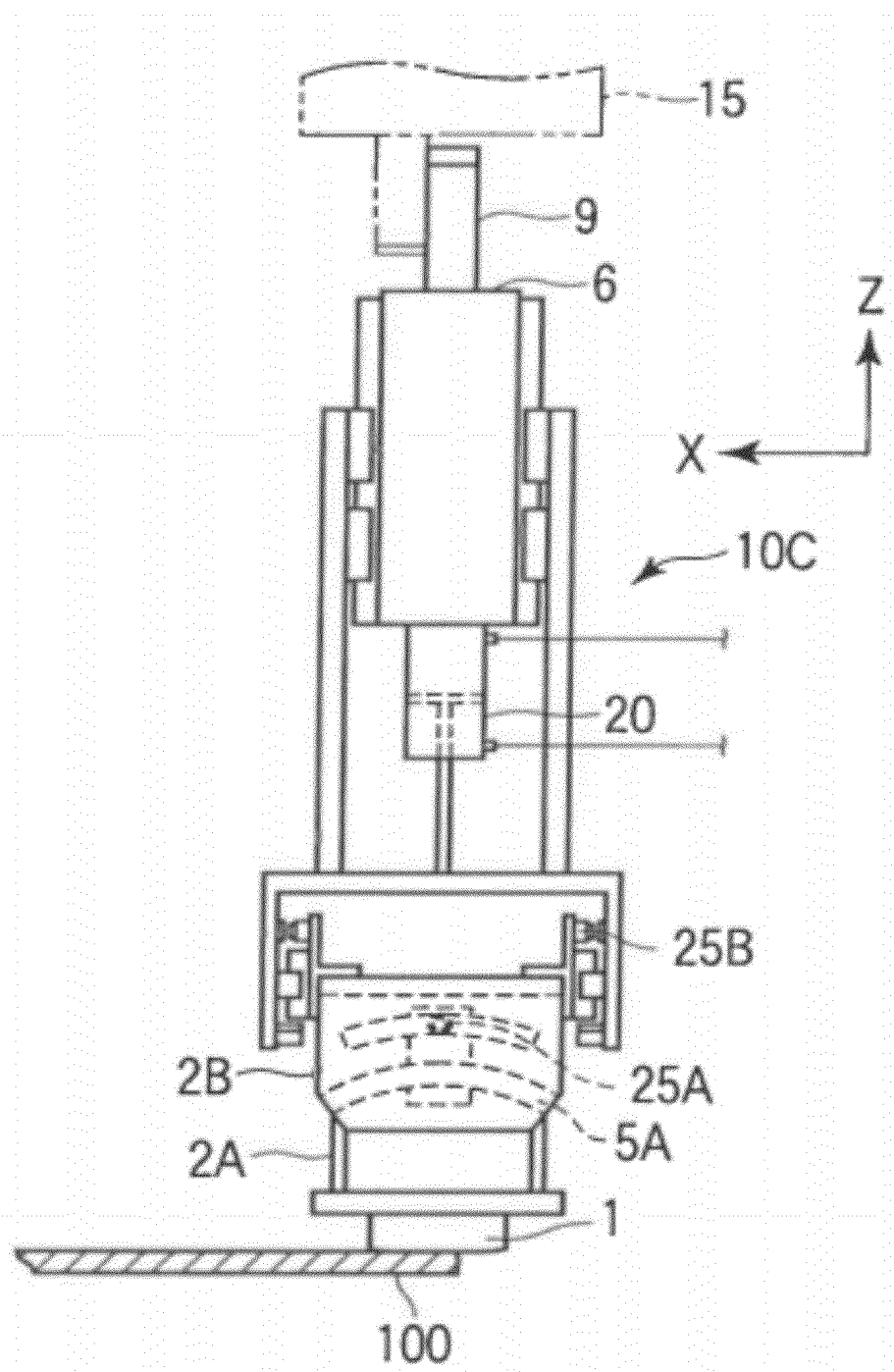
FIG. 10B is a state diagram showing a state immediately before the copying apparatus according to the fourth embodiment of the present invention reaches an end of a workpiece.
Figure 10C:
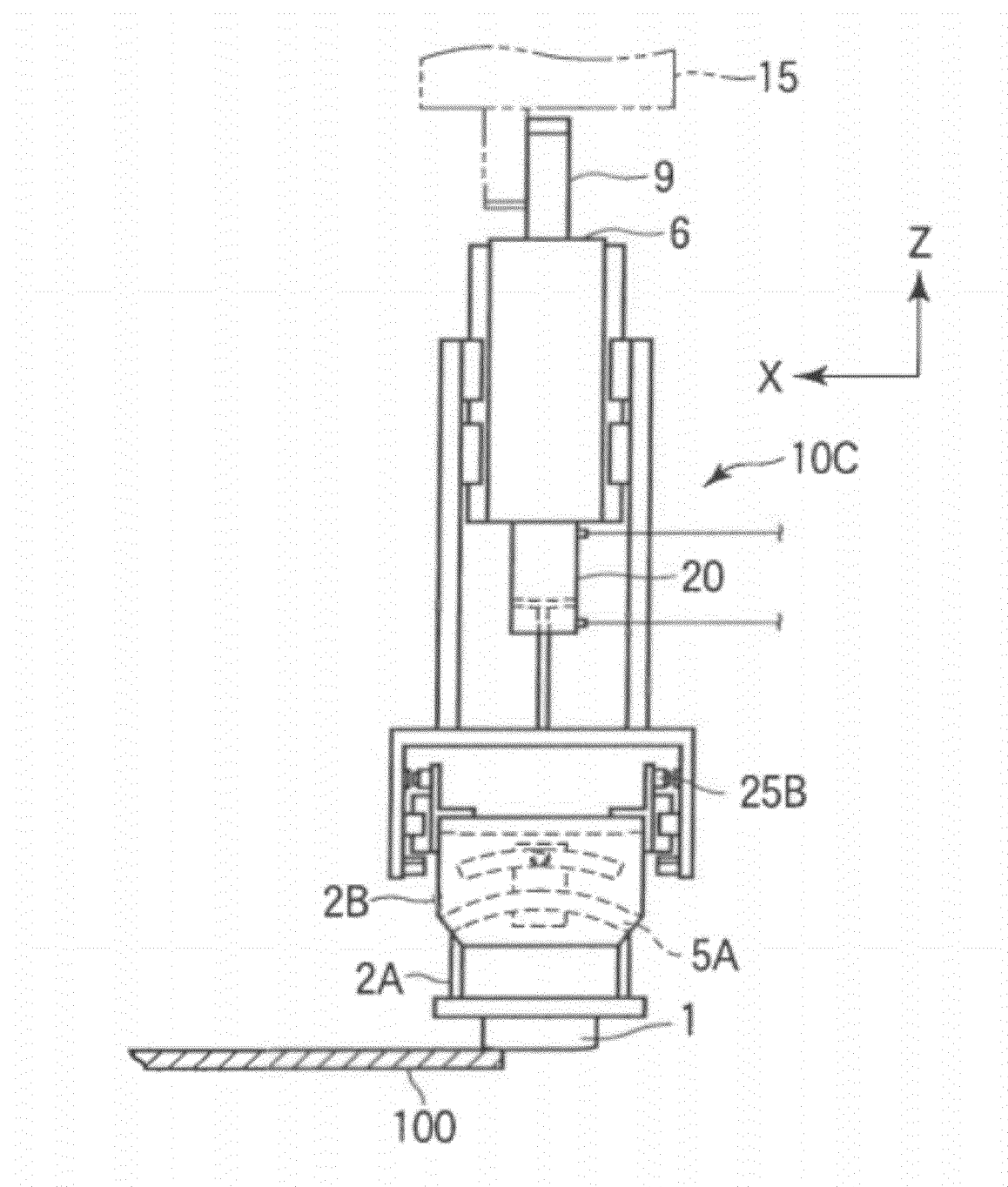
FIG. 10C is a state diagram showing a state where the copying apparatus according to the fourth embodiment of the present invention is passing the end of the workpiece.

Each of FIGS. 10A, 10B, and 10C is a state diagram showing a state during an operation of the copying apparatus 10C according to this embodiment. FIG. 10A is a state diagram showing a state during a regular operation of the copying apparatus 10C. FIG. 10B is a state diagram showing a state immediately before the copying apparatus 10C reaches an end of the workpiece 100. FIG. 10C is a state diagram showing a state when the copying apparatus 10C is passing the end of the workpiece 100. The copying operation for the workpiece 100 by the copying apparatus 10C is performed in order of FIG. 10A, FIG. 10B, and FIG. 10C.

During a regular operation (i.e., the state shown in FIG. 10A), the arched slide guides 5A and 5B freely swivel, and the shoe 1 copies the workpiece 100.

In the state shown in FIG. 10B, the brake 25A is immediately before or immediately after an operation.

In the state depicted in FIG. 10C, the brake 25A is operating. Therefore, the movement of the arched slide guides 5A is locked. Therefore, the shoe 1 is not inclined even when the apparatus is passing a discontinuous portion of the workpiece 100. As a result, the copying apparatus 10C can perform the appropriately stable copying operation to the end portion of the workpiece 100.

Here, although the description has been mainly given as to the operation of the brake 25A, the operation of the brake 25B is the same.

Figure 11:
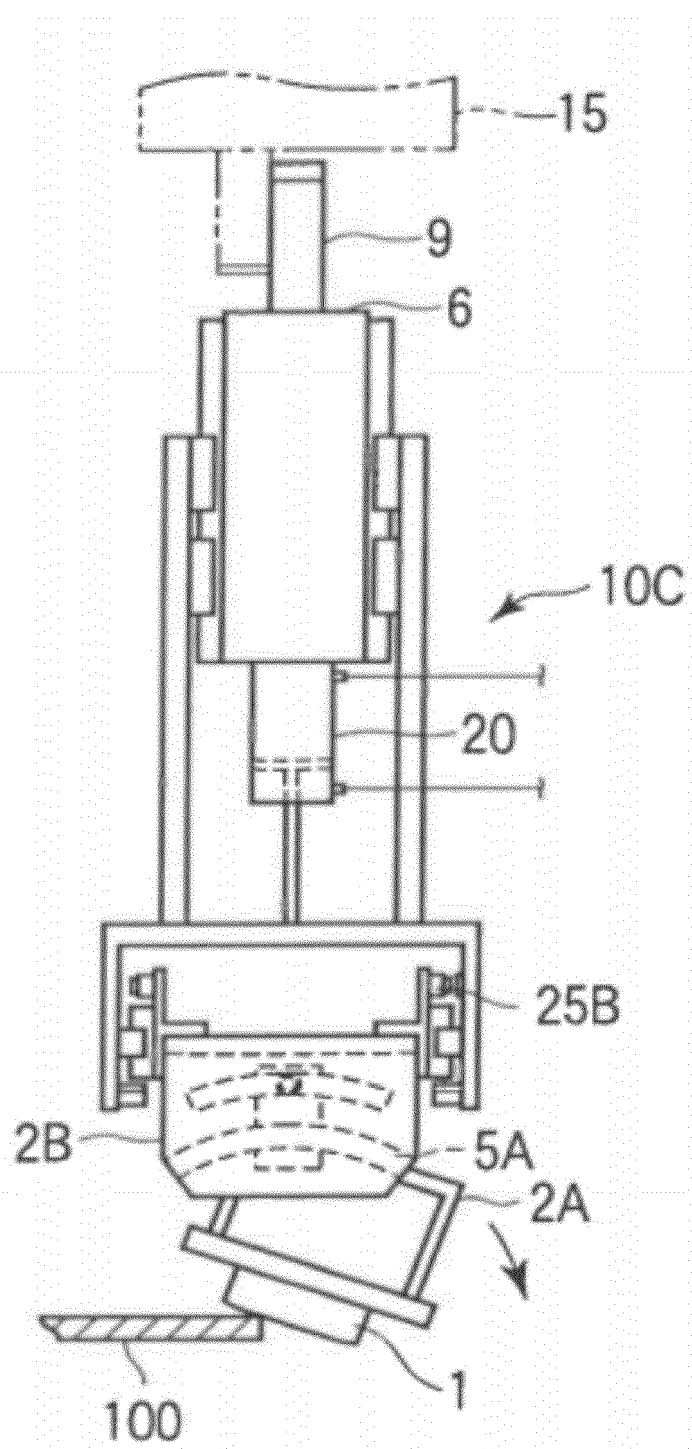
FIG. 11 is a state diagram showing a state where a brake of the copying apparatus according to the fourth embodiment of the present invention is not operated.

It is to be noted that, when the brake 25A of the copying apparatus 10C is not operated, the shoe 1 is greatly inclined as shown in FIG. 11. That is because the copying apparatus 10C is constantly appressed against to the workpiece 100 and the arched slide guides 5A freely swivel.

According to this embodiment, the following functions and effects can be obtained in addition to the functions and effects obtained by the third embodiment.

Even when the copying apparatus 10C passes a discontinuous (or end) portion of the workpiece 100, a posture of the copying apparatus 10C is held by the brakes 25A and 25B. As a result, the copying apparatus 10C can pass the discontinuous portion (or the end portion) of the workpiece 100 without collapsing the posture.

Therefore, providing the brakes 25A and 25B as braking devices enables restricting a degree of freedom of the copying apparatus 10C. As a result, the copying apparatus 10C can appropriately travel along, e.g., an end portion or an edge of the workpiece, or an opening portion of a workpiece surface.

Fifth Embodiment

Figure 12A:
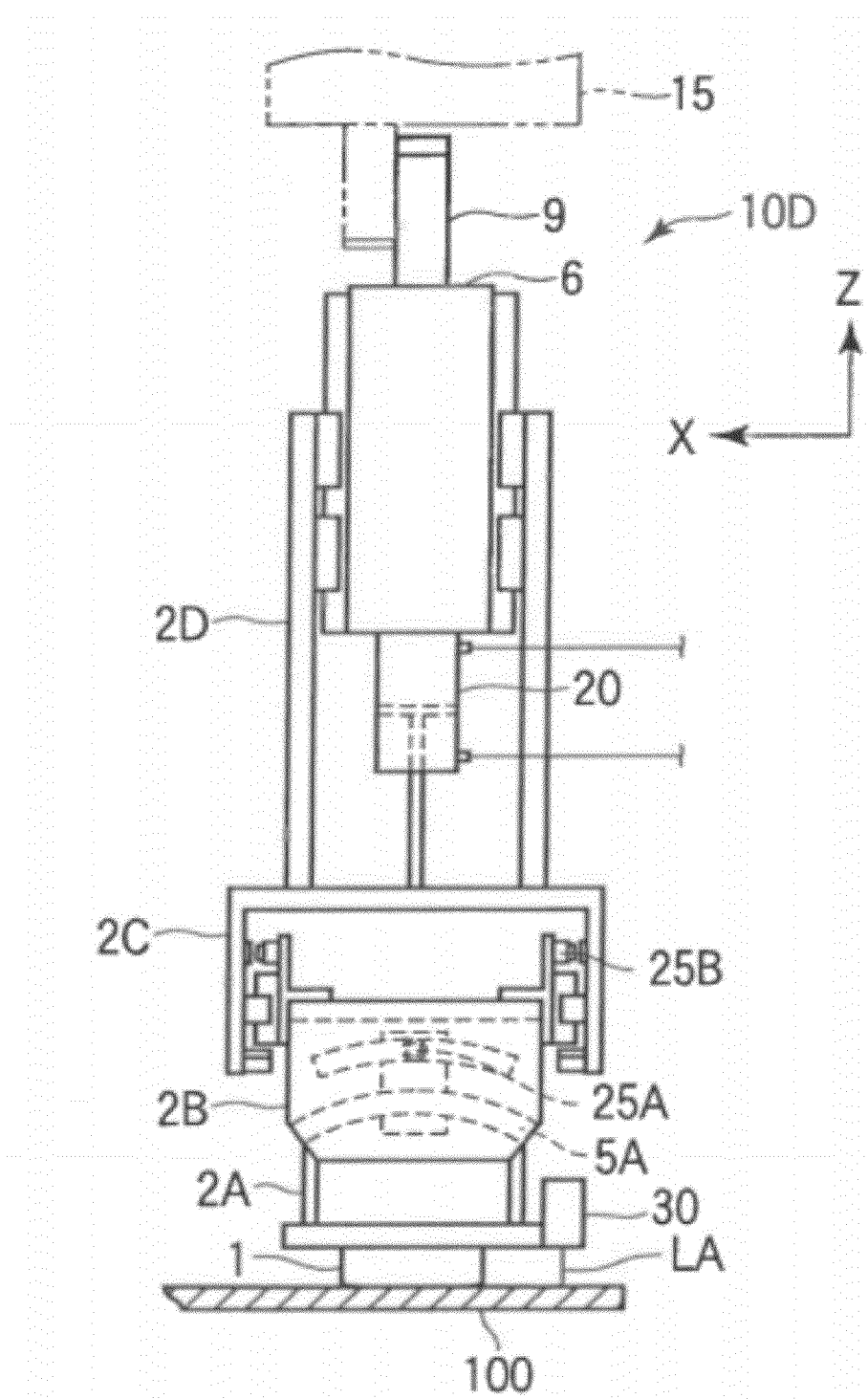
FIG. 12A is a state diagram showing a state during a regular operation of a copying apparatus according to a fifth embodiment of the present invention.

Each of FIGS. 12A, 12B, and 12C is a state diagram showing a state during an operation of a copying apparatus 10D according to a fifth embodiment of the present invention. FIG. 12A is a state diagram showing a state during a regular operation of the copying apparatus 10D. FIG. 12B is a state diagram showing a state where a sensor 30 of the copying apparatus 10D detects absence of a workpiece 100. FIG. 12C is a state diagram showing a state when the copying apparatus 10D is passing an end of the workpiece 100. A copying operation for the workpiece 100 by the copying apparatus 10D is performed in order of FIG. 12A, FIG. 12B, and FIG. 12C.

The copying apparatus 10D has a configuration where a sensor 30 is provided on a traveling direction side for the copying operation apart from a shoe 1 in the copying apparatus 10C according to the fourth embodiment depicted in FIGS. 10A to 10C. Any other points are the same as those in the copying apparatus 10C.

The sensor 30 detects an end portion or an edge of the workpiece 100. When an object cannot be detected in a set range of a given distance, the sensor 30 detects a state where the workpiece 100 as a measurement target is not present. The sensor 30 is, e.g., a laser type non-contact sensor. The sensor 30 outputs a laser beam LA to detect an end portion or an edge of the workpiece 100.

An operation of the copying apparatus 10D will now be described.

In a regular mode, as shown in FIG. 12A, arched slide guides 5A and 5B freely swivel, and a shoe 1 copies the workpiece 100.

A non-illustrated control device first judges a detection result from the sensor 30.

Upon receiving a signal indicative of absence of the workpiece 100 in the traveling direction of the copying apparatus 10D (i.e., the state shown in FIG. 12B) from the sensor 30, this control device outputs a signal that is used to operate a brake 25A or a brake 25B. During the operation shown in FIG. 12A to 12C, the brake 25A is operated.

The copying apparatus 10D operates the brake 25A or the brake 25B based on a signal from the control device. As a result, the copying apparatus 10D holds a posture of the copying apparatus 10D immediately before passing a part near an end portion or an edge of the workpiece. A timing for operating the braking device, e.g., the brake 25A or the brake 25B is associated with a speed in the traveling direction of the copying apparatus or a disposing position of the sensor 30.

As shown in FIG. 12C, since a posture of the copying apparatus 10D is held, the posture of the copying apparatus does not vary even though it passes an end portion or an edge of the workpiece 100.

According to this embodiment, in addition to the functions and effects according to the fourth embodiment, the copying apparatus 10D can hold its posture without previously programming an operation point of the braking device with respect to the workpiece 100 as a target.

Sixth Embodiment

Figure 13:
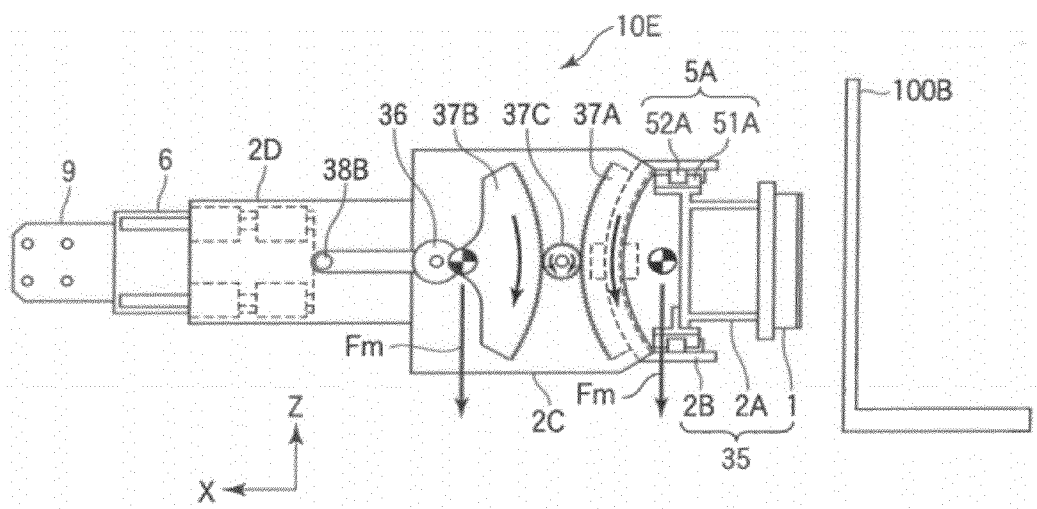
FIG. 13 is a front view showing a configuration of a copying apparatus according to a sixth embodiment of the present invention.
Figure 14:
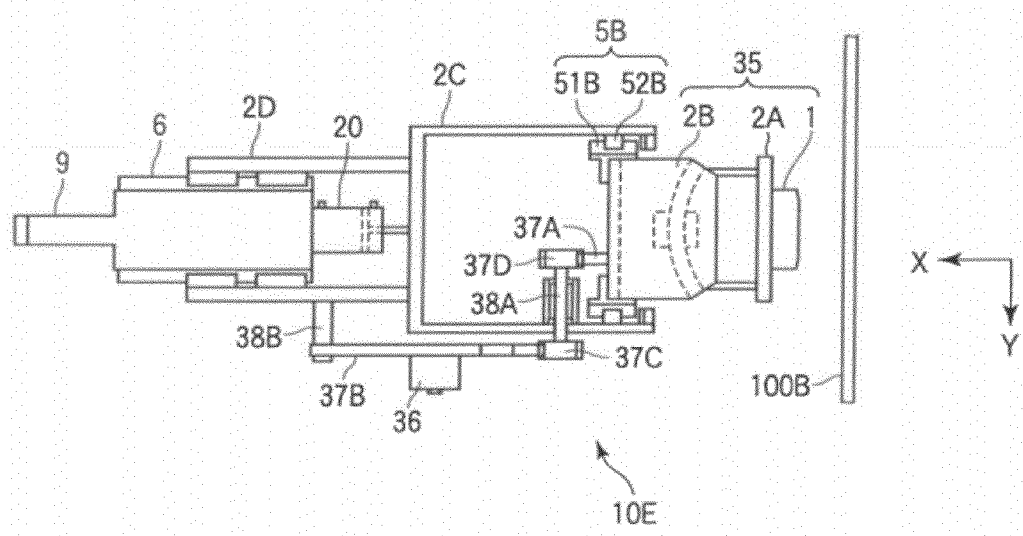
FIG. 14 is a side view showing the configuration of the copying apparatus according to the sixth embodiment of the present invention.

FIG. 13 is a front view showing a configuration of a copying apparatus 10E according to a sixth embodiment of the present invention. FIG. 14 is a side view showing the configuration of the copying apparatus 10E according to this embodiment.

The copying apparatus 10E has a structure where a counterweight 36, gears 37A, 37B, 37C, and 37D, and rotary shafts 38A and 38B are provided in the copying apparatus 10B according to the third embodiment depicted in FIG. 6. The copying apparatus 10E has the structure preferable for an application where this apparatus is used sideways. Any other points are the same as those in the copying apparatus 10B.

A workpiece 100B is a workpiece which must be copied sideways.

When the copying apparatus 10E is set up sideways, a moment force Fm acts in a direction along which a shoe 1 moves away from the workpiece 100B. That is because arched slide guides 5B freely move based on a position of gravity center of a movable portion 35 of the copying apparatus 10E. Here, the movable portion 35 is a portion (from the shoe 1 at a distal end to a frame 2B) fixed to a block 51B of each arched slide guide 5B. That is, the movable portion 35 means a portion that can move down due to a function of a gravitational force.

In the copying apparatus 10E, the counterweight 36 which corrects an influence of the moment force Fm is provided. The counterweight 36 reduces the moment force Fm in the direction along which the shoe 1 moves away from the workpiece 100B. As a weight of the counterweight 36, a weight which can reduce the moment force in the direction along which the shoe 1 moves away from the workpiece 100B as required can suffice. Therefore, this weight does not have to be definitely set.

An operation and a configuration of the copying apparatus 10E will now be described with reference to FIG. 13.

The copying apparatus 10E is set up in a horizontal direction. It is assumed that the copying apparatus 10E performs a copying operation sideways with respect to the workpiece 100B. A contact surface of the workpiece 100B may be of course a curved surface or a flat plate.

The gear 37A is fixed to the frame 2B to be movable with movement of the shoe 1.

The gear 37B and the counterweight 36 rotate on the rotary shaft 38B.

The gravitational force acts downwards with respect to the movable portion 35. Likewise, the gravitational force acts downwards with respect to the counterweight 36. Therefore, the movable portion 35 and the counterweight 36 are to rotate downwards.

Here, the gear 37C is provided to mesh with the gear 37B between the gear 37A and the gear 37B. The gear 37D is provided to mesh with the gear 37A between the gear 37A and the gear 37B. The gear 37C and the gear 37D are coupled with each other through the rotary shaft 38A. Therefore, the gear 37C and the gear 37D rotate constantly in the same direction.

The gear 37C and the gear 37D having the above-described structure cancel out a downwardly rotating force that acts on both the movable portion 35 and the counterweight 36.

According to this embodiment, in addition to the functions and effects of the third embodiment, even if the copying apparatus 10E is set up in the horizontal direction to perform the copying operation sideways, the moment force in the direction along which the shoe 1 moves away from the workpiece 100B due to an influence of the gravitational force can be reduced.

It is to be noted that the copying apparatus 10E according to this embodiment has the configuration in which the counterweight 36 is used to enable a swiveling motion of the gear 37B. Therefore, when the copying apparatus 10E is configured to include a mechanism which uses the counterweight 36 to enable a swiveling motion of the gear 37B, structures modified in many ways can be provided.

A modification using arched slide guides as the mechanism that enables swiveling will now be described.

(Modification of this Embodiment)

Figure 15:
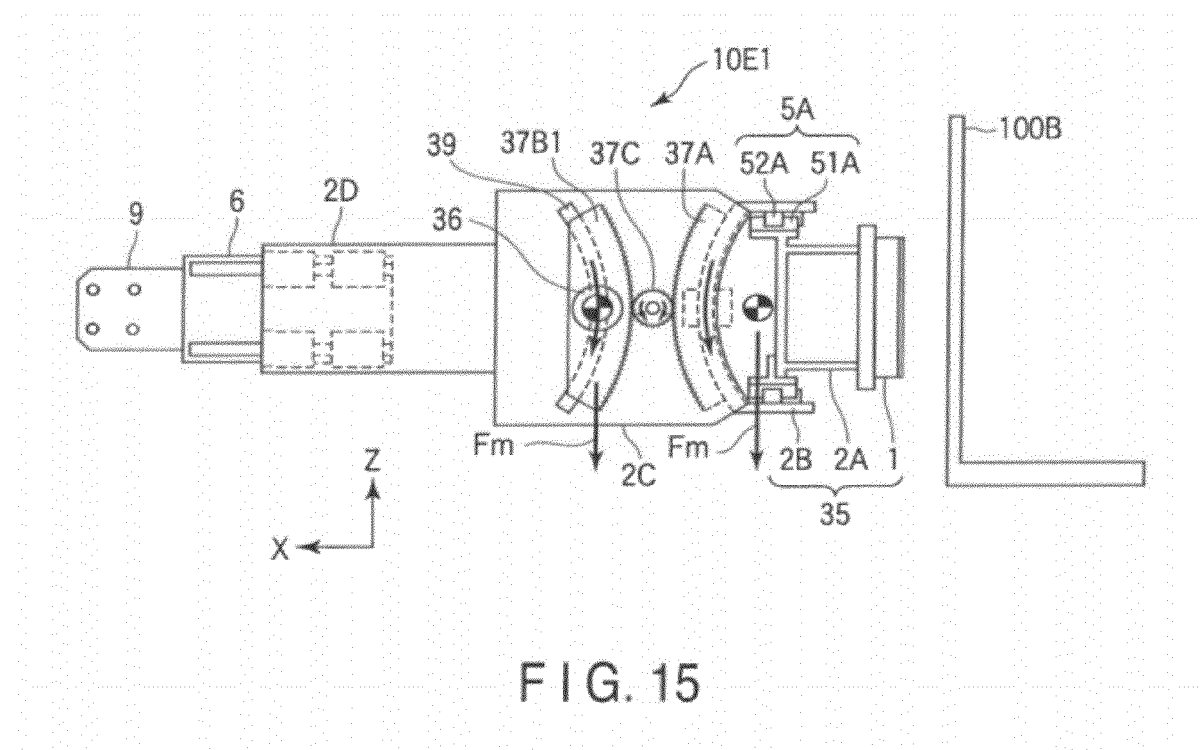
FIG. 15 is a front view showing a configuration of a copying apparatus according to a modification of the sixth embodiment of the present invention.

FIG. 15 is a front view showing a configuration of a copying apparatus 10E1 according to a modification of this embodiment.

The copying apparatus 10E1 has a configuration in which arched slide guides 39 are provided in place of a pin 38B and a gear 37B1 is provided in place of the gear 37B in the copying apparatus 10E according to this embodiment. Any other points are the same as those in the copying apparatus 10E.

That is, the copying apparatus 10E has the configuration in which the gear 37B can be swiveled around the pin 38B as a swiveling center. On the other hand, the copying apparatus 10E1 has the configuration in which the gear 37B1 can be swiveled by using the arched slide guides 39.

The arched slide guides 39 are disposed in such a manner that the gear 37B1 can be swiveled in an arched pattern like the arched slide guides 5A and 5B.

The gear 37B1 has a shape and the configuration which enable downward movement along the arched slide guides 39 based on a weight of a counterweight 36.

Even if the copying apparatus 10E1 according to such a modification is adopted, the same functions and effects as those in the copying apparatus 10E can be obtained.

Seventh Embodiment

Figure 16:
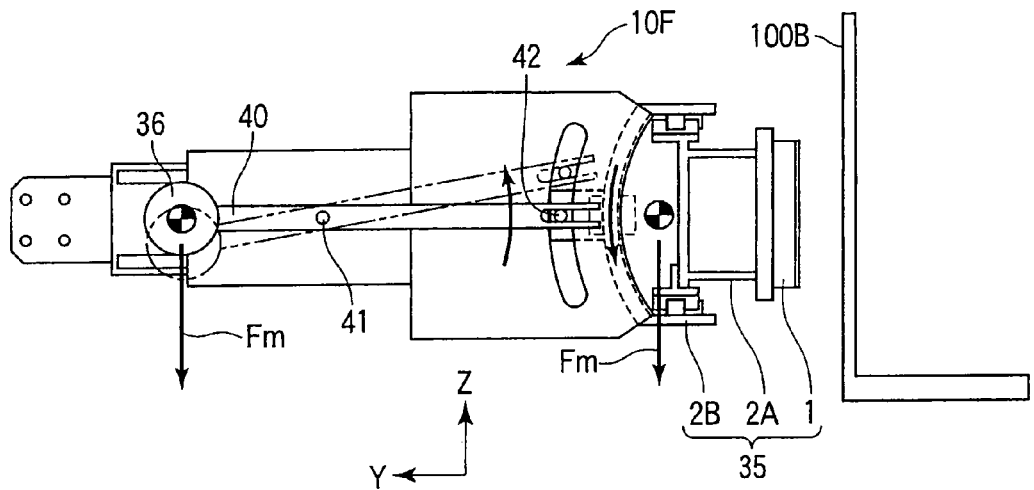
FIG. 16 is a front view showing a configuration of a copying apparatus according to a seventh embodiment of the present invention.

FIG. 16 is a front view showing a configuration of a copying apparatus 10F according to a seventh embodiment of the present invention.

The copying apparatus 10F has a configuration in which a lever 40, a rotary shaft 41, and a pin 42 are provided in place of the gears 37A, 37B, 37C, and 37D and the rotary shafts 38A and 38B in the copying apparatus 10E according to the sixth embodiment depicted in FIG. 13. Any other points are the same as those in the copying apparatus 10E.

The copying apparatus 10E according to the sixth embodiment mainly uses the gears to reduce a moment force in the direction along which the shoe 1 moves away from the workpiece 100B based on the weight of the counterweight 36, but the copying apparatus 10F according to this embodiment has a configuration where the lever is utilized to obtain the same functions and effects.

An operation and the configuration of the copying apparatus 10F will now be described with reference to FIG. 16.

A counterweight 36 is disposed to one side of the lever 40 (which will be referred to as a "left-hand side of the lever 40" hereinafter). The other side of the lever 40 is coupled with a movable portion 35 through the pin 42 (which will be referred to as a "right-hand side of the lever 40" hereinafter).

the left-hand side of the lever 40 downwardly rotates around the rotary shaft 41 based on a gravitational force applied to the lever counterweight 36. Contrarily, the right-hand side of the lever 40 moves up to lift up the pin 42 coupled with the movable portion 35 of the copying apparatus.

Therefore, when an appropriate weight of the counterweight 36 is given, a moment force in a direction along which a shoe 1 moves away from a workpiece 100B can be reduced even though a copying operation is performed in, e.g., a transverse posture.

According to this embodiment, in addition to the functions and effects provided by the third embodiment, utilizing the principle of leverage enables reducing the moment force in a direction along which the shoe 1 moves away from the workpiece 100B caused by an influence of the gravitational force even though the copying apparatus 10E is set up in the horizontal direction and the copying operation is performed in the transverse posture.

Eighth Embodiment

Figure 17:
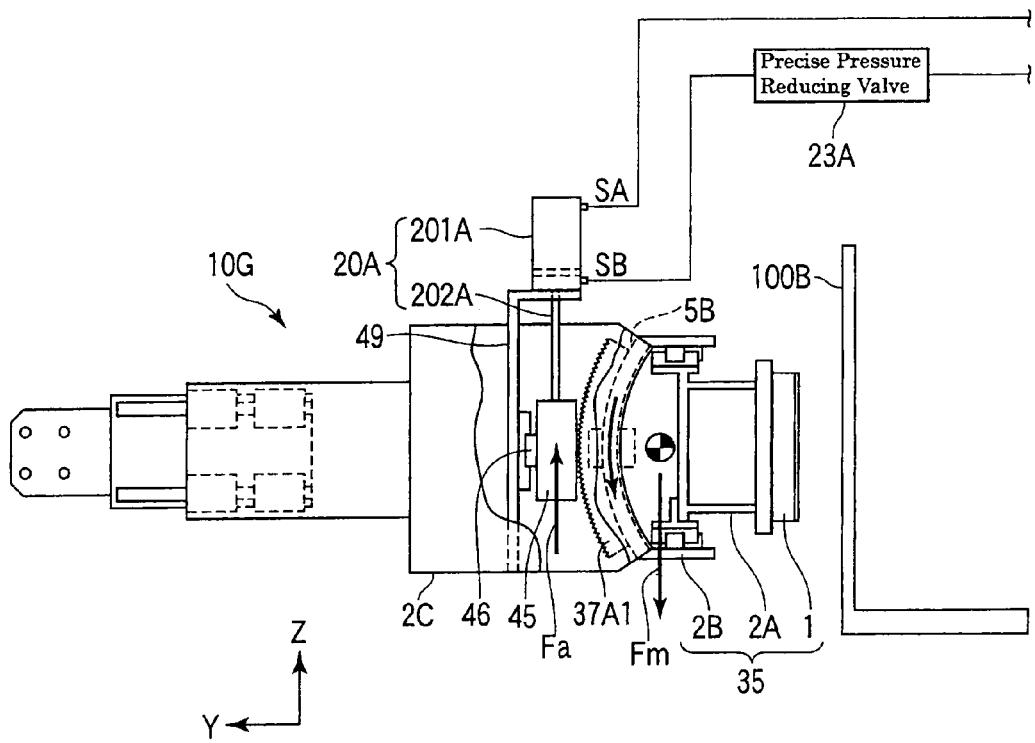
FIG. 17 is a front view showing a configuration of a copying apparatus according to an eighth embodiment of the present invention.

FIG. 17 is a front view showing a configuration of a copying apparatus 10G according to an eighth embodiment of the present invention. It is to be noted that FIG. 17 shows the copying apparatus 10G in a partially cutaway perspective view or the like.

The copying apparatus 10G has a configuration in which a gear 37A1, a rack 45, a translation guide 46, an air cylinder 20A, a precise pressure reducing valve 23A, and a bracket 49 are provided in place of the gears 37A, 37B, 37C, and 37D and the rotary shafts 38A and 38B in the copying apparatus 10E according to the sixth embodiment depicted in FIG. 13. Any other points are the same as those in the copying apparatus 10G.

The gear 37A1 is the same component as the gear 37A in the copying apparatus 10E according to the sixth embodiment. The gear 37A1 is disposed to a frame 2B as a part of a movable portion 35. The gear 37A1 has an arched shape which is provided along a shape of each arched slide guide 5B. The gear 37A1 can move to describe an arc with movement of the movable unit 35 by the arched slide guides 5B.

The rack 45 meshes with teeth of the gear 37A1 and is disposed to move with movement of the gear 37A1.

The translation guide 46 is disposed to mesh with the gear 37A1. The translation guide 46 can move in a trajectory to describe an arc of the gear 37A1, thereby allowing the rack 45 to linearly move in an up-and-down direction. When the gear 37A1 moves down, the rack 45 also moves down. When the gear 37A1 moves up, the rack 45 also moves up.

The air cylinder 20A includes a cylinder 201A and a rod 202A. The rod 202A connects the cylinder 201A with the rack 45. The air cylinder 20A is held by the bracket 49 fixed to a frame 2C. The air cylinder 20A is a component which is equivalent to the air cylinder 20 according to the third embodiment.

The precise pressure reducing valve 23A controls an air pressure in the air cylinder 20A. The precise pressure reducing valve 23A is disposed to control an air pressure on an 5B side (a lower side) of the air cylinder 20A. The precise pressure reducing valve 23A is a component equivalent to the precise pressure reducing valve 23 according to the third embodiment.

An operation of the copying apparatus 10G will now be described.

When the copying apparatus 10G is set up sideways, a moment force Fm in a downward direction caused by a gravitation force acts on the movable portion 35. Thus, the precise pressure reducing valve 23A supplies compressed air to the 5B side of the air cylinder 20A. As a result, the air cylinder 20A can generate a force Fa which moves up the rack 45.

Here, when the precise pressure reducing valve 23A generates a force substantially equal to a weight of the movable portion 35 in the air cylinder 20A, the force Fa which tries moving up the rack 45 and the force Fm which tries moving down the movable portion 35 can be balanced. That is, the copying apparatus 10G can reduce the moment force Fm in a direction along which a shoe 1 moves away from a workpiece 12 even though the copying operation is performed.

Furthermore, when the precise pressure reducing valve 23A is used for a pneumatic circuit, the force which tries moving up the rack 45 can be made constant. Moreover, this force can be readily adjusted.

When the copying apparatus 10G is used in a vertical direction, an influence of the gravitational force must be hardly taken into consideration. Therefore, in this case, for example, a non-illustrated electromagnetic valve is used to open the pneumatic circuit connected with the air cylinder 20A. As a result, the copying apparatus 10G can be used as a copying apparatus whose function concerning the gravitational force is canceled (e.g., a copying apparatus corresponding to the copying apparatus 10B according to the third embodiment).

According to this embodiment, in addition to the functions and effects provided by the third embodiment, using the air cylinder 20A enables reducing the moment force in the direction along which the shoe 1 moves away from the workpiece 100B due to the influence of the gravitational force even though the copying apparatus 10E is set up in the horizontal direction and the copying operation is performed in the lateral direction.

Ninth Embodiment

Figure 18B:
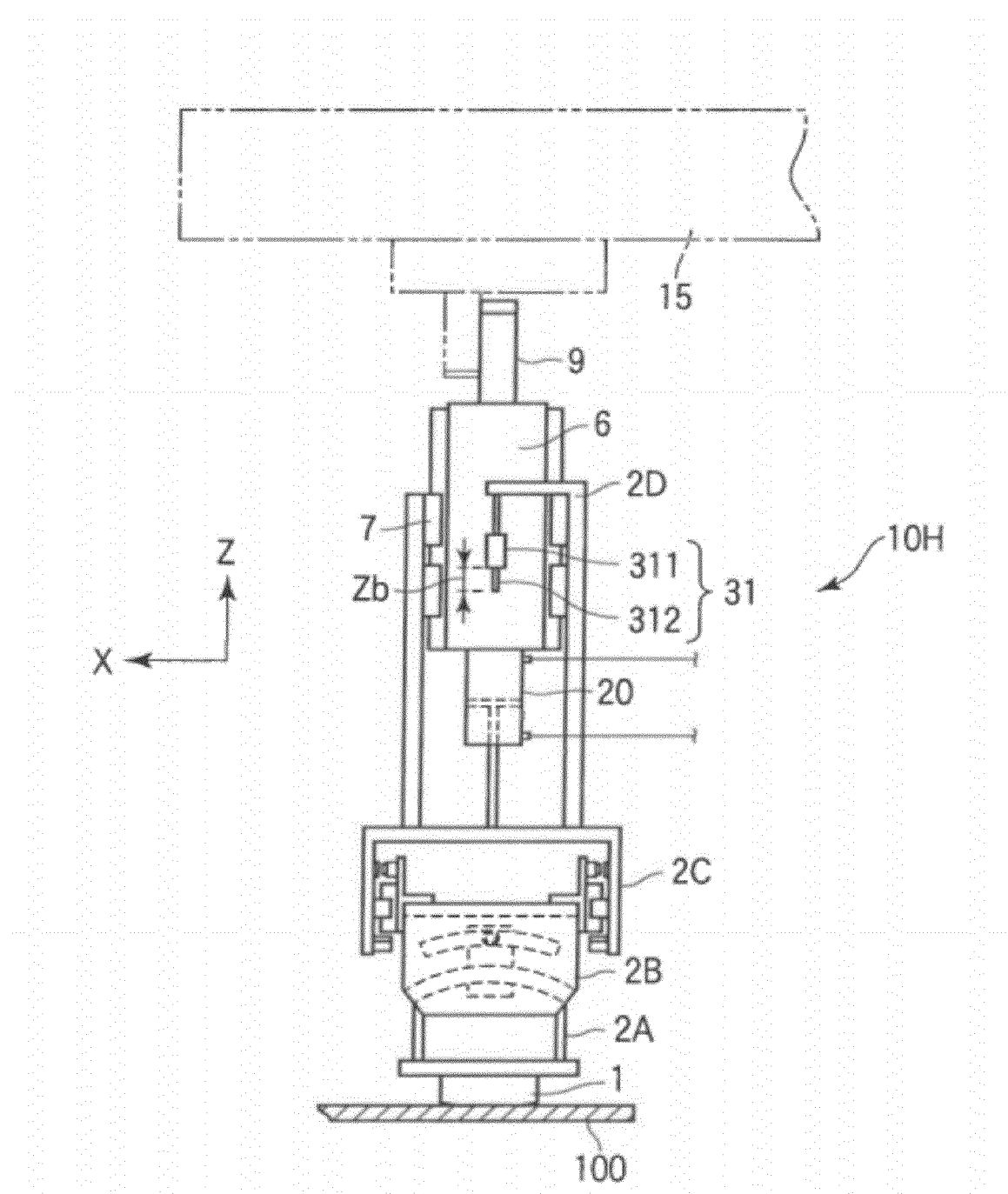
FIG. 18B is a state diagram showing a state after the copying apparatus according to the ninth embodiment of the present invention has copied the workpiece.

Each of FIGS. 18A and 18B is a front view showing a configuration of a copying apparatus 10H according to a ninth embodiment of the present invention.

The copying apparatus 10H includes a displacement sensor 31 in the copying apparatus 10B according to the third embodiment depicted in FIG. 6. Any other points are the same as those in the copying apparatus 10B.

The displacement sensor 31 measure a distance in a direction along which the copying apparatus 10H is pressed. The displacement sensor 31 is, e.g., a differential transformer type displacement sensor. It is to be noted that any sensor type can be adopted as long as the displacement sensor 31 can measure a translation distance.

The displacement sensor 31 includes a differential transformer portion 311 and a moving core 312. The differential transformer portion 311 is fixed to a slide portion 6. The moving core 33 is fixed to a frame 2D. Based on such a configuration, the moving core 33 can grasp displacement in the direction along which the copying apparatus 10H is pressed.

When a workpiece 100 having a curves surface is copied, a length for which copying is performed by the copying apparatus 10H is measured as follows.

FIG. 18A is a state diagram showing a state before the copying apparatus 10H copies the workpiece 100. FIG. 18B is a state diagram showing a state after the copying apparatus 10H copies the workpiece 100.

Here, it is assumed that a feeding direction (a copying direction) of a feeder apparatus 15 is an X axis and a pressing direction is a Z axis. In the copying apparatus 10H which is in a state before copying (before measurement), it is assumed that displacement in the pressing direction indicated by the displacement sensor 31 is Za. In the copying apparatus 10H in a state after copying (immediately before measurement), it is assumed that displacement in the pressing direction indicated by the displacement sensor 31 is Zb. Here, it is assumed that a distance (displacement in the X direction) in the feeding direction (the copying direction) of the copying apparatus 10H is X. At this time, a length L for which the curved surface is copied can be calculated as follows.

Displacement in the Z direction=Za−Zb (an upward direction is positive and a downward direction is negative.)

Here, when displacement in the Z direction <0, the feeder apparatus 15 is displaced in a direction along which it gets closer to the workpiece 100. When displacement in the Z direction >0, the feeder apparatus 15 is displaced in a direction along which it moves away from the workpiece 100.

$$L=\sqrt{(\text{displacement in the X direction}^2+\text{displacement in the Z direction}^2)}$$

where "^" is an operator indicative of square.

According to this embodiment, in addition to the functions and effects provided by the third embodiment, the following functions and effects can be obtained.

In the copying apparatus 10H, one point of the arched slide guides (the central point O) is the swiveling center for copying as explained above in the first embodiment. Therefore, a point copied on the curved surface of the workpiece 100 does not fluctuate within the X-Y plane.

Thus, measuring displacement in the X direction as the traveling direction and each of Za and Zb as displacement in the pressing direction before and after copying the workpiece 100 enables measuring a distance L for which the copying apparatus 10H performs copying based on the above-described computational expression. A positional coordinate can be three-dimensionally grasped based on this measured distance L. For example, a measurement point may be three-dimensionally plotted to draw the copied curved surface of the workpiece 100.

Therefore, the copying apparatus 10H can measure displacement in the pressing direction and calculate a result of this measurement to three-dimensionally grasp a coordinate of a copied position.

Further, the feeder apparatus 15 can be controlled to be moved in such a manner that a variation of a stroke for pressing the copying apparatus 10H by the feeder apparatus 15 becomes closer to 0.

10th Embodiment

FIG. 19 is a front view showing a configuration of a copying apparatus 10I according to a 10th embodiment of the present invention.

The copying apparatus 10I has a configuration in which an ultrasonic flaw detector 90 is disposed to a shoe 1 in the copying apparatus 10B according to the third embodiment depicted in FIG. 6. Therefore, the copying apparatus 10I is an ultrasonic flaw detection apparatus which uses the copying apparatus 10B as a copying apparatus. Any other points are the same as those in the copying apparatus 10B.

The ultrasonic flaw detector 90 is an element that can use ultrasound to detect a flaw of a workpiece 100 which comes into contact with the shoe 1. It is to be noted that a conveyance medium such as water for ultrasonic flaw detection is separately supplied through, e.g., a hose.

The feeder apparatus 15 presses the copying apparatus 10I against the workpiece 100, thereby directing the shoe 1 toward a normal line direction of a curved surface of the workpiece 100.

Then, the copying apparatus 10I is brought into contact with the workpiece 100 and the feeder apparatus 15 is moved. As a result, the ultrasonic flaw detector 90 and the shoe 1 copy the curved surface of the workpiece 100. At this time, the shoe 1 faces the normal line direction with respect to the curved surface of the workpiece 100. Therefore, the ultrasonic flaw detector 90 can constantly vertically apply ultrasound to the curved surface to detect and measure a flaw. Based on a result of the measurement by this ultrasonic flaw detector 90 which has copied the curved surface of the workpiece 100, a flaw detection image can be obtained.

An ultrasonic flaw detection method for the workpiece 100 by the copying apparatus 10I will now be described.

Figure 20:
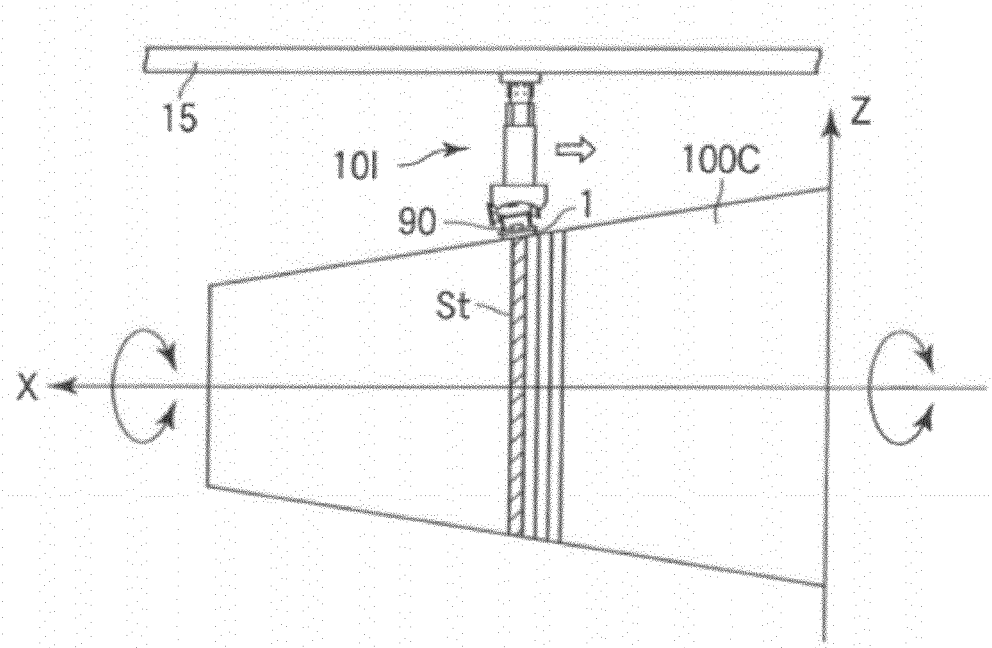
FIG. 20 is a schematic view showing a flaw detection method performed by the copying apparatus according to the 10th embodiment of the present invention on an X-Z plane.
Figure 21:
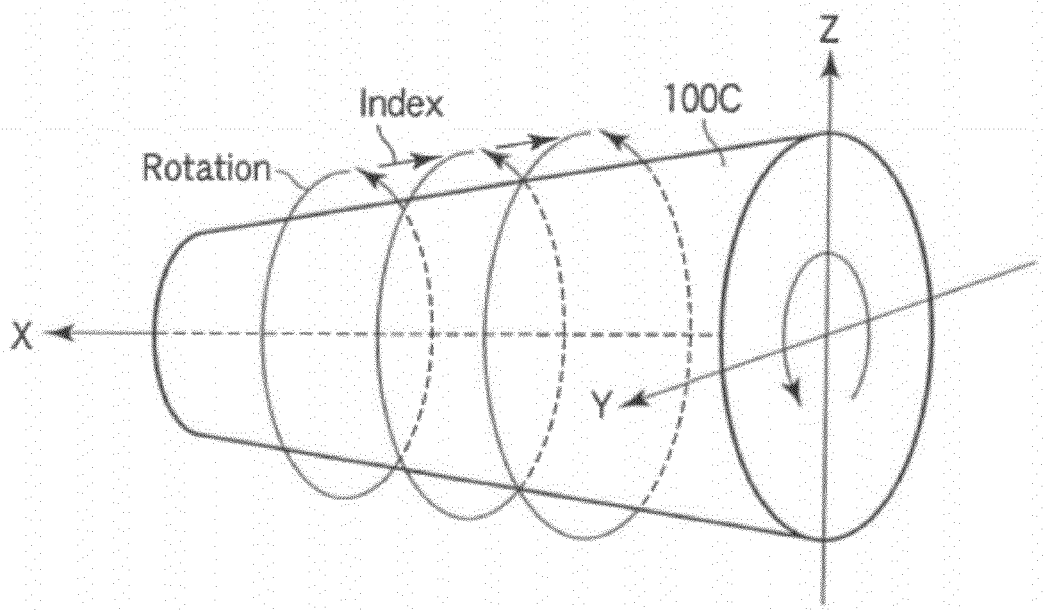
FIG. 21 is a schematic view showing the flaw detection method for a workpiece performed by the copying apparatus according to the 10th embodiment of the present invention.
Figure 22A:
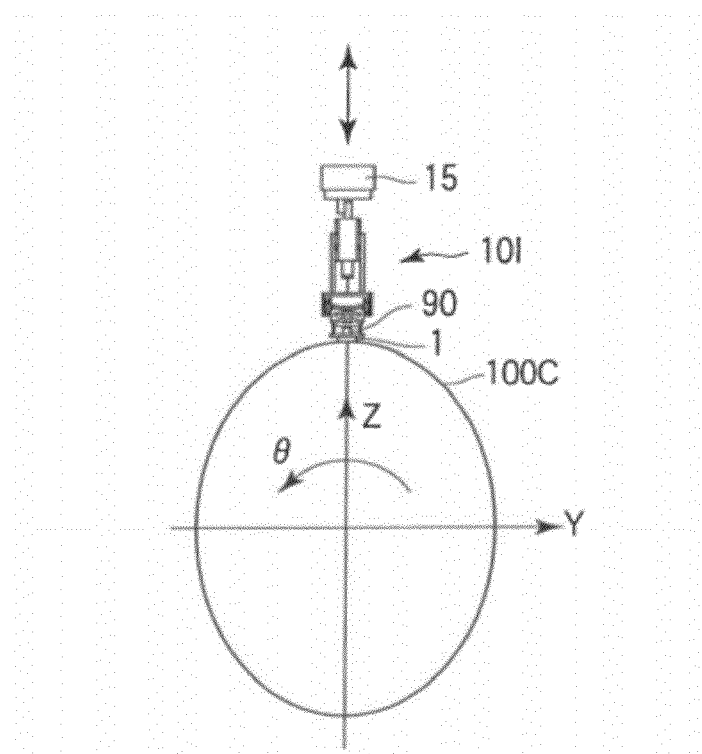
FIG. 22A is a state diagram showing a state of a first stage of copying a workpiece by the copying apparatus according to the 10th embodiment of the present invention.
Figure 22B:
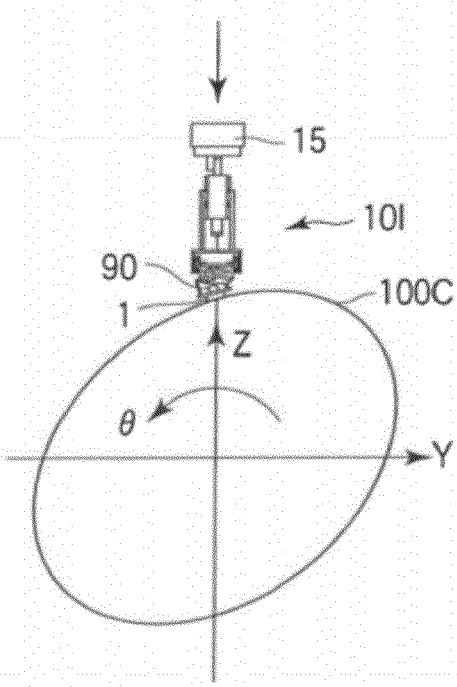
FIG. 22B is a state diagram showing a state of a second stage of copying the workpiece by the copying apparatus according to the 10th embodiment of the present invention.
Figure 22C:
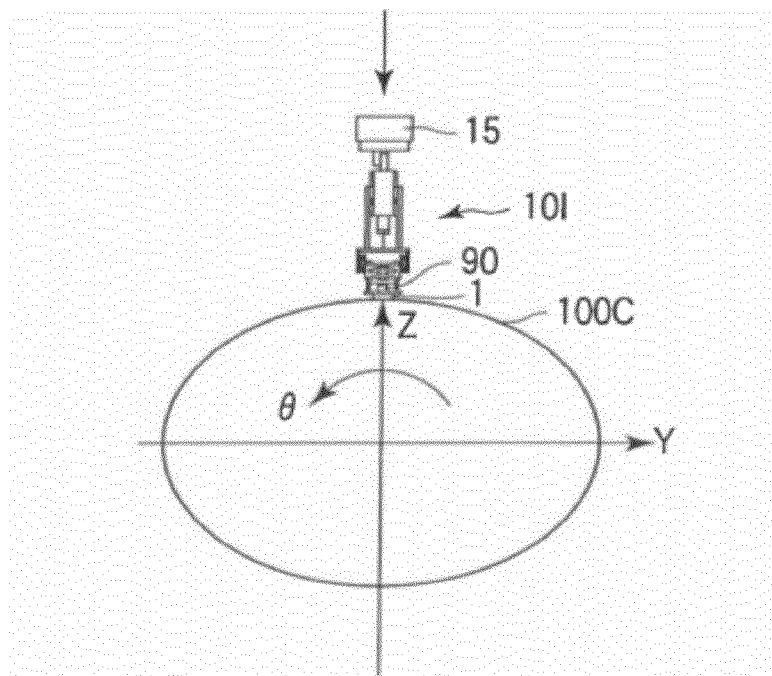
FIG. 22C is a state diagram showing a state of a third stage of copying the workpiece by the copying apparatus according to the 10th embodiment of the present invention.
Figure 22D:
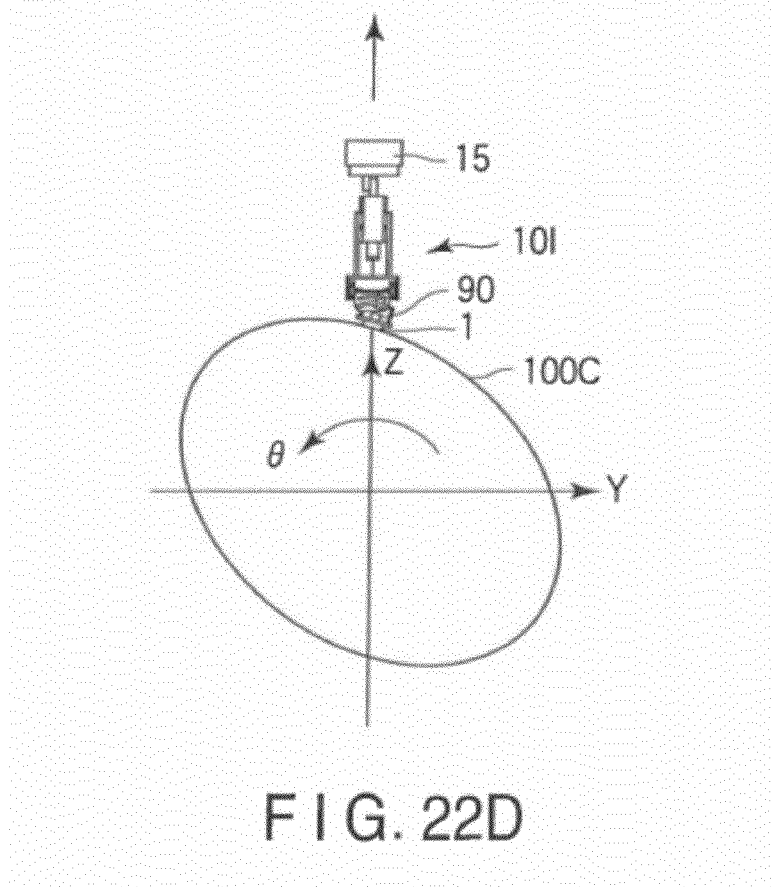
FIG. 22D is a state diagram showing a state of a fourth stage of copying the workpiece by the copying apparatus according to the 10th embodiment of the present invention.

FIG. 20 is a schematic view showing the flaw detection method performed by the copying apparatus 10I according to this embodiment on the X-Z plane. FIG. 21 is a schematic view showing the flaw detection method for the workpiece 100C by the copying apparatus 10I according to this embodiment. However, in the flaw detection method, an index direction or a rotating direction of the workpiece 100C are not restricted to directions shown in FIG. 21, and they may be arbitrarily set.

The workpiece 100C has a cylindrical or tapered shape. However, a cross-sectional shape of the workpiece 100C does not have to be a perfect circle. For example, it may be an elliptic shape or a shape obtained by deviating a rotation center of the workpiece from a center of a circle.

A rotary shaft of the workpiece 100C is provided in a longitudinal direction of the cylinder or the tapered shape, and the workpiece can be rotated by using a non-illustrated rotation device.

Here, it is assumed that the workpiece 100C is provided on such a coordinate system having the X axis, the Y axis, and the Z axis as depicted in FIG. 21 for purpose of illustration.

A method of detecting a flaw on an outer surface of the workpiece by rotating the workpiece 100C will now be described. It is to be noted that a representative example where a rotation angle of the workpiece 100C is 360 degrees will be described, but the workpiece 100C can be copied even if a rotation angle is 180 degrees or 20 degrees, thereby omitting an explanation thereof.

As shown in FIG. 20, the feeder apparatus 15 is first used to press the copying apparatus 10I against the workpiece 100C.

Then, the rotation device is used to rotate the workpiece 100C. Here, a region St of a range where the copying apparatus 10I can detect a flaw in one rotation is determined. Thus, when this region St is determined as a reference to repeat an index in the X direction, flaw detection in a necessary range is carried out.

A height of the workpiece 100C as the Z direction of the surface thereof may be changed.

A description will now be given as to a flaw detection method using the copying apparatus 10I when the height of the workpiece 100C as the Z direction of the surface is changed.

Each of FIGS. 22A, 22B, 22C, and 22D is a state diagram showing a state where the copying apparatus 10I copies the workpiece 100C. Each of FIGS. 22A to 22D shows a state where the workpiece 100C is sequentially rotated.

Basically, it is good enough to control a pressing amount of the feeder apparatus 15 in the Z direction in such a manner that the copying apparatus 10I comes into contact with the workpiece 100C in the range of a stroke. At this time, a pressing amount Z of the feeder apparatus 15 is represented as a rotation angle θ of the workpiece 100C and a distance from the rotation center of the same, and it is represented as follows:

$$Z = R(\theta)$$

That is, it is good enough to move the feeder apparatus 15 which holds the copying apparatus 10I in the Z direction like a cam with respect to a rotating operation of the workpiece 100C. Here, the copying apparatus 10I can absorb a stroke for copying in the Z direction. Therefore, even if a slight error in control is present, this error can be absorbed to perform copying.

Furthermore, when a distance between the workpiece surface and the rotation center of the workpiece is not constant, the normal line direction of the workpiece surface is changed. This change in normal line direction is absorbed by the copying apparatus 10I.

When flaw detection of the workpiece 100C for a necessary rotation angle is finished (for 360 degrees in this example), the copying apparatus 15 is indexed to the next flaw detection range in the X direction, and the same operation is repeated.

Although the method of detecting flaws on the outer surface of the workpiece 100C has been explained, this method can be likewise applied to a case where a flaw on an inner surface is detected. That is, the copying apparatus 10I can be brought into contact with the inner side of the workpiece 100C to perform flaw detection.

According to this embodiment, in addition to the functions and effects provided by the third embodiment, the following functions and effects can be obtained.

According to the ultrasonic flaw detection method using the copying apparatus 10I, even in case of a workpiece having an elliptic shape or a shape whose rotation center eccentrically deviates from a center of a circle, a flaw on a surface of this workpiece can be detected by ultrasound without performing special complicated control in order to change the normal line direction of the copying apparatus. Therefore, the copying apparatus 10I can perform ultrasonic flaw detection without using complicated control with respect to a curved plate, a flat plate, and a workpiece having a three-dimensional curved surface.

Furthermore, the copying apparatus 10I can perform ultrasonic flaw detection in a state where it constantly faces the normal line direction of the surface of the workpiece 100C.

Additionally, the feeder apparatus 15 does not require complicated control, e.g., controlling a posture of the copying apparatus along an inclination of the curved surface in order to obtain an ultrasonic flaw detection image. Therefore, it is preferable for ultrasonic flaw detection for a workpiece having a three-dimensional curved surface, e.g., an air frame surface of an aircraft.

For example, when a body of an aircraft is rotated and fed in the Z direction and the X direction while bringing the copying apparatus into contact with the body of the aircraft and the body of the aircraft is rotated, ultrasonic flaw detection in a necessary range can be performed. Further, a body cross section is not restricted to a simple cylindrical cross section. For example, even in case of a portion having a streamline shape like a front part or a rear part of an air frame of an aircraft, the copying apparatus can copy a curved surface without especially performing complicated control, which is very preferable.

11th Embodiment

Figure 23A:
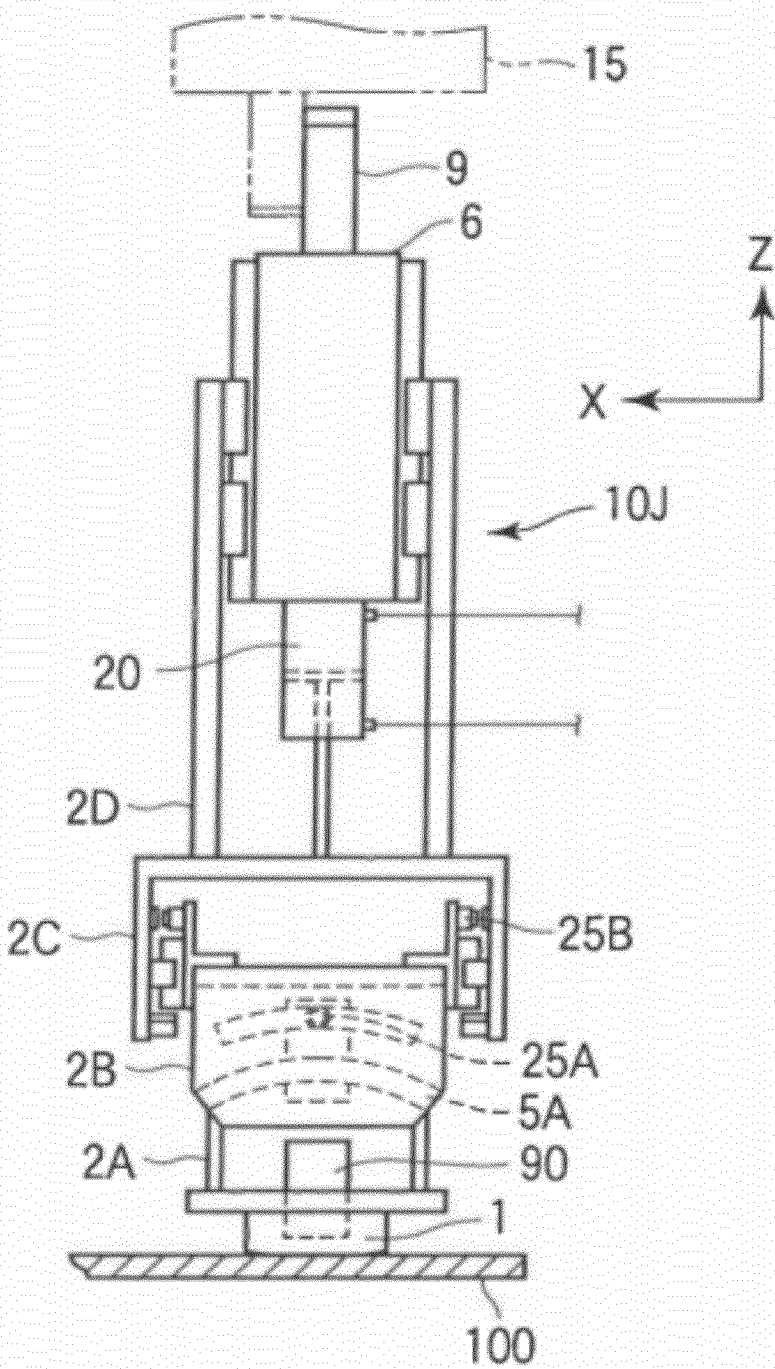
FIG. 23A is a state diagram showing a state during regular flaw detection performed by a copying apparatus according to an 11th embodiment of the present invention.
Figure 23B:
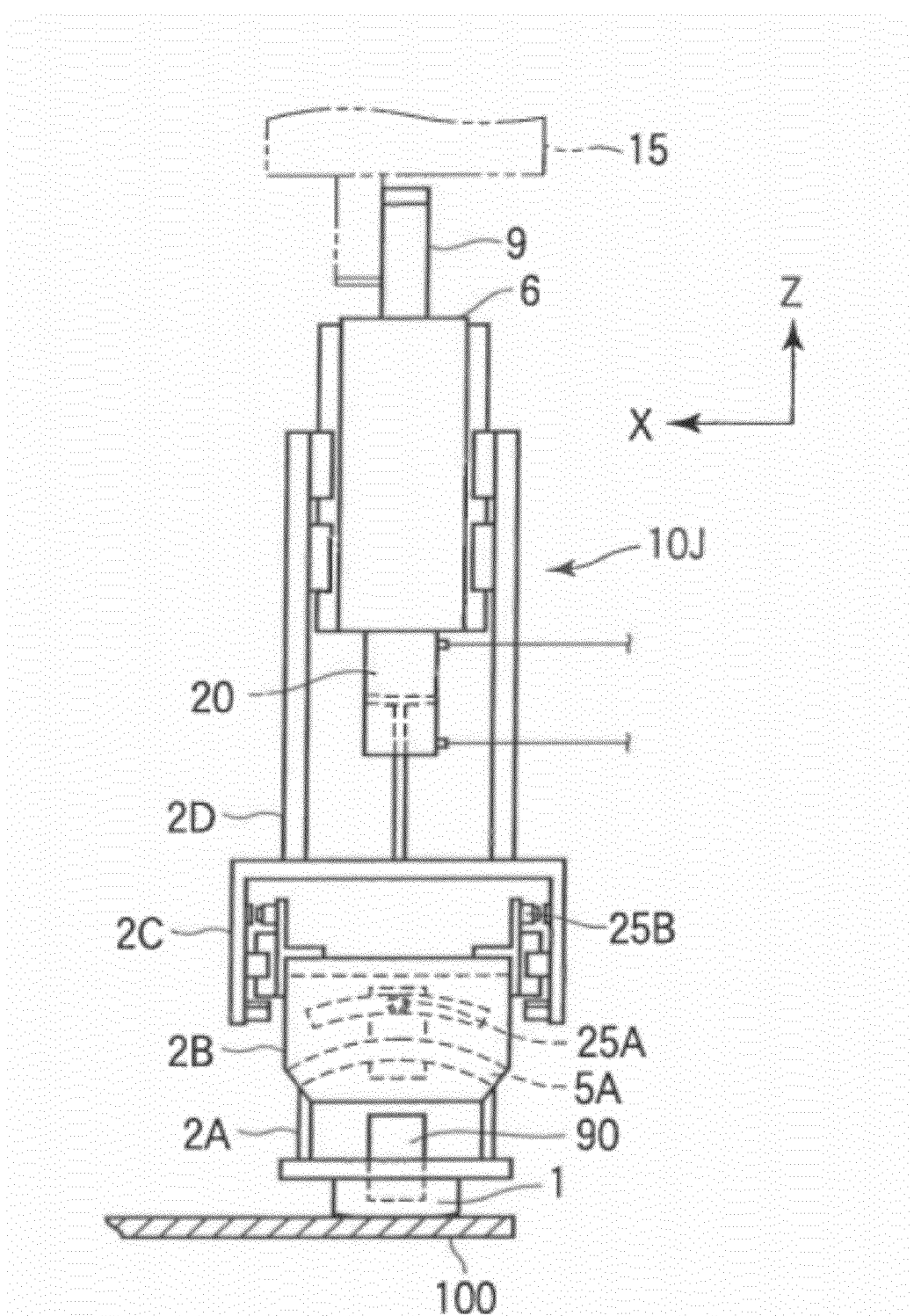
FIG. 23B is a state diagram showing a state immediately before the copying apparatus according to the 11th embodiment of the present invention reaches an end portion of a workpiece.

Each of FIGS. 23A, 23B, and 23C is a state diagram showing a state during flaw detection performed by a copying apparatus according to the 11th embodiment.

The copying apparatus 10J has a structure in which an ultrasonic flaw detector 90 is disposed to a shoe 1 in the copying apparatus 10C according to the fourth embodiment depicted in FIGS. 8A to 9. Therefore, the copying apparatus 10J is an ultrasonic flaw detection apparatus using the copying apparatus 10C as a copying mechanism. Any other points are the same as those in the copying apparatus 10C.

The ultrasonic flaw detector 90 is an element that can perform ultrasonic flaw detection with respect to a workpiece 100 which comes into contact with the shoe 1. It is to be noted that a conveying medium such as water for ultrasonic flaw detection is separately supplied through, e.g., a hose.

An operation of using the copying apparatus 10J to perform ultrasonic flaw detection to an end portion of the workpiece 100 will now be described.

Here, a last portion to which the copying operation is effected is an end portion of this workpiece 100.

FIG. 23A is a state diagram showing a state during regular flaw detection of the copying apparatus 10J. FIG. 23B is a state diagram showing a state immediately before the copying apparatus 10J reaches the end portion of the workpiece 100. FIG. 23C is a state diagram showing a state when the copying apparatus 10J is passing the end portion of the workpiece 100. The copying operation for the workpiece 100 by the copying apparatus 10J is carried out in order of FIGS. 23A to 23C.

The copying apparatus 10J in FIG. 23A normally performs flaw detection with respect to the workpiece 100.

A brake 25A is actuated while the copying apparatus 10J shifts from the state depicted in FIG. 23B to the state shown in FIG. 23C. As a result, even if the copying apparatus 10J passes the end portion of the workpiece 100 by actuating the brake 25A before passing the end portion of the workpiece 100, a posture of the copying apparatus 10J is not collapsed. Therefore, the copying apparatus 10J can perform appropriately stable ultrasonic flaw detection with respect to the end portion of the workpiece 100.

Likewise, when the workpiece 100 has an opening portion like a hole, actuating the brake 25A before the copying apparatus 10J passes the opening portion enables carrying out ultrasonic flaw detection with a degree of freedom for copying being limited.

Although the description has been given as to an example where the brake 25A is actuated, the same operation is performed when actuating a brake 25B.

According to this embodiment, since a posture of the copying apparatus 10J is not collapsed at the end portion or in the opening portion of the workpiece by actuating the brake 25A or 25B, ultrasonic flaw detection that can obtain a constantly excellent ultrasonic flaw detection image can be effected.

It is to be noted that each embodiment can be modified and carried out as follows.

In regard to attachment of the arched slide guide 5A, the rail 52A and the block 51A can be disposed to either the frame 2B or 2C. Likewise, in the arched slide guide 5B, the rail 52B and the block 51B can be disposed to either the frame 2B or 2C. This can be likewise applied to attachment of the translation guide 7.

Further, each of the numbers of arched slide guides 5A and 5B is two, any number can be adopted. Likewise, any number can be adopted for the translation guides 7. Furthermore, rail radiuses of the arched slide guides 5A and 5B may be equal to or different from each other as long as swiveling centers are equal to each other.

Furthermore, the description has been given as to the structure where the shape of the contact surface of the shoe 1 has an area like a flat plate, the contact surface of the shoe 1 may have a shape having a plurality of contact points (e.g., four protrusions or rollers) with respect to a workpiece in a copying direction.

Moreover, although the configuration where slide portion 6 is provided to the copying apparatus 10 is adopted, the slide portion 6 may be provided on the feeder apparatus 15 side. The slide portion 6 may be disposed at any position as long as it is configured to prevent an excessive pressing force from being applied to the workpiece 100.

Additionally, an attachment direction of the air cylinder 20 may be opposite. That is, the cylinder 201 may be fixed to the frame 2C and the rod 202 may be fixed to the slide portion 6, respectively.

Figure 7:
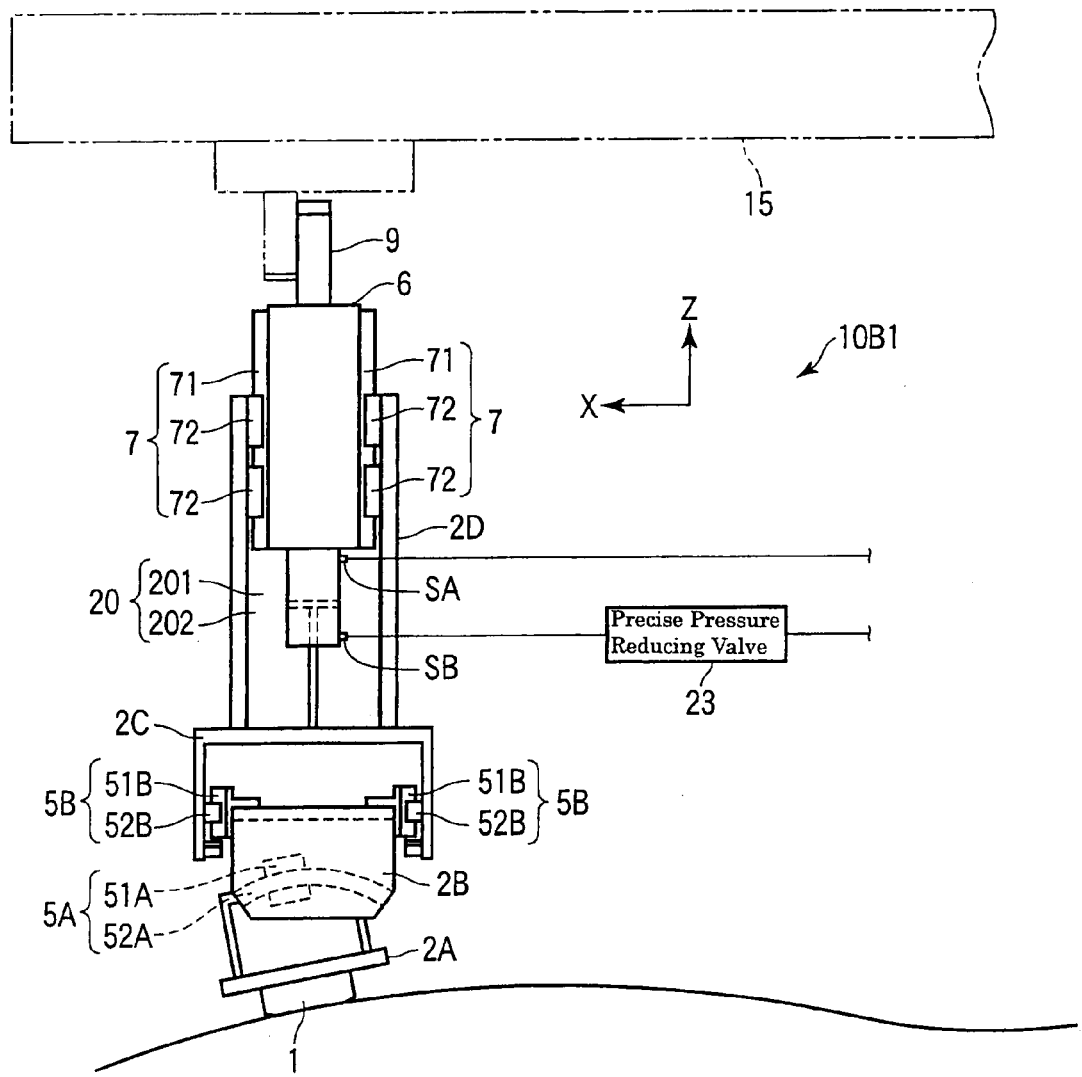
FIG. 7 is a block diagram showing the configuration of the copying apparatus according to the third embodiment of the present invention.

Further, the precise pressure reducing valve 23 is arranged to control an air pressure on the 5A side (the upper side) of the air cylinder 20, but the present invention is not restricted thereto. For example, as the copying apparatus 10B1 according to the modification of the third embodiment, as shown in FIG. 7, the precise pressure reducing valve 23 may be arranged to control an air pressure on the 5B side (the lower side) of the air cylinder 20. As a result, the copying apparatus 10B1 can apply a weak pressing force to the workpiece 100. That is, in the copying apparatus 10B1, the precise pressure reducing valve 23 is arranged on the 5B side of the air cylinder 20 to supply compressed air having an adjusted pressure. As a result, the air cylinder 20 can generate a force in a direction along which the shoe 1 is lifted up rather than a direction along which the copying apparatus 10B1 is pressed. That is, the precise pressure reducing valve 23 adjusts an air pressure in a direction along which a weight of the copying apparatus 10B1 is reduced. Therefore, when a pressure of this compressed air is appropriately adjusted, a force that the copying apparatus 10B1 presses the workpiece 100 can be weakened, and adjustment of this force can be facilitated. Thus, the workpiece 100 can be copied with a weak pressing force. Therefore, the copying apparatus 10B1 is preferable for an example where a workpiece which is apt to be deformed by external force, e.g., a workpiece having a small board thickness is copied.

Further, the degree of freedom of installation of the braking device such as brake or the number of the same may be provided as required. For example, in case of the copying apparatus 10C, the braking devices (the brakes 25A and 25B) are provided with respect to the degrees of freedom of the two arched slide guides, respectively.

Furthermore, when holding the copying apparatus in the pressing direction is desirable, providing the braking device to the slide portion 6 (or the frame 2D) of the pressing shaft enables maintaining the slide portion in a pressed state (a height). A configuration for disposing such a braking device may be the same as that of the brake 25A or 25B or any other type.

Moreover, when the plurality of braking devices are provided, they may be operated independently or in cooperation with each other in accordance with a use application.

Additionally, in regard to the braking mechanism, the structural example where the brake 25A or 25B is of a brake air pressure type has been described, but the present invention is not restricted thereto. A braking method of the braking mechanism, e.g., a mechanical type or an electrical type can be appropriately selected as long as it has a function of enabling holding a posture by restricting a degree of freedom of the copying apparatus.

Further, although the non-contact type sensor has been explained as the sensor 30, the present invention is not restricted to the non-contact type in particular, and satisfying the above-described function can suffice even when a contact type is adopted. Furthermore, the number of or positions of the sensors to be disposed do not have to be restricted, and they may be disposed at positions where an end portion or an edge of a workpiece can be detected.

Moreover, the structures based on the copying apparatus 10B according to the third embodiment have been mainly explained in the fourth to 11th embodiments, but the present invention is not restricted thereto. In regard to structures based on any other embodiment, adopting the same structure enables obtaining the same functions and effects.

Additionally, as the precise pressure reducing valve 23A, a precise pressure reducing valve that can control an air pressure by using an electrical signal may be adopted. As a result, an air pressure can be adjusted in accordance with an arbitrary inclination of the copying apparatus, and an appropriate reduction in a moment force can be maintained. Further, this structure can be likewise applied to the precise pressure reducing valve 23, and using the precise pressure reducing valve that can be electrically controlled enables changing a pressing force (a contact force) based on external control.

Furthermore, although the embodiment where the copying apparatus is applied to the ultrasonic flaw detection apparatus as the copying mechanism has been explained, the present invention is not restricted thereto. The copying apparatus has many utility values in various fields, e.g., inspection, measurement, machining, and others. When the copying apparatus according to the present invention is utilized as a copying mechanism, copying can be performed while constantly bringing the shoe into contact with a workpiece in the normal line direction. Therefore, an application field does not have to be restricted to the field of ultrasonic flaw detection as long as it is a field requiring such characteristics.

Further, in each embodiment, the copying apparatus has the structure where the frame 2D and the slide portion 6 which are the mechanisms that vertically move the shoe to copy a workpiece are provided above the frame 2B and the frame 2C as the mechanisms which swivel in an arc pattern, but the present invention is not restricted thereto. Any configuration can be adopted as long as these mechanisms are incorporated in any position in the entire copying apparatus and respective functions of these mechanisms can be exercised. For example, a configuration where the vertically movable mechanism is coupled with a side of the mechanism that swivels in an arc pattern (a configuration where the frame 2D is coupled with the frame 2C to be aligned on the X-Y plane) may be adopted.

Furthermore, each embodiment has the configuration where the elastic boy 8 and the air cylinder 20 are provided below the slide portion 6, but the present invention is not restricted thereto. The elastic body 8 and the air cylinder 20 may be provided at any positions in the copying apparatus as long as they have a conformation that buffers a pressing force. For example, the elastic body 8 and the air cylinder 20 may be provided between the slide portion 6 and the frame 2C or 2D.

Moreover, in the eighth embodiment, when the rack 45 has a certain level of weight or a counterweight is provided to the rack 45, the above-described similar functions can be satisfied, and a structure in which the air cylinder 20A is eliminated can be provided. However, when the movable portion 35 largely swivels, weight balance of the rack 45 and the movable portion 35 differs depending on an inclination component (a sin component) of the movable portion 35, and hence enabling adjustment of a force by using the air cylinder 20A like this embodiment is beneficial.

12th Embodiment

Figure 24:
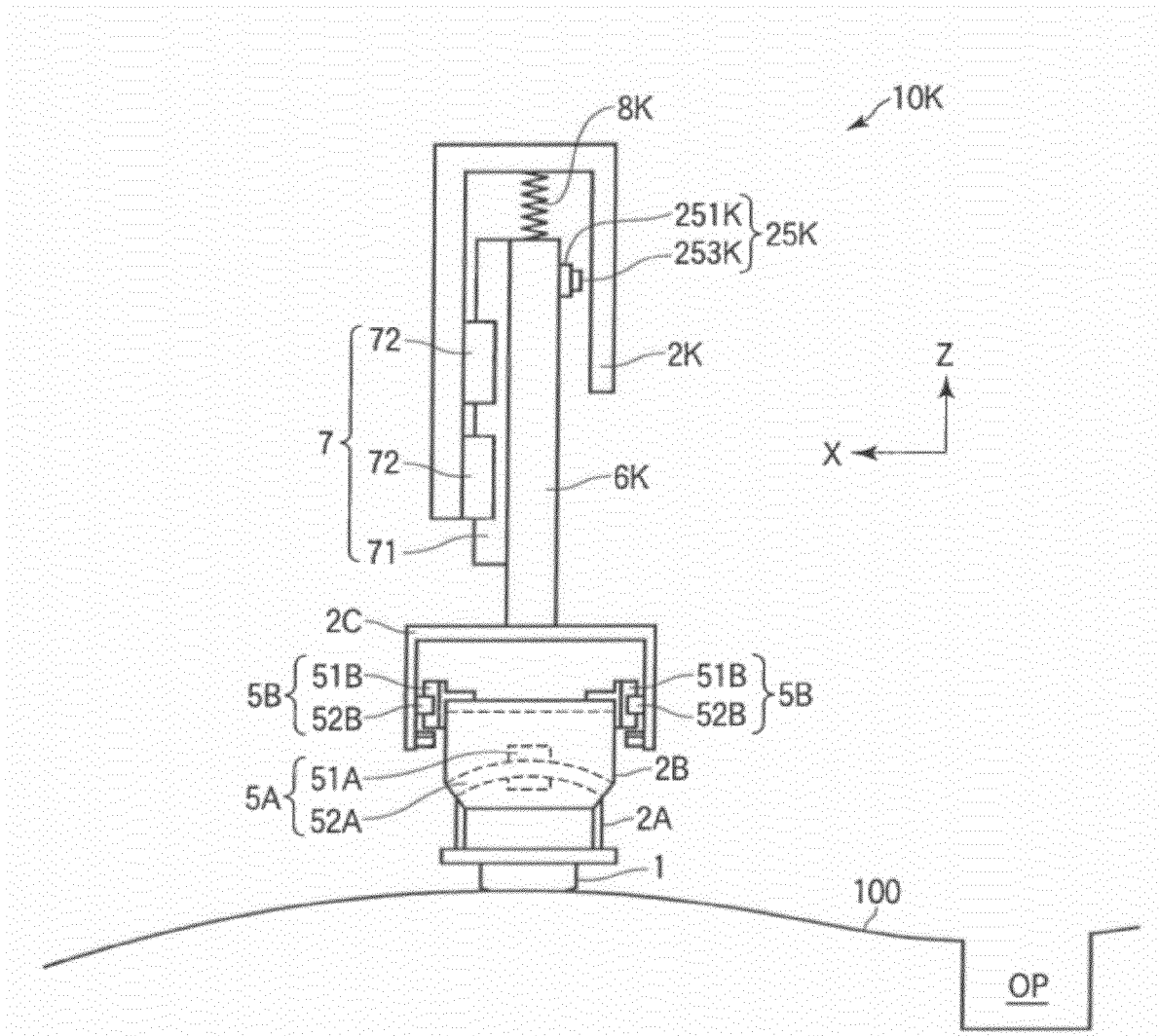
FIG. 24 is a front view showing a configuration of a copying apparatus according to a 12th embodiment of the present invention.

FIG. 24 is a front view showing a configuration of a copying apparatus 10K according to a 12th embodiment of the present invention.

The copying apparatus 10K includes a shoe 1, frames 2A, 2B, 2C, and 2K, arched slide guides 5A and 5B, a slide portion 6K, a translation guide 7, an elastic body 8K, and a holding mechanism 25K. The copying apparatus 10K copies a surface of a workpiece 100 when controlled by a non-illustrated feeder apparatus.

That is, the copying apparatus 10K is different from the copying apparatus 10 according to the first embodiment depicted in FIG. 1 in a mechanism that performs an operation in a vertical direction with respect to the workpiece 100. Any other points are the same as structures in the copying apparatus 10.

The frame 2K supports movement of the slide portion 6K in an up-and-down direction (a Z axis direction).

The slide portion 6K is provided to be fixed to an upper portion of the frame 2C.

The translation guide 7 is disposed to a side surface of the slide portion 6K opposite to a side surface of the same having the holding mechanism 25K provided thereto.

The translation guide 7 includes a rail 71 and two blocks 72. The rail 71 is fixed near a central portion of the slide portion 6K. The two blocks 72 are fixed to be aligned at a central portion of the frame 2K in the vertical direction. The two blocks 72 are provided to support the slide portion 6K which can move in the vertical direction. Based on this structure, the slide portion 6K can move in such a manner that the rail 71 becomes parallel to grooves formed in the blocks 72.

The elastic body 8K is provided between the frame 2K and an upper portion of the slide portion 6K. The elastic body 8K is, e.g., a spring. The elastic body 8K expands and contracts in a direction along which the slide portion 6K can slide (i.e., the up-and-down direction) by the translation guide 7. The elastic body 8K buffers a pressing force of the shoe 1 with respect to the workpiece 100. As a result, the copying apparatus 10K suppresses an excessive pressing force with respect to the workpiece 100. The elastic body 8K plays a role of absorbing displacement in the up-and-down direction when copying the workpiece 100. It is to be noted that the copying apparatus 10K may use the air cylinder 20 in place of the elastic body 8K like the copying apparatus 10B shown in FIG. 6.

The holding mechanism 25K is constituted of a cylinder 251K and a pad 253K. When an air pressure in the cylinder 251K is increased, the pad 253K is protruded from the cylinder 251K. When an air pressure in the cylinder 251K is reduced, the pad 253K is retracted into the cylinder 251K.

The holding mechanism 25K is controlled by a non-illustrated control device. This control device outputs a signal indicative of an operation or a non-operation to a non-illustrated electromagnetic valve. An air pressure is supplied to the cylinder 251K of the holding mechanism 25 through this electromagnetic valve. As a result, the pad 253K of the holding mechanism 25K is protruded or retracted. When the pad 253K is protruded, the pad 253K comes into contact with the frame 2K, and a frictional force is generated. As a result, the holding mechanism 25K holds a relative operation of the slide portion 6K and the frame 2K.

An operation of the holding mechanism 25K will now be described.

An example where the copying apparatus 10K passes an opening portion OP of the workpiece 100 will now be described with reference to FIG. 24.

The copying apparatus 10K actuates the holding mechanism 25K at a position before the copying operation reaches the opening portion OP, thereby holding a height of the shoe 1 in the Z direction.

The copying apparatus 10K actuates the holding mechanism 25K, and passes the opening portion OP while copying the workpiece 100 in a state where the height of the shoe 1 in the Z direction is held.

As a result, the shoe 1 is not inclined even though it gets to an end portion of the workpiece 100 before reaching the opening portion OP. Therefore, the copying apparatus 10K can copy the end portion of the workpiece 100 without inclining the shoe 1. Further, even if the shoe 1 passes the opening portion OP while copying the same, it can continuously copy the workpiece 100 ahead of the opening portion OP without being fitted in the opening portion OP.

When the copying apparatus 10K passes the opening portion OP without actuating the holding mechanism 25K, since the shoe 1 presses the workpiece 100, and hence the contracted elastic body 8K is restored (the elastic body 8 expands). Therefore, the shoe 1 is vigorously protruded at the opening portion OP.

Figure 25:
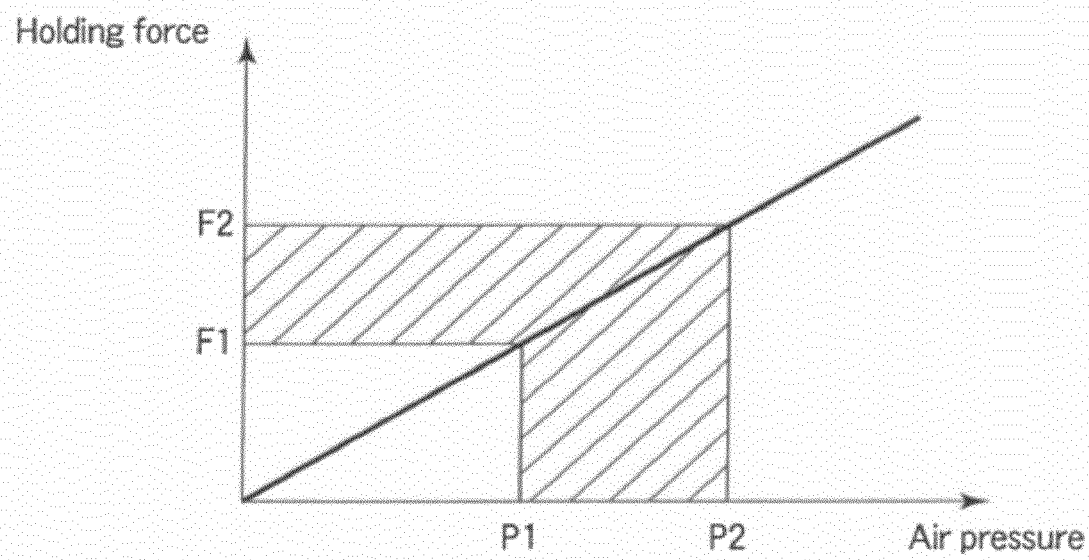
FIG. 25 is a graph chart for explaining a holding force of a holding mechanism according to the 12th embodiment of the present invention.

FIG. 25 is a graph chart for explaining a holding force of the holding mechanism 25K according to this embodiment. An ordinate represents a holding force of the holding mechanism 25K. An abscissa represents an air pressure in the cylinder 251K.

As shown in FIG. 25, an air pressure in the cylinder 251K and a holding force of the holding mechanism 25K has a substantially proportional relationship. That is, the control device increases an air pressure which is supplied to the cylinder 251K, thereby intensifying a holding force of the holding mechanism 25K. An air pressure P1 is an air pressure when the holding mechanism 25K has a holding force F1. An air pressure P2 is an air pressure when the holding mechanism 25K has a holding force F2.

The holding force F1 is a minimum required force that enables holding a posture of the shoe 1. That is, in case of a holding force weaker than the holding force F1, the holding mechanism 25K does not fulfill a function of the holding force.

The holding force F2 is a limit force that enables copying the workpiece 100 without damaging the workpiece 100. That is, in case of a holding force stronger than the holding force F2, the elastic body 8K does not function to suppress a pressing force of the shoe 1 with respect to the workpiece 100. Therefore, in a case where a surface of the workpiece 100 is not a flat surface, the copying apparatus 10K may possibly damage the workpiece 100 when the shoe 1 interferes with the workpiece 100. On the other hand, in case of a holding force weaker than the holding force F2, even if the shoe 1 interferes with the workpiece 100, the holding force of the holding mechanism 25K slips when an external force stronger than the holding force F2 functions. As a result, the copying apparatus 10K can avoid damaging the workpiece 100.

The holding forces F1 and F2 are determined based on a material of the workpiece 100.

Therefore, the holding force of the holding mechanism 25K is adjusted to constantly fall within the range between the holding force F1 and the holding force F2. In other words, an air pressure in the cylinder 251K is adjusted to constantly fall within the range between the air pressure P1 and the air pressure P2.

A pressure reducing valve is provided in a pneumatic circuit of the holding mechanism 25K. When an air pressure is adjusted by using this pressure reducing valve, a holding force of the holding mechanism 25K can be arbitrarily set. As this reducing valve, a precise pressure reducing valve or the like may be adopted to provide a role like relief valve. As a result, when a holding force that is excessive for holding is provided, an air pressure in the cylinder 251K which actuates the holding mechanism 25K may be partially let out. Consequently, the holding mechanism 25K can adjust an air pressure in the cylinder 251K to constantly fall within the range between the air pressure P1 and the air pressure P2.

According to this embodiment, in addition to the functions and effects of the first embodiment, the following functions and effects can be obtained.

Providing the holding mechanism 25K to the copying apparatus 10K enables avoiding an obstacle, e.g., a damage to the workpiece 100 which occurs when the shoe 1 is fitted in the opening portion OP of the workpiece 100 or the shoe 1 is protruded at the opening portion OP. As a result, the feeder apparatus which moves the copying apparatus 10K can avoid the above-described obstacle without strictly controlling, e.g., a position at which the copying operation of the copying apparatus 10K is stopped.

Further, the copying apparatus 10K can perform copying even if the workpiece 100 has a cylindrical shape or an arched shape. In this case, as a method of copying the workpiece 100, the copying apparatus 10K may be moved with respect to the workpiece 100, or the copying apparatus 10K may be fixed to rotate the workpiece 100. At this time, even if an intromitter is present in, e.g., the opening portion OP of the workpiece 100, the copying apparatus 10K can be prevented from falling off at the opening portion OP by actuating the holding mechanism 25K of the copying apparatus 10K in the same manner as explained above.

Furthermore, a holding force of the holding mechanism 25K is adjusted to fall within an adequate range. As a result, the holding mechanism 25K has a holding force that holds a height direction of the shoe 1 with respect to a force that substantially presses the workpiece 100. Moreover, when a pressing force with respect to the shoe 1 is an overload, a holding force of the holding mechanism 25K is reduced, thus preventing an excessive force from being supplied to the workpiece 100.

It is to be noted that the holding mechanism 25K obtains a holding force from an air pressure in this embodiment, but the present invention is not restricted thereto. As the holding mechanism 25K, a mechanical or electrical holding mechanism may be used. In such a configuration, the holding mechanism 25K can obtain the same functions and effects as those of this embodiment by adjusting a holding force thereof in the same manner as this embodiment.

13th Embodiment

Figure 26:
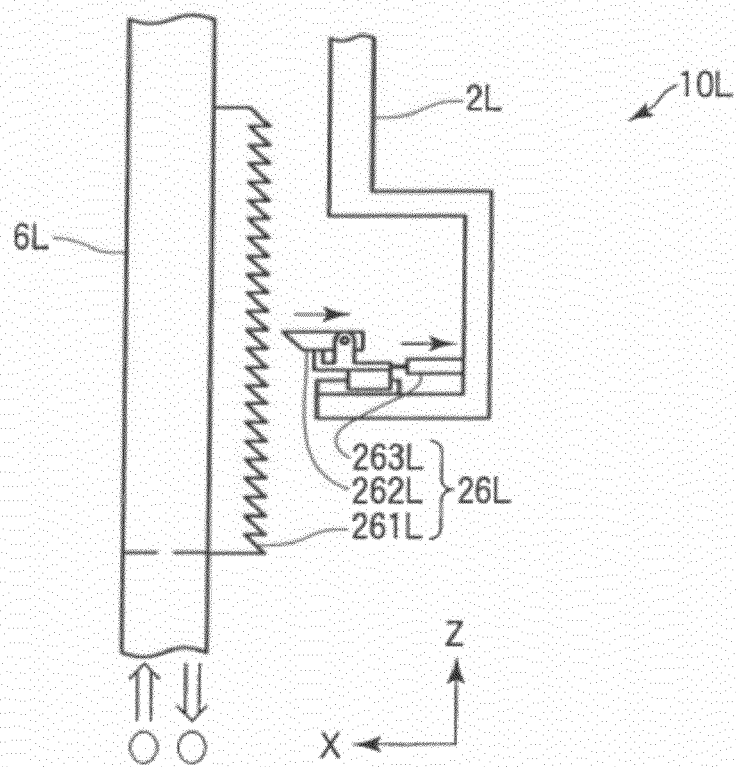
FIG. 26 is a front view showing a part of a configuration of a copying apparatus according to a 13th embodiment of the present invention.

FIG. 26 is a front view showing a part of a configuration of a copying apparatus 10L according to a 13th embodiment of the present invention.

The copying apparatus 10L has a configuration in which the holding mechanism 25K is substituted by a holding mechanism 26L in the copying apparatus 10K according to the 12th embodiment depicted in FIG. 24. A slide portion 6L is a constituent component of the copying apparatus 10L that plays the same role as the slide portion 6K. A frame 2L is a constituent component of the copying apparatus 10L that plays the same role as the frame 2K. Any other points are equal to the structures in the copying apparatus 10K.

The holding mechanism 26L includes a ratchet 261L, a claw-like portion 262L, and an actuator 263L.

The ratchet 261L is disposed to the slide portion 6L.

The claw-like portion 262L is disposed to the frame 2L. The claw-like portion 262L can move to protrude in a direction of the ratchet 261L by the actuator 263L. The claw-like portion 262L protrudes to be fitted in the ratchet 261L. The claw-like portion 262L is disposed to be inclined in such a manner that a distal end portion thereof (a ratchet 261L side) is provided on an upper side. The claw-like portion 262L is not inclined downwards since a stopper is provided.

The actuator 263L is disposed to the frame 2L. The actuator 263L performs an operation of protruding and retracting the claw-like portion 262L by using a non-illustrated control device.

Figure 27:
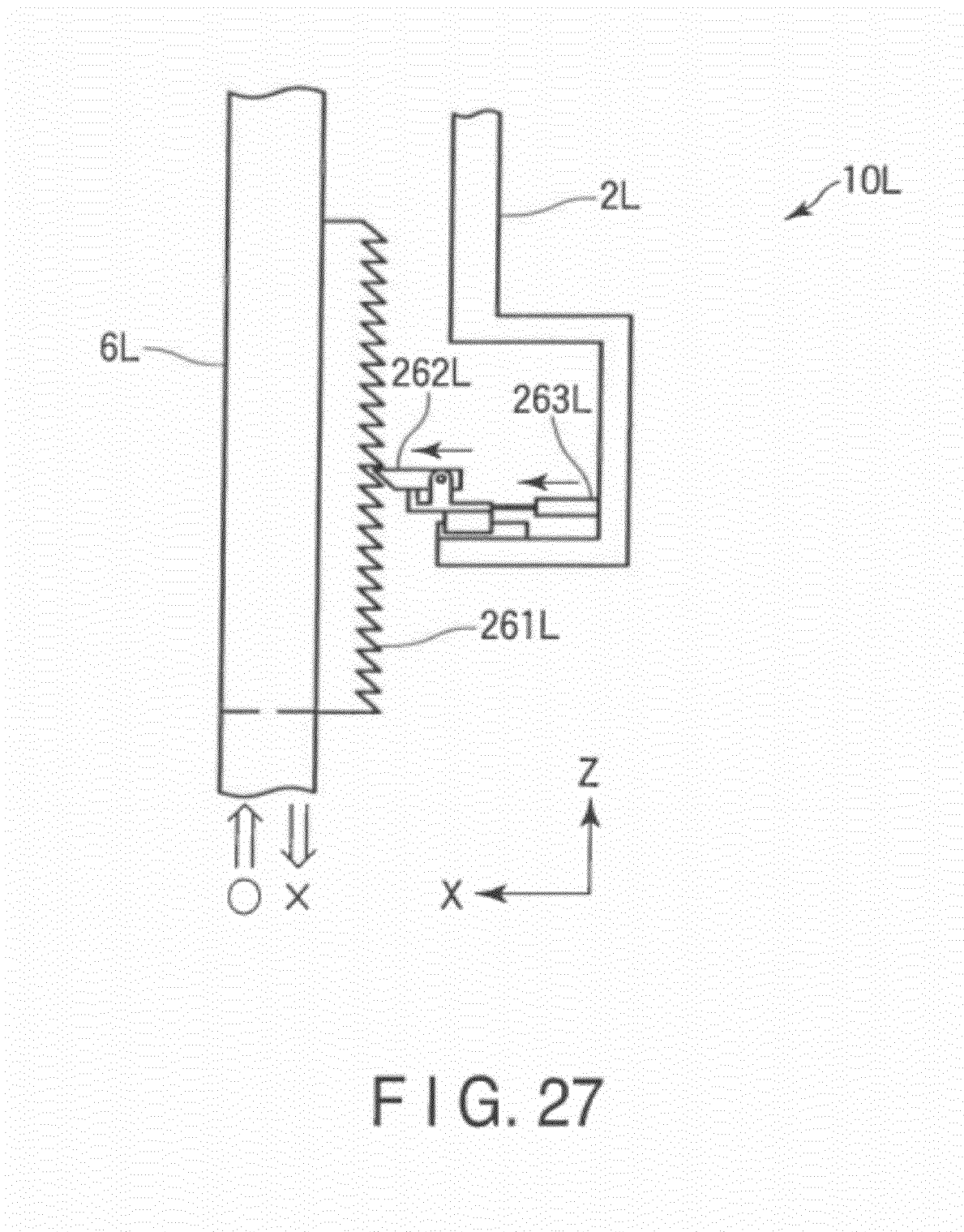
FIG. 27 is a front view showing a state where a holding mechanism of the copying apparatus according to the 13th embodiment of the present invention is operated.
Figure 28:
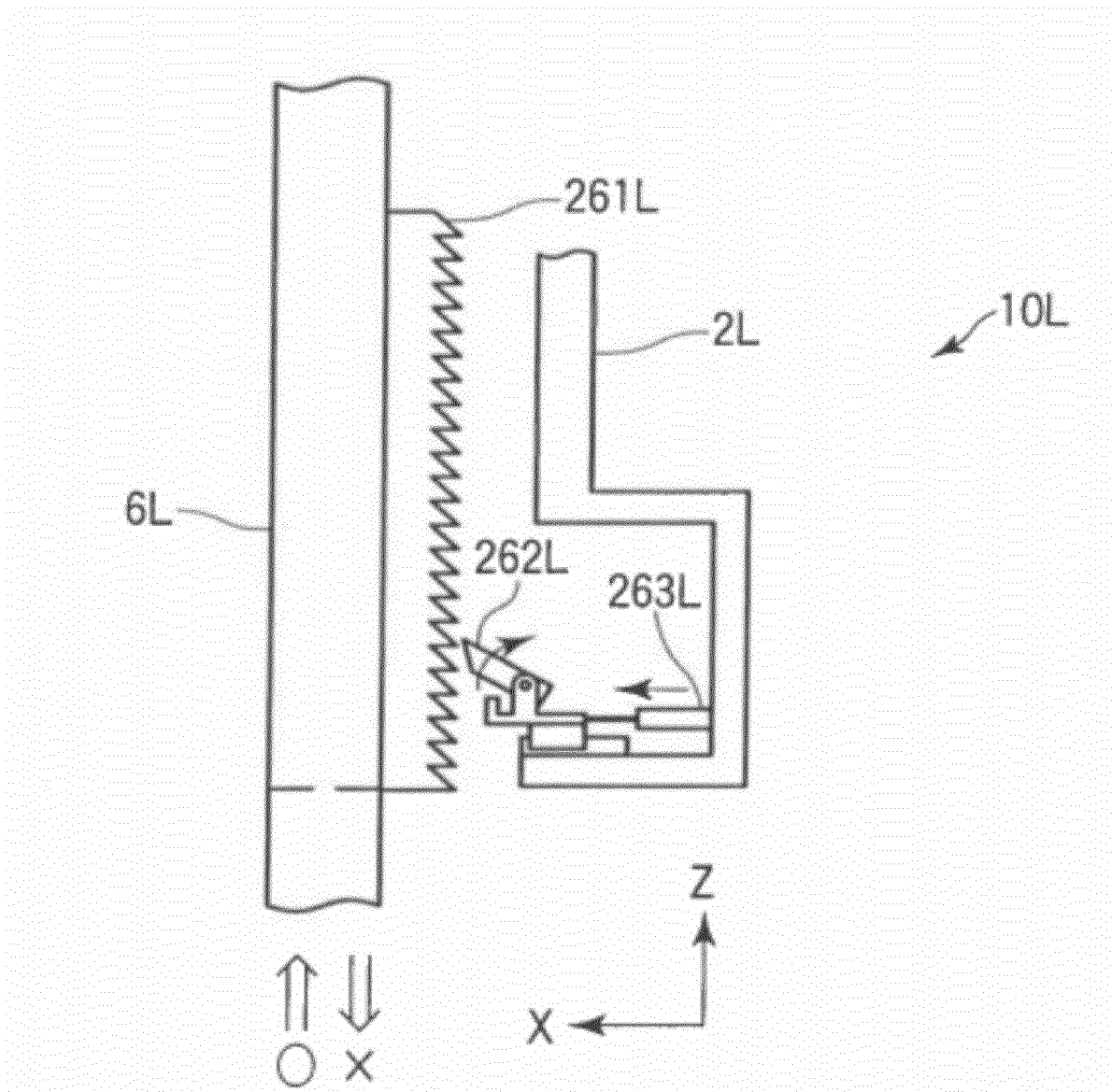
FIG. 28 is a front view showing a state where the holding mechanism of the copying apparatus according to the 13th embodiment of the present invention is operated.

"○" or "X" shown in FIGS. 26 to 28 indicates whether the slide portion 6L can move in a direction of an arrow. "○" indicates that the slide portion 6L can move in a direction of the arrow. "X" indicates that the slide portion 6L cannot move in a direction of the arrow.

FIG. 26 shows the copying apparatus 10L in a state where the holding mechanism 26L is not actuated. At this time, the slide portion 6L can freely move in an up-and-down direction in the Z axis direction.

FIG. 27 is a front view showing a state where the holding mechanism 26L of the copying apparatus 10L according to this embodiment is actuated. At this time, the ratchet 261L and the claw-like portion 262L are meshed with each other. As a result, the copying apparatus 10L fixes movement of the slide portion 6L in a downward direction of the Z axis direction.

FIG. 28 is a front view showing a state where the holding mechanism 26L of the copying apparatus 10L according to this embodiment is actuated. A state of the holding mechanism 26L depicted in FIG. 28 corresponds to a state where a force is applied to the slide portion 6L in an upward direction of the Z axis direction from the state where the ratchet 261L and the claw-like portion 262L of the holding mechanism 26L shown in FIG. 27 are meshed with each other.

Since the claw-like portion 262L is disposed in such a manner the distal end portion thereof is inclined in the upward direction, the slide portion 6L can move in the upward direction of the Z axis direction even in the state where the ratchet 261L and the claw-like portion 262L are meshed with each other. A timing at which a force is applied to the slide portion 6L in the upward direction in the Z axis direction is, e.g., a timing at which the shoe 1 receives a force due to a shape of the workpiece 100 during the copying operation of the copying apparatus 10L.

According to this embodiment, providing the holding mechanism 26L in place of the holding mechanism 25K enables obtaining the same functions and effects as those in the 12th embodiment.

It is to be noted that the linear slide type ratchet 261L has been described, but any other configuration may be adopted. For example, a gear-like rotating object may be provided in place of the ratchet 261L.

14th Embodiment

Figure 30:
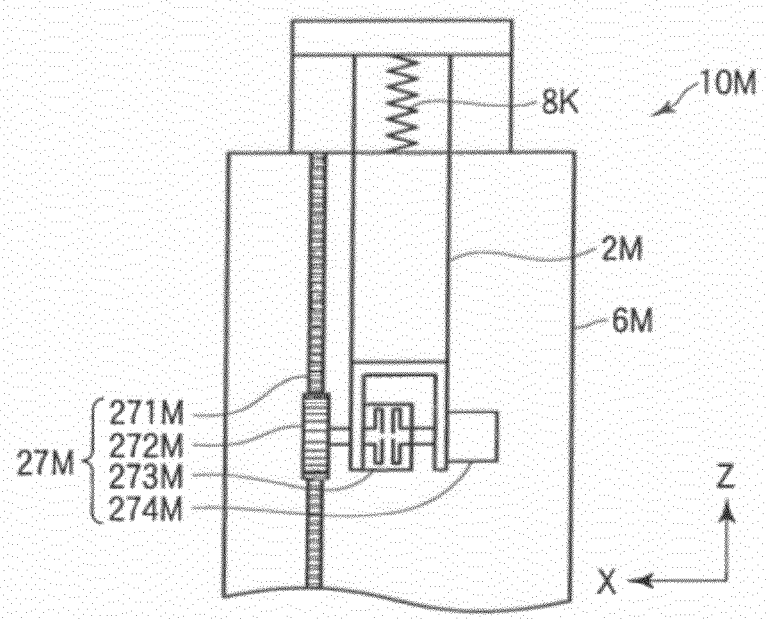
FIG. 30 is a side view showing a part of the configuration of the copying apparatus according to the 14th embodiment of the present invention.

FIG. 29 is a front view showing a configuration of a copying apparatus 10M according to a 14th embodiment of the present invention. FIG. 30 is a side view showing a part of the configuration of the copying apparatus 10M according to this embodiment.

The copying apparatus 10M has a configuration where the holding mechanism 25K is substituted by a holding mechanism 27M in the copying apparatus 10K according to the 12th embodiment depicted in FIG. 24. A slide portion 6M is a constituent component of the copying apparatus 10M that plays the same role as the slide portion 6K. A frame 2M is a constituent component of the copying apparatus 10M that plays the same role as the frame 2K. Any other points are equal to the structures in the copying apparatus 10K.

The holding mechanism 27M includes a rack 271M, a gear 272M, a clutch 273M, and a free wheel 274M.

The rack 271M is disposed on a side surface of the slide portion 6M in the Z direction.

The gear 272M is disposed in such a manner that teeth thereof mesh with teeth of the rack 271M.

The clutch 273M is provided between the gear 272M and the free wheel 274M. The clutch 273M is a mechanism that connects or disconnects respective rotary shafts of the gear 272M and the free wheel 274M.

The free wheel 274M has no load in rotation in one rotating direction, and hence freely rotates. A load is applied to rotation of the free wheel 274M in an opposite rotating direction. Specifically, the free wheel 274M freely rotates in a direction along which the gear 272M is rotated to move up the slide portion 6M. A load is applied to rotation of the free wheel 274M in a direction along which the gear 272M is rotated to move down the slide portion 6M.

An operation of the holding mechanism 27M will now be described.

In a state where the clutch 273M is not connected, the holding mechanism 27M does not restrict movement of the slide portion 6M in the Z direction. Therefore, the shoe 1 freely operates to copy the surface of the workpiece 100 in the Z direction.

In a state where the clutch 273M is connected, the holding mechanism 27M does not restrict movement in a direction along which the slide portion 6M is moved up (an upward direction of the Z axis). Therefore, even if the shoe 1 interferes with the workpiece 100, the shoe 1 operates to avoid interference in the upward direction. As a result, the shoe 1 does not apply an excessive force to the workpiece 100. Movement in the direction along which the slide portion 6M is moved up (the upward direction of the Z axis) is not restricted.

In a state where the clutch 273M is connected, a load is applied to the holding mechanism 27M in regard to movement in a direction along which the slide portion 6M is moved down (a downward direction of the Z axis). Therefore, when the clutch 273M is connected before the shoe 1 passes an opening portion OP of the workpiece 100 during the copying operation, the slide portion 6M does not move down even though it passes the opening portion OP.

According to this embodiment, providing the holding mechanism 27M in place of the holding mechanism 25K enables obtaining the same functions and effects as those of the 12th embodiment.

15th Embodiment

Figure 31:
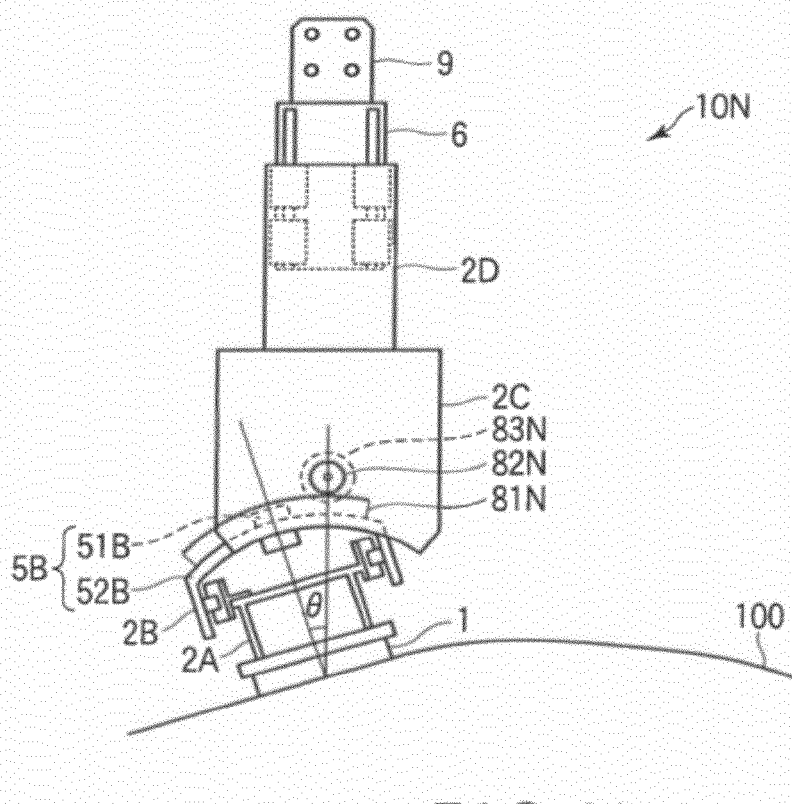
FIG. 31 is a side view showing a configuration of a copying apparatus according to a 15th embodiment of the present invention.

FIG. 31 is a side view showing a configuration of a copying apparatus 10N according to a 15th embodiment of the present invention.

The copying apparatus 10N has a configuration in which a gear 81N, a gear 82N, and a rotary encoder 83N are added to the configuration of the copying apparatus 10 according to the first embodiment depicted in FIG. 1. Any other points are the same as those in the copying apparatus 10.

The gear 81N is provided on a rail 52B of an arched slide guide 5B. Arched teeth are provided to an upper portion of the gear 81N.

The gear 82N is provided to mesh with the gear 81N. The gear 82N is a circular gear.

The rotary encoder 83N is disposed to the gear 82N. The rotary encoder 83N measures an angle at which a shoe 1 copies a workpiece 100.

An operation of measuring an angle by the rotary encoder 83N of the copying apparatus 10N will now be described.

When the shoe 1 is pressed against the workpiece 100, the rail 52B swivels in accordance with a surface shape of the workpiece 100.

When the rail 52B swivels, the gear 81N provided to the rail 52B swivels.

When the gear 81N swivels, the gear 82N meshed with the gear 81N rotates.

When the gear 82N rotates, the rotary encoder 83N disposed to the gear 82N rotates.

The rotary encoder 83N measure a rotating angle. This angle is an angle $\theta$ of the surface of the workpiece 100 that is copied by the copying apparatus 10N at a current moment. Therefore, when the copying apparatus 10N copies the workpiece 100 on a horizontal plane, the angle $\theta$ is 0 degree.

Figure 32:
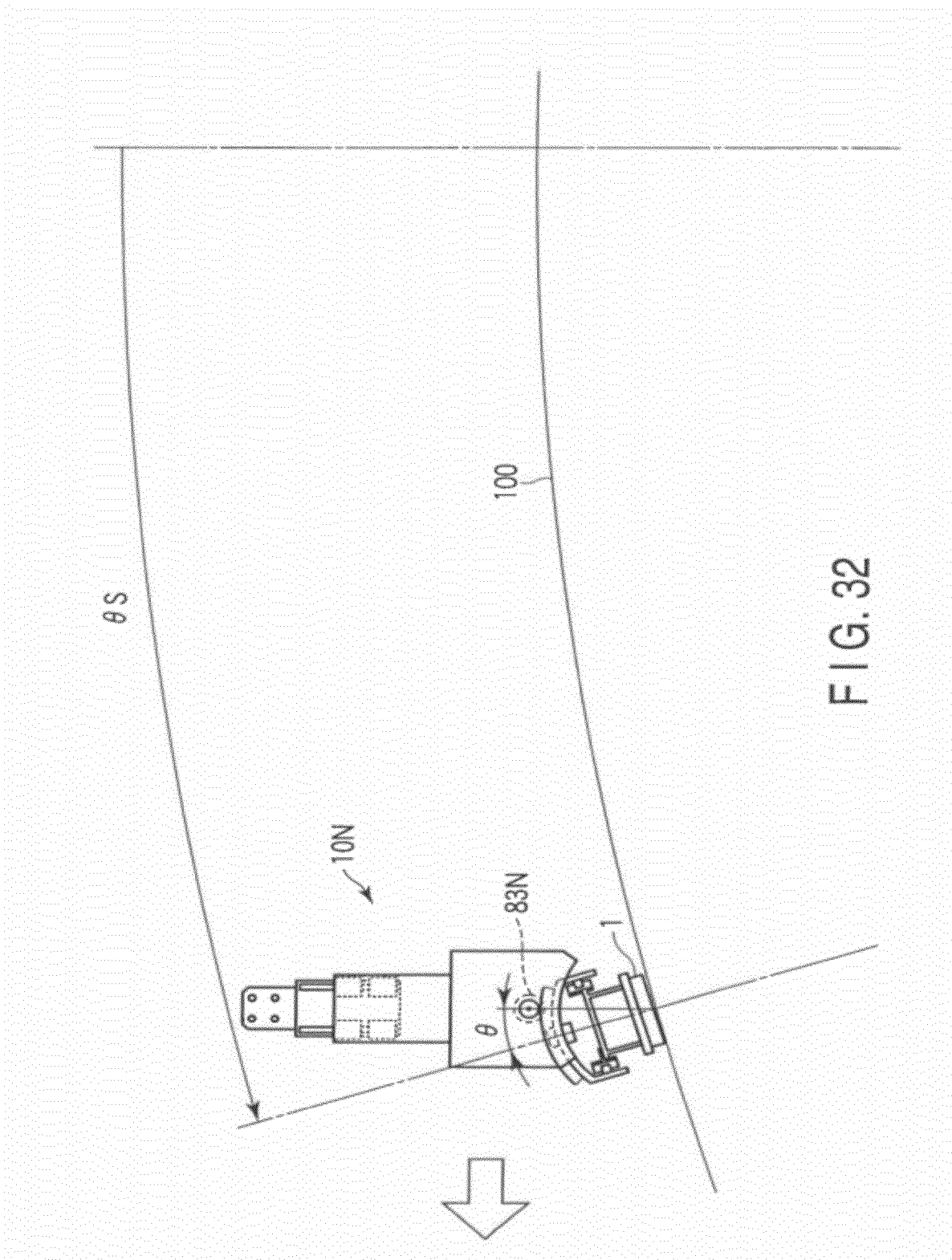
FIG. 32 is a side view showing a copying operation state of the copying apparatus according to the 15th embodiment of the present invention.

FIG. 32 is a side view showing a copying operation state of the copying apparatus 10N according to this embodiment.

A first usage of the copying apparatus 10N will now be described with reference to FIG. 32. This usage is a method of controlling the copying operation of the copying apparatus 10N based on a relative change of the angle measured by the rotary encoder 83N.

An angle $\theta S$ as a difference between an angle of the workpiece 100 copied by the copying apparatus 10N at the start and an angle of the same at the end is first determined.

Then, the copying apparatus 10N copies the workpiece 100. The rotary encoder 83N measures the angle $\theta$ while the copying apparatus 10N copies the workpiece 100. The copying apparatus 10N terminates the copying operation when the measurement target angle $\theta$ is changed for an angle $\theta S$ from the angle at the start point of the copying operation.

FIG. 33 is a schematic view showing a copying operation state performed by the copying apparatus 10N according to this embodiment with respect to the workpiece 100 having a cylindrical shape.

A second usage of the copying apparatus 10N will now be described with reference to FIG. 33. This usage is a method of controlling the copying operation of the copying apparatus 10N based on an absolute change in an angle measured by the rotary encoder 83N. This usage is suitable for an operation of copying a circular surface of the workpiece 100.

An angle $\theta max$ is set in a non-illustrated control device which controls the feeder apparatus 15. The angle $\theta max$ is an angle at which the shoe 1 is inclined when the copying apparatus 10N reaches the closest position for an end portion of the workpiece 100 in a copying range of the copying apparatus 10N with respect to the workpiece 100. That is, when the workpiece 100 to be copied has a circular shape, the angle $\theta max$ is an angle at which an inclination of the shoe 1 is maximum in the copying range.

Then, the feeder apparatus 15 sets up the copying apparatus 10N at an arbitrary position in the copying range for the workpiece 100.

The feeder apparatus 15 allows the copying apparatus 10N to perform the copying operation in one of the directions of the workpiece 100 as long as an angle measured by the rotary encoder 83N does not reach the angle $\theta max$.

When the angle measured by the rotary encoder 83N reaches the angle $\theta max$, the feeder apparatus 15 stops the copying operation of the copying apparatus 10N. The feeder apparatus 15 reverses the direction of the copying operation performed by the copying apparatus 10N. The feeder apparatus 15 moves the copying apparatus 10N in the reversed direction (a direction along which the workpiece 100 is not copied yet).

When the angle measured by the rotary encoder 83N reaches the angle $\theta max$, the feeder apparatus 15 stops the copying operation of the copying apparatus 10N.

In this manner, the copying apparatus 10N can copy a necessary range of the workpiece 100. It is to be noted that the copying apparatus 10N is arranged at an arbitrary position in the copying range for the workpiece 100 in the above description, but the copying apparatus 10N may be placed at an end of the copying range (a position where the shoe 1 is inclined at the angle $\theta max$). In this case, just moving the copying apparatus 10N in one direction alone by the feeder apparatus 15 enables copying the entire workpiece 100.

Figure 34:
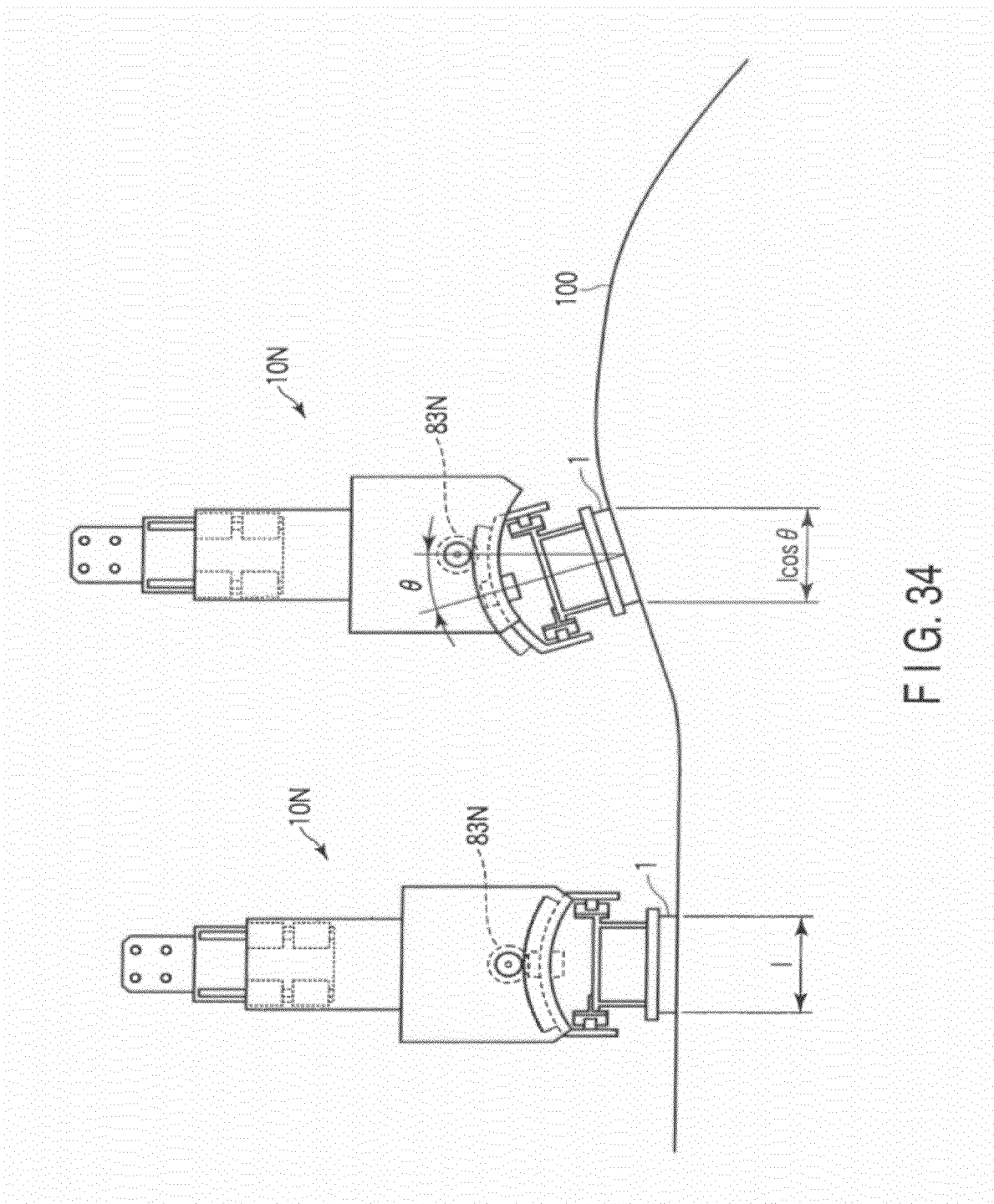
FIG. 34 is a side view for explaining an index amount of the copying apparatus according to the 15th embodiment of the present invention.

FIG. 34 is a side view for explaining an index amount of the copying apparatus 10N according to this embodiment.

A method of calculating an index amount when moving the copying apparatus 10N will now be described with reference to FIG. 34.

Various shapes of the workpiece 100 can be supposed. Therefore, a flat surface, an inclined surface, a curves surface, and others of the workpiece 100 may be included. Thus, an index amount as a component in a horizontal direction of a distance for which the copying apparatus 10 is moved may differ depending on a shape of the workpiece 100.

Here, it is assumed that an index amount is 1 when the copying apparatus 10N copies a flat surface portion of the workpiece 100. When the copying apparatus 10N copies the flat surface portion of the workpiece 100, an angle measured by the rotary encoder 83N is 0 degree.

When the copying apparatus 10N copies an inclined surface portion of the workpiece 100, the angle measured by the rotary encoder 83N is an inclination angle $\theta$ of this inclined surface. At this time, the next index amount is l cos θ. That is, a cosine component of the angle measured by the rotary encoder 83N is the next index amount with respect to the index amount l of the flat surface portion of the workpiece 100.

In this manner, the copying apparatus 10N copies the workpiece 100 while measuring the angle θ by the rotary encoder 83N. The next index amount l cos θ is calculated based on the measured angle θ, thereby moving the copying apparatus 10N.

Figure 35:
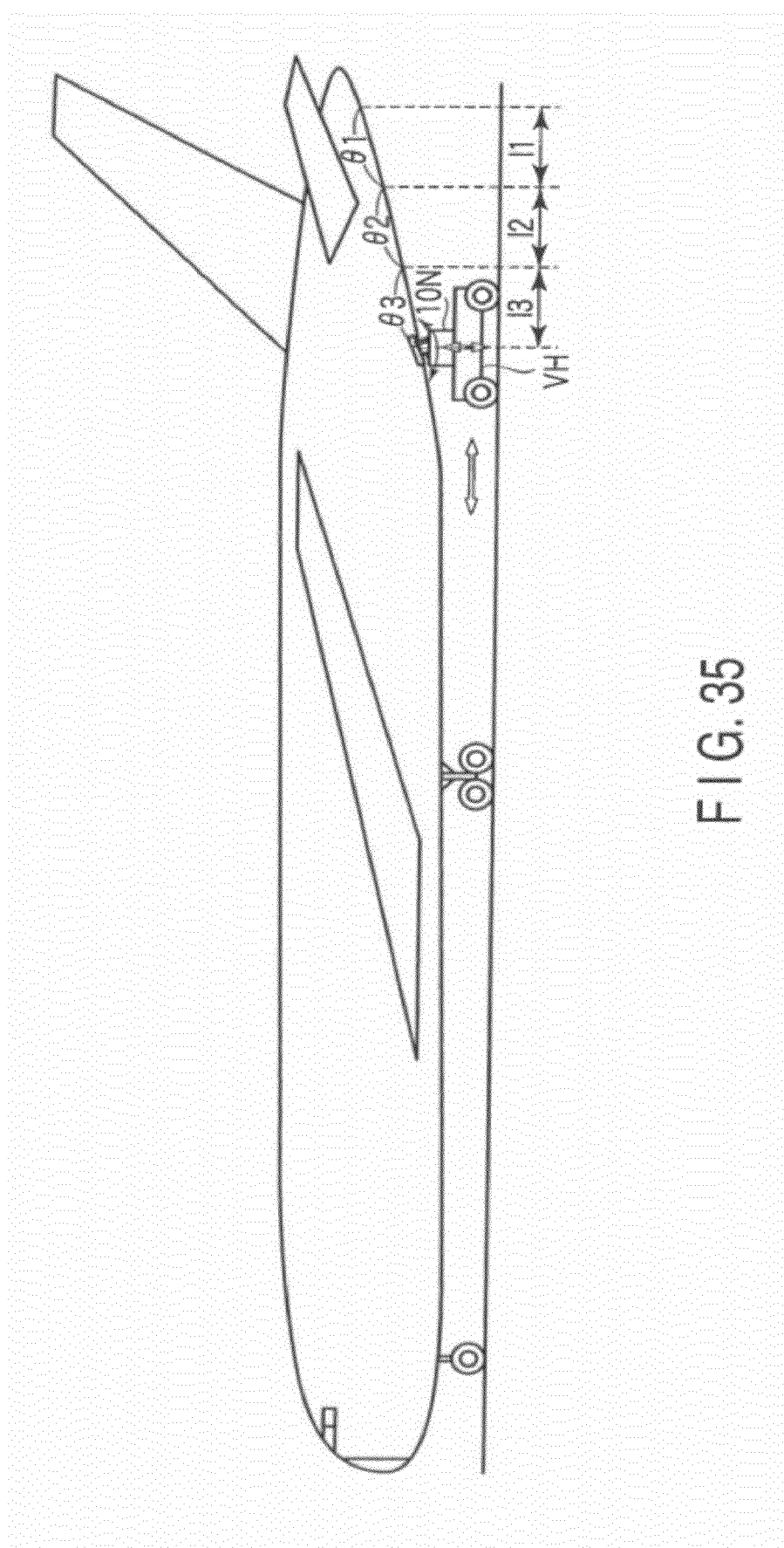
FIG. 35 is a block diagram showing a configuration where the copying apparatus according to the 15th embodiment of the present invention is mounted on a running vehicle.

FIG. 35 is a block diagram showing a configuration in which the copying apparatus 10N according to this embodiment is mounted on a running vehicle VH.

The running vehicle VH is a vehicle having the copying apparatus 10N mounted thereon. The copying apparatus 10N is an ultrasonic flaw detection apparatus having an ultrasonic flaw detector provided to the shoe 1. The running vehicle VH may be a self-propelled type vehicle that runs by itself or a vehicle that runs based on external control.

A method of using the running vehicle VH to copy a lower portion of a body of an aircraft with the copying apparatus 10N (a method of performing ultrasonic flaw detection) will now be described.

The running vehicle VH is set up at an arbitrary position below the body of the aircraft.

The running vehicle VH copies the body lower portion of the aircraft while measuring an angle θ by using the rotary encoder 83N. That is, the running vehicle VH performs ultrasonic flaw detection with respect to the body lower portion of the aircraft by using the copying apparatus 10N while measuring the angle θ (an inclination of a surface shape of the body lower portion of the aircraft).

Like the above description, the running vehicle VH calculates the next index amounts l1, l2, and l3 based on measured angles θ1, θ2, and θ3. The running vehicle VH moves based on the calculated index amounts.

According to this embodiment, providing the rotary encoder 83N enables reducing an operation of performing various kinds of calculations in preparation for copying the workpiece 100. For example, the various kinds of calculations correspond to an index amount required to move the copying apparatus 10N, positioning (a start position or an end position) of the copying apparatus 10N when performing the copying operation, a shape of the workpiece 100, a distance for which the copying apparatus 10N copies the workpiece 100, a distance between the workpiece 100 and the copying apparatus 10N, and others.

Further, in a case where the workpiece 100 has a cylindrical shape, a previously planned range of the workpiece 100 be all copied by setting a limit angle θmax in advance to perform an operation based on an angle measured by the rotary encoder 83N. As a result, an initial position of the copying apparatus 10N does not have to be accurately determined.

Furthermore, the copying operation performed by the copying apparatus 10N can be associated with the workpiece 100 having various shapes by calculating the next index amount while measuring an inclination angle of the workpiece 100.

Moreover, when the copying apparatus 10N is mounted on the running vehicle VH as an ultrasonic flaw detection apparatus, ultrasonic flaw detection for an aircraft which is in service can be effected. That is, even if an aircraft is not present at a specified position like a manufacturing step or the like, flaws of the aircraft stopped at an arbitrary position can be detected. Additionally, since the running vehicle VH can move to an arbitrary position on the ground, the copying apparatus 10N can perform flaw detection in an arbitrary range of an extensive workpiece like an aircraft.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A copying apparatus that copies a workpiece, comprising:
   a shoe that comes into contact with a portion of the workpiece to be copied;
   a first swiveling unit that swivels with the shoe in an arc pattern around a point, as a swiveling center, on a plane where the shoe comes into contact with the portion of the workpiece to be copied;
   a second swiveling unit that swivels with the shoe in an arc pattern around the swiveling center of the first swiveling unit in a direction orthogonal to a direction along which the shoe is swiveled with the first swiveling unit; and
   a translation sliding unit that linearly slides the shoe in a direction which presses the shoe against the portion of the workpiece to be copied.

2. The apparatus according to claim 1, further comprising:
   a buffering unit that buffers a pressing force caused by sliding of the translation sliding unit.

3. The apparatus according to claim 2, wherein the buffering unit is an air pressure buffering unit that performs buffering by using an air pressure, and the apparatus further comprises an air pressure adjusting unit that adjusts the air pressure of the air pressure buffering unit.

4. The apparatus according to claim 3, wherein the air pressure adjusting unit adjusts the air pressure of the air pressure buffering unit such that the shoe presses against the portion of the workpiece to be copied.

5. The apparatus according to claim 3, wherein the air pressure adjusting unit adjusts the air pressure of the air pressure buffering unit such that the shoe is pulled up.

6. The apparatus according to claim 1, further comprising:
   a first braking unit that brakes swiveling of the shoe by the first swiveling unit; and
   a second braking unit that brakes swiveling of the shoe by the second swiveling unit.

7. The apparatus according to claim 6, further comprising:
   a sensor provided downstream of the shoe with respect to a direction in which the workpiece is copied, and configured to detect whether the portion of the workpiece to be copied exists,
   wherein when the sensor detects that the portion of the workpiece to be copied does not exist, at least one of the first braking unit and the second braking unit operates.

8. The apparatus according to claim 1, further comprising:
   a first braking unit that brakes swiveling of the shoe by the first swiveling unit;
   a second braking unit that brakes swiveling of the shoe by the second swiveling unit; and
   a translation sliding braking unit that brakes sliding by the translation sliding unit.

9. The apparatus according to claim 8, wherein the translation sliding braking unit comprises:
   a cylinder that operates based on an air pressure; and
   a pad that produces a frictional force to brake sliding by the translation sliding unit based on an operation of the cylinder.

10. The apparatus according to claim 8, wherein the translation sliding braking unit comprises:
a ratchet; and
a claw that is caught on the ratchet, and brakes the translation sliding unit moving in a direction along which the shoe presses against the portion of the workpiece to be copied, but does not brake the translation sliding unit moving in a direction along which the shoe moves away from the portion of the workpiece to be copied.

11. The apparatus according to claim 8, wherein the translation sliding braking unit comprises:
a first gear;
a second gear that meshes with the first gear;
a free wheel that brakes the translation sliding unit rotating in a direction along which the shoe presses against the portion of the workpiece to be copied, but does not brake the translation sliding unit rotating in a direction along which the shoe moves away from the portion of the workpiece to be copied; and
a clutch that disconnects and connects a rotary shaft of the second gear and a rotary shaft of the free wheel.

12. The apparatus according to claim 8, wherein the translation sliding braking unit brakes the translation sliding unit moving in a direction in which the shoe presses against the portion of the workpiece to be copied, and does not brake the translation sliding unit moving in a direction in which the shoe moves away from the portion of the workpiece to be copied.

13. The apparatus according to claim 1, further comprising:
a correcting unit that corrects an influence of swiveling of the first swiveling unit due to a gravitational force by using a counterweight.

14. The apparatus according to claim 1, further comprising:
a distance measuring unit that measures a distance for which the portion of the workpiece to be copied is displaced in a direction along which the shoe presses against the portion of the workpiece to be copied.

15. The apparatus according to claim 1, further comprising:
an angle measuring unit that measures an angle at which the shoe is inclined.

16. An ultrasonic flaw detection apparatus comprising:
a shoe that comes into contact with a portion of a workpiece to be copied;
a first swiveling unit that swivels with the shoe in an arc pattern around a point, as a swiveling center, on a plane where the shoe comes into contact with the portion of the workpiece to be copied;
a second swiveling unit that swivels with the shoe in an arc pattern around the swiveling center of the first swiveling unit in a direction orthogonal to a direction along which the shoe is swiveled with the first swiveling unit,
a translation sliding unit that linearly slides the shoe in a direction which presses the shoe against the portion of the workpiece to be copied; and
an ultrasonic flaw detector that is provided to the shoe and generates ultrasound toward the portion of the workpiece to be copied to detect flaws.

17. The apparatus according to claim 16, further comprising:
a moving unit on which the apparatus is mounted, and which moves to an arbitrary position on the ground.

18. An ultrasonic flaw detection method of performing flaw detection with respect to the portion of the workpiece to be copied by using the ultrasonic flaw detection apparatus according to claim 16, the method comprising:
bringing the ultrasonic flaw detection apparatus into contact with the portion of the workpiece to be copied;
rotating the workpiece with the ultrasonic flaw detection apparatus kept in contact with the portion of the workpiece to be copied; and
controlling an amount of press of the ultrasonic flaw detection apparatus against the portion of the workpiece to be copied, in accordance with a rotational angle of the workpiece, with the ultrasonic flaw detection apparatus kept in contact with the portion of the workpiece to be copied.

19. The apparatus according to claim 16, further comprising:
a first braking unit that brakes swiveling of the shoe by the first swiveling unit; and
a second braking unit that brakes swiveling of the shoe by the second swiveling unit.

20. The apparatus according to claim 19, further comprising:
a translation sliding braking unit that brakes sliding by the translation sliding unit, wherein the translation sliding braking unit includes:
a cylinder that operates based on an air pressure; and
a pad that produces a frictional force to brake sliding by the translation sliding unit based on an operation of the cylinder.

21. The apparatus according to claim 19, further comprising:
a translation sliding braking unit that brakes sliding by the translation sliding unit, wherein the translation sliding braking unit includes:
a ratchet; and
a claw that is caught on the ratchet, and brakes the translation sliding unit moving in a direction along which the shoe presses against the portion of the workpiece to be copied, but does not brake the translation sliding unit moving in a direction along which the shoe moves away from the portion of the workpiece to be copied.

22. The apparatus according to claim 19, further comprising:
a translation sliding braking unit that brakes sliding by the translation sliding unit, wherein the translation sliding braking unit includes:
a first gear;
a second gear that meshes with the first gear;
a free wheel that brakes the translation sliding unit rotating in a direction along which the shoe presses against the portion of the workpiece to be copied, but does not brake the translation sliding unit rotating in a direction along which the shoe moves away from the portion of the workpiece to be copied; and
a clutch that disconnects and connects a rotary shaft of the second gear and a rotary shaft of the free wheel.

* * * * *